US012778619B2

(12) United States Patent
Al-Jadda et al.

(10) Patent No.: US 12,778,619 B2
(45) Date of Patent: Nov. 3, 2026

(54) THROMBUS REMOVAL SYSTEMS AND ASSOCIATED METHODS

(71) Applicant: Shifamed Holdings, LLC, Campbell, CA (US)

(72) Inventors: Aadel Al-Jadda, San Carlos, CA (US); Tom Saul, Portland, OR (US); Kevin Muller, San Carlos, CA (US); Amr Salahieh, Saratoga, CA (US); Paul Gunning, Montara, CA (US); Claudio Argento, Felton, CA (US); Nicholas Lyford, Saratoga, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 287 days.

(21) Appl. No.: 18/568,656

(22) PCT Filed: Jun. 10, 2022

(86) PCT No.: PCT/US2022/033024
§ 371 (c)(1),
(2) Date: Dec. 8, 2023

(87) PCT Pub. No.: WO2022/261448
PCT Pub. Date: Dec. 15, 2022

(65) Prior Publication Data

US 2026/0000423 A1 Jan. 1, 2026

Related U.S. Application Data

(60) Provisional application No. 63/335,656, filed on Apr. 27, 2022, provisional application No. 63/285,054, (Continued)

(51) Int. Cl.

| | |
|---|---|
| *A61B 17/3203* | (2006.01) |
| *A61B 17/00* | (2006.01) |
| *A61B 17/22* | (2006.01) |

(52) U.S. Cl.
CPC .................. *A61B 17/32037* (2013.01); *A61B 2017/00057* (2013.01); *A61B 2017/00106* (2013.01); *A61B 2017/22079* (2013.01)

(58) Field of Classification Search
CPC .... A61B 17/32037; A61B 2017/00057; A61B 2017/00106; A61B 2017/22079
See application file for complete search history.

(56) References Cited

U.S. PATENT DOCUMENTS 4,006,745 A 2/1977 Sorenson et al.
4,148,307 A 4/1979 Utsugi
(Continued)

FOREIGN PATENT DOCUMENTS

CN 102727643 A 10/2012
CN 103417261 A 10/2013
(Continued)

OTHER PUBLICATIONS

Dala et al.; U.S. Appl. No. 18/994,012 entitled "Thrombus removal systems and associated methods," filed Jan. 13, 2021.
(Continued)

*Primary Examiner* — Ashley L Fishback
(74) *Attorney, Agent, or Firm* — Shay Glenn LLP

(57) ABSTRACT

The present technology relates to systems and methods for removing a thrombus from a blood vessel of a patient. In some embodiments, the present technology is directed to systems including an elongated catheter having a distal portion configured to be positioned within the blood vessel of the patient, a proximal portion configured to be external to the patient, and a lumen extending therebetween. The system can also include a fluid delivery mechanism coupled with a fluid lumen and configured to apply fluid to at least partially fragment the thrombus.

22 Claims, 27 Drawing Sheets

Related U.S. Application Data filed on Dec. 1, 2021, provisional application No. 63/250,089, filed on Sep. 29, 2021, provisional application No. 63/209,257, filed on Jun. 10, 2021.

(56) References Cited

U.S. PATENT DOCUMENTS

| | | | |
|---|---|---|---|
| 4,577,621 | A | 3/1986 | Patel |
| 4,954,251 | A | 9/1990 | Barnes et al. |
| 5,114,581 | A | 5/1992 | Goldsmith et al. |
| 5,135,482 | A | 8/1992 | Neracher |
| 5,651,776 | A | 7/1997 | Appling et al. |
| 5,662,671 | A | 9/1997 | Barbut et al. |
| 5,788,647 | A | 8/1998 | Eggers |
| 5,795,322 | A | 8/1998 | Boudewijn et al. |
| 5,989,271 | A | 11/1999 | Bonnette et al. |
| 5,993,469 | A | 11/1999 | McKenzie et al. |
| 6,004,339 | A | 12/1999 | Wijay |
| 6,053,870 | A | 4/2000 | Fulton, III |
| 6,059,825 | A | 5/2000 | Hobbs et al. |
| 6,074,374 | A | 6/2000 | Fulton |
| 6,086,534 | A | 7/2000 | Kesten |
| 6,228,052 | B1 | 5/2001 | Pohndorf |
| 6,283,950 | B1 | 9/2001 | Appling |
| 6,287,333 | B1 | 9/2001 | Appling et al. |
| 6,306,163 | B1 | 10/2001 | Fitz |
| 6,315,762 | B1 | 11/2001 | Recinella et al. |
| 6,361,545 | B1 | 3/2002 | Macoviak et al. |
| 6,524,300 | B2 | 2/2003 | Meglin |
| RE38,074 | E | 4/2003 | Recinella et al. |
| 6,582,447 | B1 | 6/2003 | Patel et al. |
| 6,620,148 | B1 | 9/2003 | Tsugita |
| 6,719,717 | B1 | 4/2004 | Johnson et al. |
| 6,733,489 | B2 | 5/2004 | Nutting et al. |
| 6,827,701 | B2 | 12/2004 | MacMahon et al. |
| 6,875,193 | B1 | 4/2005 | Bonnette et al. |
| 6,881,218 | B2 | 4/2005 | Beyer et al. |
| 6,942,635 | B2 | 9/2005 | Rosenblatt et al. |
| 6,966,886 | B2 | 11/2005 | Appling |
| 7,033,347 | B2 | 4/2006 | Appling |
| 7,131,981 | B2 | 11/2006 | Appling et al. |
| 7,163,533 | B2 | 1/2007 | Hobbs et al. |
| 7,217,256 | B2 | 5/2007 | Di Palma |
| 7,220,269 | B1 | 5/2007 | Ansel et al. |
| 7,273,478 | B2 | 9/2007 | Appling et al. |
| 7,279,000 | B2 | 10/2007 | Cartier et al. |
| 7,344,533 | B2 | 3/2008 | Pearson et al. |
| 7,347,852 | B2 | 3/2008 | Hobbs et al. |
| 7,419,487 | B2 | 9/2008 | Johnson et al. |
| 7,422,586 | B2 | 9/2008 | Morris et al. |
| 7,455,675 | B2 | 11/2008 | Schur et al. |
| 7,458,967 | B2 | 12/2008 | Appling et al. |
| 7,483,457 | B2 | 1/2009 | Howe et al. |
| 7,544,202 | B2 | 6/2009 | Cartier et al. |
| D595,892 | S | 7/2009 | Smith et al. |
| 7,563,247 | B2 | 7/2009 | Maguire et al. |
| D603,044 | S | 10/2009 | Appling et al. |
| 7,618,411 | B2 | 11/2009 | Appling |
| 7,717,900 | B2 | 5/2010 | di Palma |
| 7,722,635 | B2 | 5/2010 | Beyer et al. |
| 7,740,616 | B2 | 6/2010 | Smith et al. |
| 7,765,010 | B2 | 7/2010 | Chornenky et al. |
| 7,766,961 | B2 | 8/2010 | Patel et al. |
| 7,771,401 | B2 | 8/2010 | Hekmat et al. |
| 7,780,628 | B1 | 8/2010 | Keren et al. |
| D626,231 | S | 10/2010 | Perchik |
| 7,826,904 | B2 | 11/2010 | Appling et al. |
| 7,833,215 | B2 | 11/2010 | Appling |
| RE42,016 | E | 12/2010 | Chornenky et al. |
| D630,321 | S | 1/2011 | Hamilton |
| D631,154 | S | 1/2011 | Hamilton |
| 7,914,503 | B2 | 3/2011 | Goodson et al. |
| RE42,277 | E | 4/2011 | Jaafar et al. |
| 7,938,824 | B2 | 5/2011 | Chornenky et al. |
| 7,942,873 | B2 | 5/2011 | Kwan et al. |
| 7,947,019 | B2 | 5/2011 | Perchik et al. |
| D640,788 | S | 6/2011 | Appling |
| 7,993,325 | B2 | 8/2011 | Elkins et al. |
| D644,735 | S | 9/2011 | Elbe et al. |
| RE42,835 | E | 10/2011 | Chornenky et al. |
| RE43,009 | E | 12/2011 | Chornenky et al. |
| D650,475 | S | 12/2011 | Smith et al. |
| 8,114,070 | B2 | 2/2012 | Rubinsky et al. |
| 8,167,903 | B2 | 5/2012 | Hardert et al. |
| 8,231,603 | B2 | 7/2012 | Hobbs et al. |
| 8,241,343 | B2 | 8/2012 | Douglass et al. |
| 8,317,773 | B2 | 11/2012 | Appling et al. |
| 8,328,760 | B2 | 12/2012 | Lareau |
| 8,328,768 | B2 | 12/2012 | Quigley et al. |
| 8,337,451 | B2 | 12/2012 | Lareau et al. |
| 8,337,470 | B2 | 12/2012 | Prasad et al. |
| 8,366,687 | B2 | 2/2013 | Girard et al. |
| 8,372,064 | B2 | 2/2013 | Douglass et al. |
| 8,377,011 | B2 | 2/2013 | Weaver et al. |
| D677,798 | S | 3/2013 | Hart et al. |
| 8,425,455 | B2 | 4/2013 | Nentwick |
| 8,472,011 | B2 | 6/2013 | Cronin et al. |
| 8,475,488 | B2 | 7/2013 | Cartier et al. |
| 8,496,644 | B2 | 7/2013 | Graffam et al. |
| 8,506,512 | B2 | 8/2013 | Aklog et al. |
| 8,518,011 | B2 | 8/2013 | Goodson et al. |
| 8,535,306 | B2 | 9/2013 | Pearson et al. |
| 8,574,204 | B2 | 11/2013 | Bourne et al. |
| 8,585,678 | B2 | 11/2013 | Elkins et al. |
| 8,585,950 | B2 | 11/2013 | Appling et al. |
| 8,586,897 | B2 | 11/2013 | Cronin |
| 8,603,070 | B1 | 12/2013 | Lareau et al. |
| 8,607,428 | B2 | 12/2013 | Nentwick et al. |
| 8,613,717 | B2 | 12/2013 | Aklog et al. |
| 8,632,534 | B2 | 1/2014 | Pearson et al. |
| 8,663,116 | B2 | 3/2014 | Hamilton |
| 8,679,074 | B2 | 3/2014 | Daly et al. |
| 8,734,374 | B2 | 5/2014 | Aklog et al. |
| 8,734,439 | B2 | 5/2014 | Gough et al. |
| 8,753,292 | B2 | 6/2014 | Ingold et al. |
| 8,753,335 | B2 | 6/2014 | Moshe et al. |
| 8,784,402 | B1 | 7/2014 | Lareau et al. |
| 8,858,497 | B2 | 10/2014 | Di Palma et al. |
| 8,864,754 | B2 | 10/2014 | Appling et al. |
| 8,903,488 | B2 | 12/2014 | Callas et al. |
| 8,926,573 | B2 | 1/2015 | Smith et al. |
| 8,956,383 | B2 | 2/2015 | Aklog et al. |
| 8,992,513 | B2 | 3/2015 | Delaney |
| 9,033,914 | B2 | 5/2015 | Haarala et al. |
| 9,050,435 | B2 | 6/2015 | Lareau et al. |
| 9,055,964 | B2 | 6/2015 | Cartier et al. |
| 9,078,665 | B2 | 7/2015 | Moss et al. |
| 9,084,619 | B2 | 7/2015 | Cronin et al. |
| D736,916 | S | 8/2015 | Appling et al. |
| 9,149,607 | B2 | 10/2015 | Scheibe et al. |
| 9,161,811 | B2 | 10/2015 | Cronin |
| 9,173,704 | B2 | 11/2015 | Hobbs et al. |
| 9,186,491 | B2 | 11/2015 | Casiello et al. |
| D744,639 | S | 12/2015 | Aklog et al. |
| 9,205,242 | B2 | 12/2015 | Nardone et al. |
| 9,206,283 | B1 | 12/2015 | Santerre et al. |
| D748,774 | S | 2/2016 | Caron |
| 9,254,173 | B2 | 2/2016 | Cronin et al. |
| 9,339,328 | B2 | 5/2016 | Ortiz et al. |
| 9,351,861 | B2 | 5/2016 | Sherburne |
| 9,358,378 | B2 | 6/2016 | Hanson et al. |
| 9,402,938 | B2 | 8/2016 | Aklog et al. |
| 9,408,620 | B2 | 8/2016 | Rosenbluth et al. |
| 9,414,881 | B2 | 8/2016 | Callas et al. |
| 9,440,046 | B2 | 9/2016 | Hobbs et al. |
| 9,440,047 | B1 | 9/2016 | Elberse et al. |
| 9,445,746 | B1 | 9/2016 | Elberse et al. |
| 9,447,892 | B2 | 9/2016 | Lareau et al. |
| 9,480,497 | B2 | 11/2016 | Ingold et al. |
| 9,675,406 | B2 | 6/2017 | Moss et al. |
| 9,681,909 | B2 | 6/2017 | Bhargav et al. |
| 9,700,332 | B2 | 7/2017 | Marchand et al. |
| 9,700,368 | B2 | 7/2017 | Callas et al. |
| 9,707,339 | B2 | 7/2017 | Chartrand et al. |
| 9,757,197 | B2 | 9/2017 | Cronin et al. |

(56) References Cited

U.S. PATENT DOCUMENTS 9,764,115 B2 9/2017 Tegg
9,788,896 B2 10/2017 Cronin et al.
9,789,229 B1 10/2017 Lareau et al.
D802,409 S 11/2017 Caron
9,820,761 B2 11/2017 Garrison et al.
9,867,908 B2 1/2018 Lareau et al.
9,888,956 B2 2/2018 Model et al.
9,895,189 B2 2/2018 Pearson
9,895,524 B2 2/2018 Lareau
9,907,613 B2 3/2018 Cronin et al.
9,933,079 B2 4/2018 Weaver et al.
9,999,493 B2 6/2018 Nguyen et al.
10,004,531 B2 6/2018 Rosenbluth et al.
10,010,666 B2 7/2018 Rubinsky et al.
10,039,900 B2 8/2018 di Palma et al.
10,045,790 B2 8/2018 Cox et al.
10,098,651 B2 10/2018 Marchand et al.
10,105,477 B2 10/2018 Davey et al.
10,159,830 B2 12/2018 Miller
10,166,321 B2 1/2019 Casiello et al.
10,188,831 B2 1/2019 Elberse et al.
10,238,406 B2 3/2019 Cox et al.
D847,623 S 5/2019 Caron
10,279,112 B2 5/2019 Houde et al.
10,349,960 B2 7/2019 Quick
D860,941 S 9/2019 Wheeler
10,429,517 B1 10/2019 Isham et al.
10,492,805 B2 12/2019 Culbert et al.
10,493,257 B2 12/2019 Chartrand et al.
10,500,329 B2 12/2019 Weaver et al.
10,517,617 B2 12/2019 Aklog et al.
10,517,633 B2 12/2019 Nash et al.
D879,957 S 3/2020 Zabar et al.
10,610,678 B2 4/2020 Martin
10,660,691 B2 5/2020 McKernon et al.
10,782,425 B2 9/2020 Isham
10,786,270 B2 9/2020 Yang et al.
10,792,056 B2 10/2020 Vale et al.
10,806,896 B2 10/2020 Davies et al.
10,835,715 B2 11/2020 Cruz et al.
D908,204 S 1/2021 Casiello et al.
10,905,492 B2 2/2021 Neal
10,912,885 B2 2/2021 Maguire et al.
D916,280 S 4/2021 Swift
D916,281 S 4/2021 Swift
11,000,682 B2 5/2021 Merritt et al.
11,065,018 B2 7/2021 Busk et al.
11,154,314 B2 10/2021 Quick
11,241,564 B2 2/2022 Casiello et al.
11,259,824 B2 3/2022 Brady et al.
11,348,250 B2 5/2022 Koster et al.
11,433,218 B2 9/2022 Quick et al.
11,497,889 B2 11/2022 Mixter et al.
D972,720 S 12/2022 Cote et al.
D972,723 S 12/2022 Swift et al.
11,559,382 B2 1/2023 Merritt et al.
11,607,150 B2 3/2023 Schweikert et al.
11,648,020 B2 5/2023 Cote et al.
11,710,242 B2 7/2023 Wang et al.
11,730,924 B2 8/2023 Saadat et al.
11,832,837 B2 12/2023 Hauser
11,864,779 B2 1/2024 Dinh
11,890,046 B2 2/2024 Neal et al.
11,950,835 B2 4/2024 O'Brien et al.
11,954,887 B2 4/2024 Blau
11,957,405 B2 4/2024 Pearson
11,986,196 B2 5/2024 Wallace et al.
11,986,382 B2 5/2024 Merritt et al.
11,992,643 B2 5/2024 Lee et al.
11,998,223 B2 6/2024 Brady et al.
12,002,065 B2 6/2024 Look et al.
12,004,731 B2 6/2024 Duffy et al.
12,011,186 B2 6/2024 Stefanov
12,016,580 B2 6/2024 Quick et al.
12,023,057 B2 7/2024 Hauser
12,023,058 B2 7/2024 Casey
12,029,442 B2 7/2024 O'Malley
12,032,735 B2 7/2024 Rubin et al.
12,042,160 B2 7/2024 Yang et al.
12,048,446 B2 7/2024 Dwivedi et al.
12,053,685 B2 8/2024 Lockhart et al.
12,064,130 B2 8/2024 O'Malley et al.
12,076,037 B2 9/2024 Brady et al.
12,080,020 B2 9/2024 Blau
12,096,938 B2 9/2024 Hettel et al.
12,096,951 B2 9/2024 Barry et al.
12,097,345 B2 9/2024 Schultz et al.
12,133,657 B2 11/2024 Vale et al.
12,144,515 B2 11/2024 Nagireiter et al.
12,150,659 B2 11/2024 Look et al.
12,156,665 B2 12/2024 Look et al.
12,156,666 B2 12/2024 Trosper et al.
12,156,667 B2 12/2024 Trosper et al.
12,171,449 B2 12/2024 Lee
12,184,353 B2 12/2024 Collins
12,186,064 B2 1/2025 Strasser et al.
12,198,330 B2 1/2025 Blau
12,201,506 B2 1/2025 Buck et al.
12,213,691 B2 2/2025 Whelan
12,214,189 B2 2/2025 Lorenzo et al.
12,220,138 B2 2/2025 Whelan
12,246,141 B2 3/2025 Saadat et al.
12,251,119 B2 3/2025 Naglreiter et al.
12,274,834 B2 4/2025 Saadat et al.
12,305,990 B2 5/2025 Collins
D1,077,996 S 6/2025 Yang et al.
12,343,479 B2 7/2025 Yang et al.
12,343,486 B2 7/2025 Casey et al.
12,349,935 B1 7/2025 Pons
12,350,443 B2 7/2025 Yee et al.
12,364,503 B2 7/2025 Pons
12,369,940 B2 7/2025 Jenson et al.
12,376,904 B1 8/2025 Stern et al.
12,376,928 B2 8/2025 Lau et al.
12,402,902 B2 9/2025 Vale et al.
12,414,784 B1 9/2025 Li et al.
12,419,703 B2 9/2025 O'Malley et al.
12,440,230 B2 10/2025 Gamba et al.
12,446,908 B2 10/2025 Dwivedi et al.
12,447,319 B2 10/2025 Connolly
12,453,564 B2 10/2025 Buck et al.
12,462,425 B2 11/2025 Blau
12,465,383 B2 11/2025 Casey et al.
12,465,393 B1 11/2025 Pons
12,468,215 B2 11/2025 Rosenthal et al.
12,471,941 B2 11/2025 Brady et al.
12,478,390 B2 11/2025 Janardhan et al.
12,502,185 B2 12/2025 Teigen et al.
12,521,132 B2 1/2026 Teigen et al.
12,521,134 B2 1/2026 Gilvarry et al.
12,521,479 B2 1/2026 Casey et al.
12,539,127 B2 2/2026 Look et al.
12,539,130 B2 2/2026 Casey et al.
12,558,175 B2 2/2026 Lau et al.
12,564,458 B2 3/2026 Yang et al.
12,642,950 B2 6/2026 Verma et al.
12,653,555 B2 6/2026 Look et al.
12,667,695 B2 6/2026 Saadat et al.
2002/0058904 A1 5/2002 Boock et al.
2002/0111579 A1 8/2002 Moutafis et al.
2002/0123761 A1 9/2002 Barbut et al.
2002/0132076 A1 9/2002 Stevens
2003/0065250 A1 4/2003 Chiel et al.
2003/0104073 A1 6/2003 Johansson et al.
2003/0199865 A1 10/2003 Knudson et al.
2003/0236517 A1 12/2003 Appling
2004/0097880 A1 5/2004 Schur
2005/0027262 A1 2/2005 Appling et al.
2005/0131343 A1 6/2005 Abrams et al.
2005/0143687 A1 6/2005 Rosenblatt et al.
2005/0165364 A1 7/2005 DiMatteo et al.
2005/0171510 A1 8/2005 DiCarlo et al.
2005/0245894 A1 11/2005 Zadno-Azizi et al.
2006/0041304 A1 2/2006 Jang et al.

(56) References Cited

U.S. PATENT DOCUMENTS

2006/0184141 A1 8/2006 Smith et al.
2006/0270974 A1 11/2006 Goff et al.
2006/0282119 A1 12/2006 Perchik
2006/0293725 A1 12/2006 Rubinsky et al.
2006/0293730 A1 12/2006 Rubinsky et al.
2006/0293731 A1 12/2006 Rubinsky et al.
2007/0021685 A1 1/2007 Oepen et al.
2007/0037132 A1 2/2007 Sukavaneshvar et al.
2007/0078391 A1 4/2007 Wortley et al.
2007/0106162 A1 5/2007 Illyes et al.
2007/0156135 A1 7/2007 Rubinsky et al.
2007/0173786 A1 7/2007 Recinella et al.
2007/0191825 A1 8/2007 Cronin et al.
2007/0198035 A1 8/2007 Threlkeld
2007/0282303 A1 12/2007 Nash et al.
2008/0114308 A1 5/2008 di Palma et al.
2008/0132884 A1 6/2008 Rubinsky et al.
2008/0132885 A1 6/2008 Rubinsky et al.
2008/0154186 A1 6/2008 Appling et al.
2008/0167649 A1 7/2008 Edwards et al.
2008/0167678 A1 7/2008 Morsi
2008/0172080 A1 7/2008 Isham
2008/0183202 A1 7/2008 Isham
2008/0208180 A1 8/2008 Cartier et al.
2008/0208236 A1 8/2008 Hobbs et al.
2008/0269774 A1 10/2008 Garcia et al.
2008/0287939 A1 11/2008 Appling et al.
2008/0294188 A1 11/2008 Appling et al.
2008/0300619 A1 12/2008 Isham
2008/0306499 A1 12/2008 Katoh et al.
2009/0005747 A1 1/2009 Michaels et al.
2009/0024190 A1 1/2009 Irvine
2009/0038752 A1 2/2009 Weng et al.
2009/0048577 A1 2/2009 Gillies et al.
2009/0076585 A1 3/2009 Hendriksen et al.
2009/0118683 A1 5/2009 Hanson et al.
2009/0131924 A1 5/2009 Meyer et al.
2009/0163926 A1 6/2009 Sos
2009/0171267 A1 7/2009 Bonnette et al.
2009/0221899 A1 9/2009 Isham
2009/0259220 A1 10/2009 Appling et al.
2009/0281477 A1 11/2009 Mikus et al.
2009/0306606 A1 12/2009 Lancette et al.
2009/0306625 A1 12/2009 Pereira-Kamath et al.
2009/0314724 A1 12/2009 Nierich
2010/0004623 A1 1/2010 Hamilton et al.
2010/0022947 A1 1/2010 Hassidov et al.
2010/0076302 A1 3/2010 Gray et al.
2010/0094201 A1 4/2010 Mallaby
2010/0114063 A1 5/2010 Recinella et al.
2010/0152725 A1 6/2010 Pearson et al.
2010/0168642 A1 7/2010 Appling et al.
2010/0204712 A1 8/2010 Mallaby
2010/0249505 A1 9/2010 Shoham et al.
2010/0249771 A1 9/2010 Pearson et al.
2010/0249815 A1 9/2010 Jantzen et al.
2010/0250209 A1 9/2010 Pearson et al.
2010/0256487 A1 10/2010 Hawkins et al.
2010/0256546 A1 10/2010 Davis et al.
2010/0256630 A1 10/2010 Hamilton et al.
2011/0004295 A1 1/2011 Wittens
2011/0034886 A1 2/2011 Elbe et al.
2011/0040321 A1 2/2011 Cartier
2011/0060316 A1 3/2011 DiCarlo
2011/0105823 A1 5/2011 Single et al.
2011/0112527 A1 5/2011 Hamilton et al.
2011/0172644 A1 7/2011 Zanoni et al.
2011/0190734 A1 8/2011 Graffam et al.
2011/0190806 A1 8/2011 Wittens
2011/0213392 A1 9/2011 Aklog et al.
2011/0238057 A1 9/2011 Moss et al.
2011/0288529 A1 11/2011 Fulton
2012/0059210 A1 3/2012 Frassica
2012/0078232 A1 3/2012 Schulting
2012/0101471 A1 4/2012 di Palma et al.
2012/0172655 A1 7/2012 Campbell et al.
2012/0178986 A1 7/2012 Campbell et al.
2012/0184942 A1 7/2012 Lareau
2012/0193255 A1 8/2012 Lareau et al.
2012/0226271 A1 9/2012 Callas et al.
2012/0310230 A1 12/2012 Willis
2013/0131691 A1 5/2013 Kozak et al.
2013/0150811 A1 6/2013 Horgan
2013/0190602 A1 7/2013 Liao et al.
2013/0304082 A1 11/2013 Aklog et al.
2013/0310845 A1 11/2013 Thor et al.
2013/0324943 A1 12/2013 Weaver et al.
2013/0338608 A1 12/2013 Moorehead et al.
2014/0005699 A1* 1/2014 Bonnette ........ A61B 17/320758 606/159
2014/0042154 A1 2/2014 Cronin
2014/0074049 A1 3/2014 Veldhuijzen et al.
2014/0142617 A1 5/2014 Larsen
2014/0228869 A1 8/2014 Bonnette et al.
2014/0303658 A1 10/2014 Bonnette et al.
2014/0358060 A1 12/2014 Laster
2014/0364896 A1 12/2014 Consigny
2014/0377738 A1 12/2014 Bachmann et al.
2015/0057648 A1 2/2015 Swift et al.
2015/0068941 A1 3/2015 Caron
2015/0150589 A1 6/2015 Yamanouchi
2015/0190615 A1 7/2015 Shaltis
2015/0230810 A1 8/2015 Creighton et al.
2015/0272622 A1 10/2015 Carson et al.
2015/0305810 A1 10/2015 McElwee et al.
2015/0313732 A1 11/2015 Fulton, III
2015/0320488 A1 11/2015 Moshe et al.
2015/0359547 A1 12/2015 Vale et al.
2016/0022371 A1 1/2016 Sauer et al.
2016/0030708 A1 2/2016 Casiello et al.
2016/0038174 A1 2/2016 Bruzzi et al.
2016/0058493 A1 3/2016 Neal et al.
2016/0106501 A1 4/2016 Appling
2016/0114128 A1 4/2016 Lancette
2016/0114129 A1 4/2016 Lancette
2016/0135712 A1 5/2016 Holochwost et al.
2016/0135829 A1 5/2016 Holochwost et al.
2016/0235974 A1 8/2016 Holochwost et al.
2016/0262777 A1 9/2016 Stigall et al.
2016/0271321 A1 9/2016 Chambers et al.
2016/0279393 A1 9/2016 Anderson et al.
2016/0296747 A1 10/2016 Glenn et al.
2016/0317797 A1 11/2016 Smith et al.
2016/0346472 A1 12/2016 Mitchell et al.
2017/0035445 A1 2/2017 Nguyen et al.
2017/0039711 A1 2/2017 Dincer et al.
2017/0136158 A1 5/2017 Culhane et al.
2017/0172603 A1* 6/2017 Bonnette ............. A61M 25/007
2017/0215890 A1 8/2017 Trujman et al.
2017/0231655 A1 8/2017 Aljuri et al.
2017/0303939 A1 10/2017 Greenhalgh et al.
2017/0303949 A1 10/2017 Ribo Jacobi et al.
2017/0333060 A1 11/2017 Panian
2017/0333076 A1 11/2017 Bruzzi et al.
2018/0064526 A1 3/2018 Walzman
2018/0071014 A1 3/2018 Neal et al.
2018/0071492 A1 3/2018 Laby et al.
2018/0098782 A1 4/2018 Farago
2018/0103974 A1 4/2018 Osborne et al.
2018/0116710 A1 5/2018 Pearson
2018/0207397 A1 7/2018 Look et al.
2018/0272050 A1 9/2018 Laureau et al.
2018/0291882 A1 10/2018 Algawi et al.
2018/0317899 A1 11/2018 Zada
2018/0344987 A1 12/2018 Lancette et al.
2019/0008550 A1 1/2019 Yamanouchi
2019/0021856 A1 1/2019 High
2019/0029791 A1 1/2019 Walzman
2019/0030319 A1 1/2019 Raines
2019/0038300 A1 2/2019 Savastano et al.
2019/0054284 A1 2/2019 Smith et al.
2019/0059840 A1 2/2019 Fouras et al.
2019/0076623 A1 3/2019 Mackay et al.
2019/0083169 A1 3/2019 Single et al.

(56) References Cited

U.S. PATENT DOCUMENTS

2019/0143085 A1 5/2019 Isham
2019/0167287 A1 6/2019 Vale et al.
2019/0175939 A1 6/2019 Isham et al.
2019/0217058 A1 7/2019 Swift
2019/0262031 A1 8/2019 Efremkin
2019/0290323 A1 9/2019 Chun et al.
2019/0321656 A1 10/2019 Isham et al.
2019/0365248 A1 12/2019 Mueller et al.
2019/0365395 A1 12/2019 Tran et al.
2019/0365464 A1 12/2019 Govari et al.
2020/0022712 A1 1/2020 Deville et al.
2020/0030501 A1 1/2020 Minskoff
2020/0038042 A1 2/2020 Al-Shraideh
2020/0038057 A1 2/2020 Rai et al.
2020/0054864 A1 2/2020 Vrancken Peeters et al.
2020/0085453 A1 3/2020 Porter et al.
2020/0101326 A1 4/2020 Zeringue
2020/0107843 A1 4/2020 Goertz et al.
2020/0164117 A1 5/2020 Culhane et al.
2020/0237981 A1 7/2020 Tuval et al.
2020/0246014 A1 8/2020 Walzman
2020/0253670 A1 8/2020 Doisneau et al.
2020/0261266 A1 8/2020 Bley et al.
2020/0276415 A1 9/2020 Tang et al.
2020/0281611 A1 9/2020 Kelly et al.
2020/0289722 A1 9/2020 Culbert et al.
2020/0320775 A1 10/2020 Holladay et al.
2020/0352286 A1 11/2020 Galindo et al.
2020/0367917 A1 11/2020 Teigen et al.
2020/0397959 A1 12/2020 Douglas et al.
2021/0001090 A1 1/2021 Tran et al.
2021/0008354 A1 1/2021 Bhamanyar
2021/0068854 A1 3/2021 Wallace
2021/0069468 A1 3/2021 Keating et al.
2021/0085931 A1 3/2021 Green et al.
2021/0106346 A1 4/2021 Wallace et al.
2021/0121188 A1 4/2021 Yurek
2021/0128182 A1 5/2021 Teigen et al.
2021/0128893 A1 5/2021 Twomey et al.
2021/0138194 A1 5/2021 Garrison et al.
2021/0145445 A9 5/2021 Goldsmith
2021/0153884 A1 5/2021 Casey et al.
2021/0154433 A1 5/2021 Casey et al.
2021/0186537 A1 6/2021 Buck et al.
2021/0186541 A1 6/2021 Thress
2021/0186547 A1 6/2021 Kassab et al.
2021/0196292 A1 7/2021 Vale
2021/0220006 A1 7/2021 Mitchell
2021/0236257 A1* 8/2021 Walzman ......... A61B 17/32037
2021/0244698 A1 8/2021 Kalergis et al.
2021/0252274 A1 8/2021 Dhaliwal et al.
2021/0298773 A1 9/2021 Echarri et al.
2021/0315639 A1 10/2021 Manucherhabadi et al.
2021/0346040 A1 11/2021 Panian
2021/0361314 A1 11/2021 Teigen et al.
2021/0378694 A1 12/2021 Thress et al.
2021/0393277 A1 12/2021 Vale et al.
2022/0000500 A1 1/2022 Arad Hadar et al.
2022/0008022 A1 1/2022 Raman et al.
2022/0039815 A1 2/2022 Thress et al.
2022/0054151 A1 2/2022 Shifflette
2022/0061870 A1 3/2022 Mintz
2022/0061872 A1 3/2022 Mintz
2022/0105333 A1 4/2022 Bourne et al.
2022/0110634 A1 4/2022 Watanabe
2022/0125450 A1 4/2022 Sirhan et al.
2022/0142638 A1 5/2022 Enright et al.
2022/0151647 A1 5/2022 Dolendo et al.
2022/0152355 A1 5/2022 Dolendo et al.
2022/0168000 A1 6/2022 Naglreiter et al.
2022/0175404 A1 6/2022 Mintz et al.
2022/0183646 A1 6/2022 Fouras et al.
2022/0193373 A1 6/2022 Clark et al.
2022/0202506 A1 6/2022 Sganga et al.
2022/0218206 A1 7/2022 Petroff et al.
2022/0249151 A1 8/2022 Forrest et al.
2022/0257268 A1 8/2022 Culbert et al.
2022/0287729 A1 9/2022 Phillips et al.
2023/0030606 A1 2/2023 Swift et al.
2023/0088977 A1 3/2023 Fischell et al.
2023/0148876 A1 5/2023 Robinson et al.
2023/0149035 A1 5/2023 Sirhan et al.
2023/0149073 A1 5/2023 Forrest et al.
2023/0218310 A1 7/2023 Scheinblum et al.
2023/0241302 A1 8/2023 Merritt et al.
2023/0248380 A1 8/2023 Long et al.
2023/0285081 A1 9/2023 Wagner et al.
2023/0301673 A1 9/2023 Park et al.
2023/0310751 A1 10/2023 Merritt et al.
2023/0329777 A1 10/2023 Single et al.
2023/0346416 A1 11/2023 Berrada et al.
2023/0355938 A1 11/2023 Merritt et al.
2023/0364319 A1 11/2023 Vale et al.
2023/0389932 A1 12/2023 Ozenne et al.
2024/0000469 A1 1/2024 Teigen et al.
2024/0024029 A1 1/2024 Kopel et al.
2024/0074804 A1 3/2024 Neal et al.
2024/0138903 A1 5/2024 Pearson
2024/0156473 A1 5/2024 Aklog et al.
2024/0164804 A1 5/2024 Jenson et al.
2024/0164805 A1 5/2024 Jenson et al.
2024/0173042 A1 5/2024 Yang et al.
2024/0173063 A1 5/2024 Neal, II et al.
2024/0188972 A1 6/2024 Vale et al.
2024/0189544 A1 6/2024 Casey et al.
2024/0197347 A1 6/2024 Saadat et al.
2024/0197349 A1 6/2024 Kelly et al.
2024/0197416 A1 6/2024 Gonzalez et al.
2024/0197978 A1 6/2024 Yee
2024/0198060 A1 6/2024 Casey et al.
2024/0198072 A1 6/2024 Merritt et al.
2024/0216600 A1 7/2024 Lenihan et al.
2024/0245417 A1 7/2024 Baron et al.
2024/0245424 A1 7/2024 Casey et al.
2024/0261492 A1 8/2024 Yang et al.
2024/0268844 A1 8/2024 Casey et al.
2024/0277308 A1 8/2024 Min et al.
2024/0285846 A1 8/2024 Su et al.
2024/0299707 A1 9/2024 Humbert et al.
2024/0307659 A1 9/2024 Saadat et al.
2024/0341785 A1 10/2024 Trosper et al.
2024/0341786 A1 10/2024 Trosper et al.
2024/0382223 A1 11/2024 Gilvarry et al.
2025/0064322 A1 2/2025 Vale et al.
2025/0152189 A1 5/2025 Janardhan et al.
2025/0160859 A1 5/2025 Janardhan et al.
2025/0169834 A1 5/2025 Janardhan et al.
2025/0177692 A1 6/2025 Yee et al.
2025/0195245 A1 6/2025 Lee et al.
2025/0235221 A1 7/2025 Janardhan et al.
2025/0255626 A1 8/2025 Childs et al.
2025/0281116 A1 9/2025 Strasser et al.
2025/0325290 A1 10/2025 Brady et al.
2025/0352225 A1 11/2025 Naglreiter et al.
2025/0359883 A1 11/2025 Kelly et al.
2026/0000863 A1 1/2026 Casey et al.
2026/0007424 A1 1/2026 Brady et al.
2026/0007425 A1 1/2026 Connolly
2026/0026824 A1 1/2026 Childs et al.
2026/0174449 A1 6/2026 Deville et al.

FOREIGN PATENT DOCUMENTS

CN 105559854 A 5/2016
CN 110025834 A 7/2019
CN 211068270 U 7/2020
CN 111481262 A 8/2020
CN 111528983 A 8/2020
CN 112258514 B 11/2021
DE 4018736 A1 1/1992
EP 1013287 A2 6/2000
EP 3500191 B1 9/2020
EP 3335647 B1 1/2022
JP H0197951 A 4/1989

(56) References Cited

FOREIGN PATENT DOCUMENTS

| | | | |
|---|---|---|---|
| JP | 2007117384 | A | 5/2007 |
| JP | 2009518134 | A | 5/2009 |
| JP | 2010505542 | A | 2/2010 |
| JP | 2010506653 | A | 3/2010 |
| JP | 2013154171 | A | 8/2013 |
| WO | WO89/05665 | A2 | 6/1989 |
| WO | WO94/016706 | A1 | 8/1994 |
| WO | WO2000/006224 | A1 | 2/2000 |
| WO | WO02/26289 | A1 | 4/2002 |
| WO | WO2003/084596 | A1 | 10/2003 |
| WO | WO2003/092537 | A2 | 11/2003 |
| WO | WO2004/000099 | A2 | 12/2003 |
| WO | WO2004/004546 | A2 | 1/2004 |
| WO | WO2004/043220 | A2 | 5/2004 |
| WO | WO2004/050144 | A2 | 6/2004 |
| WO | WO2004/093941 | A2 | 11/2004 |
| WO | WO2006/012242 | A2 | 2/2006 |
| WO | WO2006/012243 | A2 | 2/2006 |
| WO | WO2006/012244 | A2 | 2/2006 |
| WO | WO2006/086516 | A2 | 8/2006 |
| WO | WO2007/017876 | A2 | 2/2007 |
| WO | WO2007/041471 | A2 | 4/2007 |
| WO | WO2007/085025 | A2 | 7/2007 |
| WO | WO2008/124790 | A2 | 10/2008 |
| WO | WO2008/147760 | A1 | 12/2008 |
| WO | WO2009/035582 | A1 | 3/2009 |
| WO | WO2009/046439 | A2 | 4/2009 |
| WO | WO2009/062105 | A2 | 5/2009 |
| WO | WO2009/114826 | A2 | 9/2009 |
| WO | WO2009/131583 | A1 | 10/2009 |
| WO | WO2009/137800 | A2 | 11/2009 |
| WO | WO2009/155526 | A2 | 12/2009 |
| WO | WO2010/008834 | A2 | 1/2010 |
| WO | WO2010/085765 | A2 | 7/2010 |
| WO | WO2010/093692 | A2 | 8/2010 |
| WO | WO2010/117806 | A1 | 10/2010 |
| WO | WO2010/138919 | A2 | 12/2010 |
| WO | WO2011/022674 | A2 | 2/2011 |
| WO | WO2011/103096 | A2 | 8/2011 |
| WO | WO2011/103133 | A2 | 8/2011 |
| WO | WO2012/051433 | A2 | 4/2012 |
| WO | WO2013/119662 | A1 | 8/2013 |
| WO | WO2014/047626 | A2 | 3/2014 |
| WO | WO2015/196156 | A1 | 12/2015 |
| WO | WO2016/164930 | A1 | 10/2016 |
| WO | WO2017/070702 | A1 | 4/2017 |
| WO | WO2017/106877 | A1 | 6/2017 |
| WO | WO2017/161204 | A1 | 9/2017 |
| WO | WO2018/033401 | A1 | 2/2018 |
| WO | WO2018/080590 | A1 | 5/2018 |
| WO | WO2018/094050 | A2 | 5/2018 |
| WO | WO2019/050765 | A1 | 3/2019 |
| WO | WO2020/036809 | A1 | 2/2020 |
| WO | WO2020/181278 | A1 | 9/2020 |
| WO | WO2020/206366 | A1 | 10/2020 |
| WO | WO2021/076954 | A1 | 4/2021 |
| WO | WO2021/127202 | A1 | 6/2021 |
| WO | WO2021/178696 | A1 | 9/2021 |
| WO | WO20212/48042 | A1 | 12/2021 |
| WO | WO2022/032173 | A1 | 2/2022 |
| WO | WO2022/103848 | A1 | 5/2022 |
| WO | WO2022/109021 | A1 | 5/2022 |
| WO | WO2022/109034 | A1 | 5/2022 |
| WO | WO2022/120270 | A1 | 6/2022 |
| WO | WO2022/251678 | A1 | 12/2022 |
| WO | WO2023/288268 | A1 | 1/2023 |
| WO | WO2023/035013 | A1 | 3/2023 |
| WO | WO2023/049802 | A1 | 3/2023 |
| WO | WO2023/137341 | A1 | 7/2023 |
| WO | WO2023/147353 | A1 | 8/2023 |
| WO | WO2023/150730 | A2 | 8/2023 |
| WO | WO2023/154612 | A2 | 8/2023 |
| WO | WO2023/168415 | A1 | 9/2023 |
| WO | WO2023/178212 | A2 | 9/2023 |
| WO | WO2023/192925 | A2 | 10/2023 |
| WO | WO2023/215779 | A2 | 11/2023 |
| WO | WO2023/220633 | A2 | 11/2023 |
| WO | WO2023/225676 | A2 | 11/2023 |
| WO | WO2023/230608 | A2 | 11/2023 |
| WO | WO2023/239706 | A2 | 12/2023 |

OTHER PUBLICATIONS

Al-Jadda et al.; U.S. Appl. No. 19/106,171 entitled "Thrombus removal systems and associated methods," filed Feb. 24, 2025.

Al-Jadda et al.; U.S. Appl. No. 19/106,174 entitled "Contrast injection and visualization systems and methods for thrombus removal device," filed Feb. 24, 2025.

Gunning; U.S. Appl. No. 19/106,179 entitled "Thrombus removal systems and associated methods," filed Feb. 24, 2025.

Srivathsa et al.; U.S. Appl. No. 19/123,721 entitled "Clot visualization and workflows utilizing real-time imaging for thrombus removal systems and methods," filed Apr. 23, 2025.

Al-Jadda et al.; U.S. Appl. No. 19/123,732 entitled "Thrombus removal systems and methods for blood return and reconstituting removed blood clots," filed Apr. 23, 2025.

Gunning et al.; U.S. Appl. No. 19/123,712 entitled "Thrombus removal systems and associated methods," filed Apr. 23, 2025.

Al-Jadda et al.; U.S. Appl. No. 19/123,691 entitled "Thrombectomy system and method of removing thrombus," filed Apr. 23, 2025.

Al-Jadda et al.; U.S. Appl. No. 19/123,734 entitled "Thrombectomy system and method of removing thrombus," filed Apr. 23, 2025.

Illindala.; U.S. Appl. No. 18/773,208 enttitled "Thrombus removal systems and associated methods," filed Jul. 15, 2024.

Gunning et al.; U.S. Appl. No. 18/835,686 entitled "Thrombus removal systems and associated methods," filed Aug. 2, 2024.

Saul; U.S. Appl. No. 18/867,656 entitled "Thrombus removal systems and associated methods," filed Nov. 20, 2024.

Salahieh et al.; U.S. Appl. No. 18/688,941 entitled "Thrombus removal systems and associated methods," filed Mar. 4, 2024.

Anenberg et al.; Optogenetic stimulation of GABA neurons can decrease local neuronal activity while increasing cortical blood flow; Journal of Cerebral Blood Flow & Metabolism; 35(10); pp. 1579-1586; Oct. 2015.

Eucker et al.; Phase plane analysis of left ventricular hemodynamics; Journal of Applied Physiology; 90(6); pp. 2238-2244; Jun. 1, 2001.

Kondo et al.; Pulmonary hypertension: diagnosis, management, and treatment; Nagoya journal of medical science; 81(1); pp. 19-30; Feb. 2019.

Gunning et al.; U.S. Appl. No. 18/847,594 entitled "Thrombus removal systems and associated methods," filed Sep. 16, 2024.

Al-Jadda et al.; U.S. Appl. No. 18//864,484 entitled "Thrombus removal systems and associated methods," filed Nov. 8, 2024.

Saul; U.S. Appl. No. 18/686,616 entitled "Thrombus removal systems and associated methods," filed Nov. 22, 2024.

Chen et al.; Formation of nanocrystalline AZ31B Mg alloys via cryogenic rotary swaging; Journal of Magnesium and Alloys; 11(5); pp. 1580-1591; May 1, 2023.

Tanyildizi et al.; In vitro testing of a funnel-shaped tip catheter model to decrease clot migration during mechanical thrombectomy; Scientific Reports; 10(1); 7 pages; Jan. 20, 2020.

Al-Jadda et al.; U.S. Appl. No. 18/562,038 entitled "Thrombus removal systems and associated methods," filed Nov. 17, 2023.

Al-Jadda et al.; U.S. Appl. No. 18/568,681 entitled "Thrombus removal systems and associated methods," filed Dec. 8, 2023.

Nicolini et al.; Histological analysis of thrombi retrieved after acute ischemic stroke from large vessel occlusion: from research to clinical practice; Vessel Plus; 2022; 6:2; 17 pages; Jan. 6, 2022.

Al-Jadda et al; U.S. Appl. No. 19/483,840 entitled "Thrombus removal system consoles and associated user interfaces," filed Nov. 12, 2025.

Illindala et al.; U.S. Appl. No. 19/512,638 entitled "Thrombus removal systems and methods," filed Feb. 19, 2026.

(56) References Cited

OTHER PUBLICATIONS

Illindala et al.; U.S. Appl. No. 19/514,320 entitled Thrombus removal systems and methods, filed Feb. 25, 2026.

* cited by examiner

Section E-E

Section E-E

Section E-E

Section E-E

Section E-E

Section E-E

| | Source (Vac P or Jet P) | Prox Sensor(s) | Distal Sensor(s) | System State |
|---|---|---|---|---|
| | - | - | - | Searching for clot/no clot engaged |
| | + | - | + | Engaging clot |
| Sensor Reading | + | + | + | Clot engaged |
| | + | + | - | Clogged jet lumen |
| | + | - | - | Clogged aspiration lumen |
| | - | + | + | Clot initially engaged / leak |

(+) : nominal state
(-) : error, non-nominal state

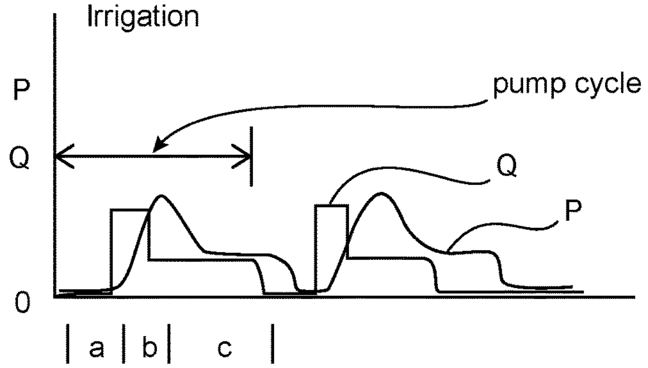
FIG. 17
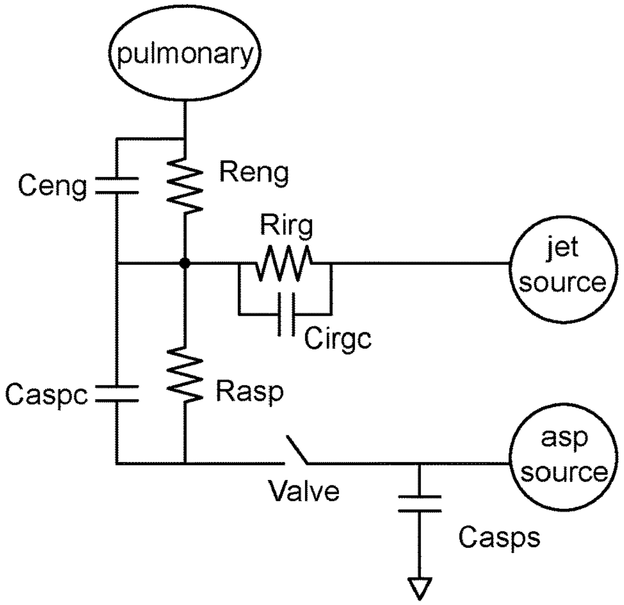
FIG. 18
FIG. 19A
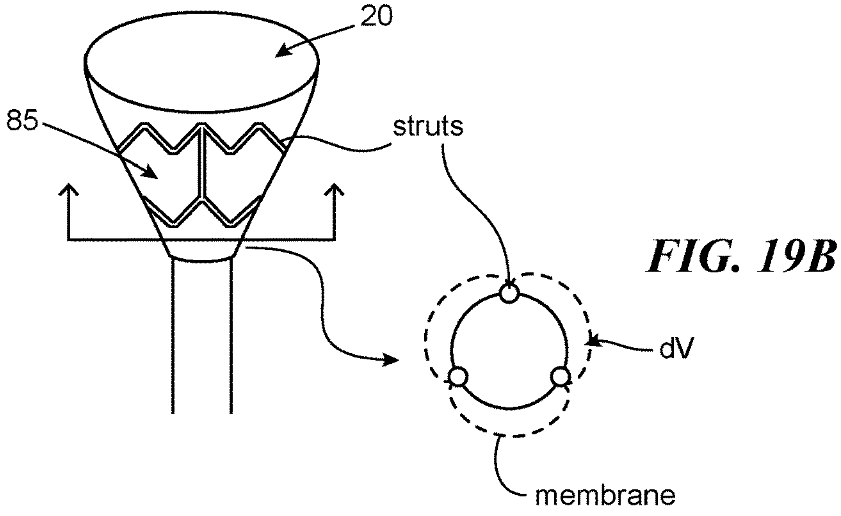
FIG. 19B

THROMBUS REMOVAL SYSTEMS AND ASSOCIATED METHODS

CROSS REFERENCE TO RELATED APPLICATIONS

This application is a 371 of PCT/US2022/033024, filed Jun. 10, 2022, which claims the benefit of priority to U.S. Provisional Application Nos. 63/209,257, filed Jun. 10, 2021, 63/250,089, filed Sep. 29, 2021, 63/285,054, filed Dec. 1, 2021, 63/335,656, filed Apr. 27, 2022, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present technology generally relates to medical devices and, in particular, to systems including aspiration and fluid delivery mechanisms and associated methods for removing a thrombus from a mammalian blood vessel.

BACKGROUND

Thrombotic material may lead to a blockage in fluid flow within the vasculature of a mammal. Such blockages may occur in varied regions within the body, such as within the pulmonary system, peripheral vasculature, deep vasculature, or brain. Pulmonary embolisms typically arise when a thrombus originating from another part of the body (e.g., a vein in the pelvis or leg) becomes dislodged and travels to the lungs. Anticoagulation therapy is the current standard of care for treating pulmonary embolisms, but may not be effective in some patients. Additionally, conventional devices for removing thrombotic material may not be capable of navigating the tortuous vascular anatomy, may not be effective in removing thrombotic material, and/or may lack the ability to provide sensor data or other feedback to the clinician during the thrombectomy procedure. Existing thrombectomy devices operate based on simple aspiration which works sufficiently for certain clots but is largely ineffective for difficult, organized clots. Many patients presenting with deep vein thrombus (DVT) are left untreated as long as the risk of limb ischemia is low. In more urgent cases, they are treated with catheter-directed thrombolysis or lytic therapy to break up a clot over the course of many hours or days. More recently other tools like clot retrievers have been developed to treat DVT and pulmonary embolism (PE), but these tools are not being widely adopted because of their limited effectiveness and additional costs versus aspiration or the standard of case. Other recent developments focus on slicing or macerating the clot, but these mechanisms are designed to reduce the risk of the catheter clogging and do not address the problem of tough, large, organized clots. There remains the need for a device to address these and other problems with existing venous thrombectomy including, but not limited to, a fast, easy-to-use, and effective device for removing a variety of clot morphologies.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 17 illustrates various irrigation pump cycles of a thrombus removal system.

FIG. 18 illustrates a thrombus removal system with a valve near the aspiration source.

FIGS. 19A-19B illustrate a thrombus removal system with a plurality of struts in the funnel.

SUMMARY OF THE DISCLOSURE

Figure 1A:
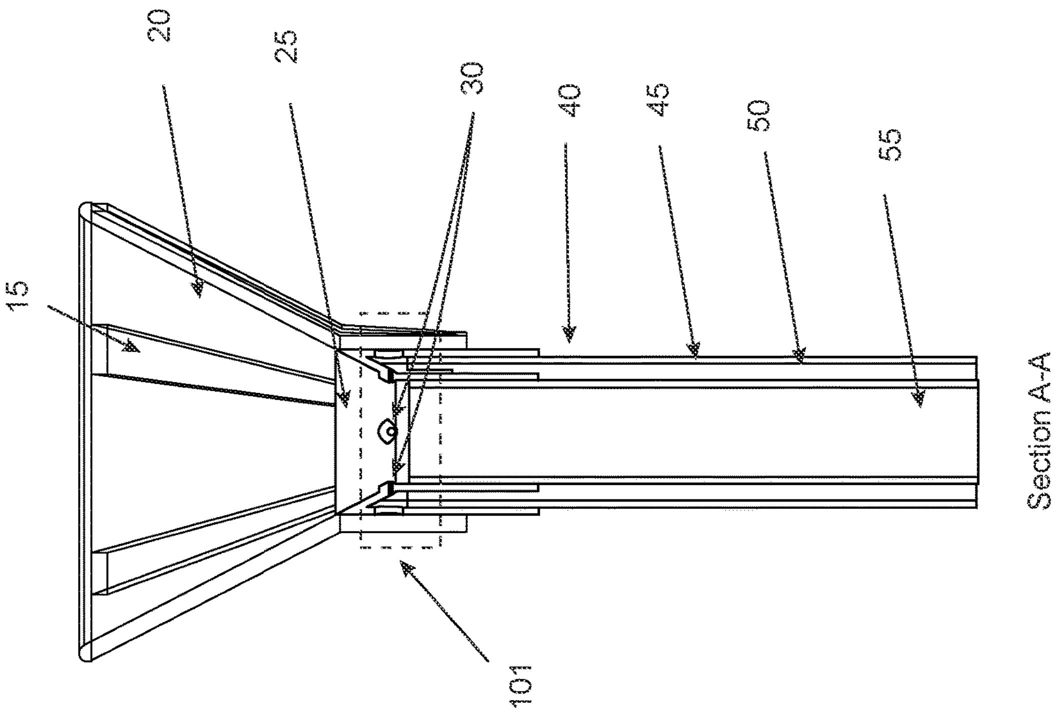
FIGS. 1-1L illustrate various views of a portion of a thrombus removal system including a distal portion of an elongated catheter configured in accordance with an embodiment of the present technology.

A thrombus removal is provided, comprising an elongate shaft comprising a working end, at least one fluid lumen in the elongate shaft, and two or more apertures disposed at or near the working end, the two or more apertures in fluid communication with the least one fluid lumen and configured to generate two or more fluid streams that at least partially collide at an interaction region, the two or more fluid streams having a flow rate sufficient to create cavitation in the interaction region that is configured to mechanically fractionate a target thrombus.

A thrombus removal device is also provided, comprising an elongate shaft comprising a working end, at least one fluid lumen in the elongate shaft, and two or more apertures disposed at or near the working end, the two or more apertures in fluid communication with the least one fluid lumen and configured to generate two or more fluid streams that interact within or near the working end at an interaction region, the two or more fluid streams having a flow rate and proximity sufficient to induce cavitation at the interaction region that is configured to mechanically morcellate a target thrombus.

In some embodiments, the two or more fluid streams each have a flow rate ranging between 50 m/s and 90 m/s.

In other embodiments, the two or more fluid streams each have a flow rate of at least 50 m/s.

In some examples, fluid flowing within the at least one fluid lumen at a lumen flow rate of 3 m/s results in the two or more fluid streams having a flow rate of at least 50 m/s.

In other embodiments, fluid flowing within the at least one fluid lumen at a lumen flow rate of 4 m/s results in the two or more fluid streams having a flow rate of at least 70 m/s.

In some examples, fluid flowing within the at least one fluid lumen at a lumen flow rate of 5 m/s results in the two or more fluid streams having a flow rate of at least 90 m/s.

In one embodiment, the interaction region comprises a focal point of the two or more fluid streams.

In some embodiments, the two or more fluid streams are generally orthogonal to a longitudinal axis of the elongate shaft.

In some examples, the two or more fluids streams are directed distally such that the focal point is distal relative to the two or more apertures.

In one embodiment, the distally directed two or more fluid streams are further configured to generate a cavitation column that extends distally from the focal point.

In some embodiments, the two or more fluids streams are directed proximally such that the focal point is proximal relative to the two or more apertures.

In one embodiment, the proximally directed two or more fluid streams are further configured to generate a cavitation column that extends proximally from the focal point.

In some examples, a cavitation detection sensor is disposed on or within the thrombus removal device.

In some embodiments, the cavitation detection sensor is disposed on or within a funnel at the working end of the thrombus removal device.

In another embodiment, the cavitation detection sensor is disposed on or within an aspiration lumen at the working end of the thrombus removal device.

In some examples, the cavitation detection sensor comprises an ultrasound transducer element.

In other embodiments, the cavitation detection sensor comprises a hydrophone.

In some examples, the cavitation detection sensor comprises a laser.

In other embodiments, the cavitation detection sensor comprises a microphone.

Another embodiment includes a real-time imaging device configured to image the cavitation in real-time. In some embodiments, the real-time imaging device comprises an ultrasound imaging device. In some embodiments, the ultrasound imaging device comprises an external ultrasound imaging probe. In other embodiments, the ultrasound imaging device comprises a catheter-based ultrasound imaging device.

A method for removing a thrombus from a blood vessel of a patient is provided, the method comprising introducing a distal portion of an elongate catheter to a thrombus location in a blood vessel, drawing at least a section of the thrombus into the distal portion, and generating two or more fluid streams having a flow rate of at least 20 m/s that interact at an interaction region to create cavitation within the thrombus.

A method for removing a thrombus from a blood vessel of a patient is also provided, the method comprising introducing a distal portion of an elongate catheter to a thrombus location in a blood vessel, drawing at least a section of the thrombus into the distal portion, and generating two or more fluid streams having a flow rate of at least 50 m/s that interact at an interaction region to create cavitation within the thrombus.

A method for removing a thrombus from a blood vessel of a patient is provided, the method comprising introducing a distal portion of an elongate catheter to a thrombus location in a blood vessel, drawing at least a section of the thrombus into the distal portion, and generating two or more fluid streams that interact within or near the distal portion at an interaction region, wherein the two or more fluid streams are configured to apply at least four distinct breaking forces to the thrombus including: 1) a slicing force as the two or more fluid streams initially cut through the thrombus prior to meeting at the interaction region; 2) a cavitation force at the interaction region when the two or more fluid streams interact to generate cavitation; 3) a shearing force caused by the two or more fluid streams moving against each other to generate shearing cavitation; and 4) a rotational fluid motion force caused by the shearing force and the cavitation force.

In some embodiments, the drawing is by suction applied via an aspiration lumen of the elongate catheter.

In one embodiment, generating the two or more fluid streams further comprises directing the two or more fluid streams proximally relative to fluid stream apertures of the elongate catheter.

In some embodiments, generating the two or more fluid streams further comprises directing the two or more fluid streams distally relative to fluid stream apertures of the elongate catheter.

In one embodiment, generating the two or more fluid streams further comprises directing the two or more fluid streams generally orthogonal to a longitudinal axis of the elongate catheter.

In some examples, only a portion of the two or more fluid streams interact at the interaction region.

In other embodiments, a second portion of the two or more fluid streams that does not interact at the interaction region generates at least one shearing cavitation stream in the thrombus.

In some embodiments, a second portion of the two or more fluid streams that does not interact at the interaction region generates at least one halo cavitation stream in the thrombus.

In one embodiment, the flow rate ranges from 20 m/s to 90 m/s.

In some embodiments, the flow rate ranges from 50 m/s to 90 m/s.

A method for removing a thrombus from a blood vessel of a patient, the method comprising introducing a distal portion of an elongate catheter to a thrombus location in a blood vessel, drawing at least a portion of the thrombus into the distal portion, directing two or more fluid streams into the thrombus to cut or partially cut the thrombus, removing at least a portion of the thrombus from the distal portion, continuing directing the two or more fluid streams into the thrombus until the two or more streams meet and interact with another in an interaction region within the thrombus, maintaining a flow rate of the two or more fluid streams sufficient to generate cavitation in the interaction region, and removing at least a portion of the thrombus from the distal portion.

In some embodiments, the flow rate is at least 20 m/s.

In other embodiments, the flow rate is at least 50 m/s.

In some embodiments, the flow rate is between 20 m/s and 90 m/s.

In some embodiments, the method further includes detecting the cavitation with a cavitation sensor.

In one example, during the directing step, the method includes determining that there is no cavitation.

In some embodiments, the method further comprises indicating to the user that there is no cavitation.

A method for removing a thrombus from a blood vessel of a patient with a thrombus removal device is provided, the method comprising introducing a distal portion of an elongate catheter to a thrombus location in a blood vessel, expanding a funnel of the elongate catheter at the thrombus location, operating an aspiration source of the elongate catheter at a first vacuum level, capturing at least a section of the thrombus into the funnel of the distal portion, determining that at least the section of the thrombus has been captured into the funnel, directing fluid toward the thrombus from at least two different jet ports of the elongate catheter, and operating the aspiration source at a second vacuum level higher than the first vacuum level to remove the thrombus from the patient.

In some embodiments, the drawing is by suction applied via an aspiration lumen of the elongate catheter.

In one embodiment, the fluid has an average velocity of at least 20 meters/second (m/s).

In some embodiments, determining that at least the section of the thrombus has been captured into the funnel further comprises identifying a pressure change associated with a thrombus capture with at least one jet port of the thrombus removal device.

In one example, the pressure change comprises a pressure drop below a pressure threshold.

In another embodiment, the pressure change comprises a rate of change greater than a pressure threshold.

In some embodiments, the pressure change comprises identifying pressure fluctuations that fall below a threshold value.

In some examples, the pressure change comprises a pressure increase above the second vacuum level.

In some embodiments, directing fluid further comprises directing fluid streams that interact with another in an interaction region.

In other embodiments, directing fluid further comprises causing the fluid streams to intersect.

In some examples, fluid streams are orthogonal to a longitudinal axis of the elongate catheter.

In another example, the fluid streams are proximally directed.

In some examples, determining that at least the section of the thrombus has been captured into the funnel further comprises detecting a change in impedance with a sensor positioned at a distal portion of the thrombus removal device.

In another embodiment, the method includes determining when the thrombus has been removed.

A method for removing a thrombus from a blood vessel of a patient with a thrombus removal device is provided, the method comprising introducing a distal portion of an elongate catheter to a thrombus location in a blood vessel, expanding a funnel of the elongate catheter at the thrombus location, operating an aspiration lumen at a first suction level prior to engagement with a thrombus, capturing at least a section of the thrombus into the funnel of the distal portion, determining that at least the section of the thrombus has been captured into the funnel, directing fluid toward the thrombus from at least two different jet ports of the elongate catheter, and operating the aspiration lumen at a second suction level that is higher than the first suction level to remove the thrombus from the patient.

In some embodiments, the method includes determining if the thrombus has been fully removed from the patient.

In another embodiment, the method includes operating the aspiration lumen at the first suction level and stopping directing the fluid.

A method for removing a thrombus from a blood vessel of a patient with a thrombus removal device is provided, the method comprising introducing a distal portion of an elongate catheter to a thrombus location in a blood vessel, expanding a funnel of the elongate catheter at the thrombus location, operating an aspiration source of the elongate catheter, measuring a flow rate of the aspiration source, capturing at least a section of the thrombus into the funnel of the distal portion, determining that at least the section of the thrombus has been captured into the funnel based on the flow rate, directing fluid toward the thrombus from at least two different points along respective fluid paths, and removing the thrombus from the patient with the aspiration source.

In some embodiments, the drawing is by suction applied via an aspiration lumen of the elongate catheter.

In another embodiment, the method includes determining a rate of change of the flow rate.

In some examples, the method includes determining that at least the section of the thrombus has been captured into the funnel when the rate of change is above a predetermined threshold.

In some embodiments, the method further comprises determining that the thrombus is fully captured into the funnel when the flow rate reaches zero.

In one implementation, the method includes indicating to the user that the thrombus is fully captured.

In some embodiments, the directing fluid step is performed only after it is determined that at least a section of the thrombus has been captured into the funnel.

In another embodiment, the method includes directing fluid towards the thrombus a lower flow rate for a first time period.

A thrombus removal device, comprising an elongate catheter, a hemispherical funnel disposed on a distal end of the catheter, an aspiration source coupled to the hemispherical funnel with an aspiration lumen, a plurality of jets disposed within or near the hemispherical funnel, and a fluid source coupled to the plurality of jets and configured to direct fluid toward a common intersection point.

A thrombus removal device is provided, comprising an elongate shaft comprising a working end, an aspiration lumen disposed in the elongate shaft, extending to the working end, and coupled to an aspiration source, at least one fluid lumen in the elongate shaft, two or more apertures disposed at or near the working end, the two or more apertures in fluid communication with the least one fluid lumen and configured to generate two or more fluid streams, at least one aperture disposed in the aspiration lumen and in fluid communication with the at least one fluid lumen, the at least one aperture configured to generate an aspiration fluid stream, and an electronic controller configured to control the aspiration source and to direct a flow of fluid into the at least on fluid lumen.

In some embodiments, the aspiration fluid stream is configured to be directed proximally into the aspiration lumen.

In another implementation, the device includes a valve disposed within the aspiration lumen and being operatively coupled to the electronic controller.

In some embodiments, in a normal operation mode, the electronic controller is configured to open the valve and direct a flow of fluid into the two or more apertures but not the at least one aperture in the aspiration lumen.

In another implementation, in a clog removal mode, the electronic controller is configured to close the valve and direct a flow of fluid into the at least one aperture in the aspiration lumen.

DETAILED DESCRIPTION

This application is related to disclosure in International Application No. PCT/US2021/020915, filed Mar. 4, 2021 (the '915 application), the disclosure of which is incorporated by reference herein for all purposes. The '915 application describes general mechanisms for capturing and removing a clot. By example, the catheter may include a capture element such as an auger to break up and draw in a clot material into an aspiration lumen. In another example, multiple fluid streams are directed toward the clot to fragment the material.

The present technology is generally directed to thrombus removal systems and associated methods. A system configured in accordance with an embodiment of the present technology can include, for example, an elongated catheter having a distal portion configured to be positioned within a blood vessel of the patient, a proximal portion configured to be external to the patient, a fluid delivery mechanism configured to fragment the thrombus with pressurized fluid, an aspiration mechanism configured to aspirate the fragments of the thrombus, and one or more lumens extending at least partially from the proximal portion to the distal portion.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to the figures.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although some embodiments herein are described in terms of thrombus removal, it will be appreciated that the present technology can be used and/or modified to remove other types of emboli that may occlude a blood vessel, such as fat, tissue, or a foreign substance. Additionally, although some embodiments herein are described in the context of thrombus removal from a pulmonary artery (e.g., pulmonary embolectomy), the technology may be applied to removal of thrombi and/or emboli from other portions of the vasculature (e.g., in neurovascular, coronary, or peripheral applications). Moreover, although some embodiments are discussed in terms of maceration of a thrombus with a fluid, the present technology can be adapted for use with other techniques for breaking up a thrombus into smaller fragments or particles (e.g., ultrasonic, mechanical, enzymatic, etc.).

The headings provided herein are for convenience only and do not interpret the scope or meaning of the claimed present technology.

Systems for Thrombus Removal

As provided above, the present technology is generally directed to thrombus removal systems. Such systems include an elongated catheter having a distal portion positionable within a blood vessel of the patient (e.g., an artery or vein), a proximal portion positionable outside the patient's body, a fluid delivery mechanism configured to fragment the thrombus with pressurized fluid, an aspiration mechanism configured to aspirate the fragments of the thrombus, and one or more lumens extending at least partially from the proximal portion to the distal portion. In some embodiments, the systems herein are configured to engage a thrombus in a patient's blood vessel, break the thrombus into small fragments, and aspirate the fragments out of the patient's body. The pressurized fluid streams (e.g., jets) function to cut or macerate thrombus, before, during, and/or after at least a portion of the thrombus has entered the aspiration lumen or a funnel of the system. Fragmentation helps to prevent clogging of the aspiration lumen and allows the thrombus removal system to macerate large, firm clots that otherwise could not be aspirated. As used herein, "thrombus" and "embolism" are used somewhat interchangeably in various respects. It should be appreciated that while the description may refer to removal of "thrombus," this should be understood to encompass removal of thrombus fragments and other emboli as provided herein.

According to embodiments of the present technology, a fluid delivery mechanism can provide a plurality of fluid streams (e.g., jets) to fluid apertures of the thrombus removal system for macerating, cutting, fragmenting, pulverizing and/or urging thrombus to be removed from a proximal portion of the thrombus removal system. The thrombus removal system can include an aspiration lumen extending at least partially from the proximal portion to the distal portion of the thrombus removal system that is adapted for fluid communication with an aspiration pump (e.g., vacuum source). In operation, the aspiration pump may generate a volume of lower pressure within the aspiration lumen near the proximal portion of the thrombus removal system, urging aspiration of thrombus from the distal portion.

Figure 1:
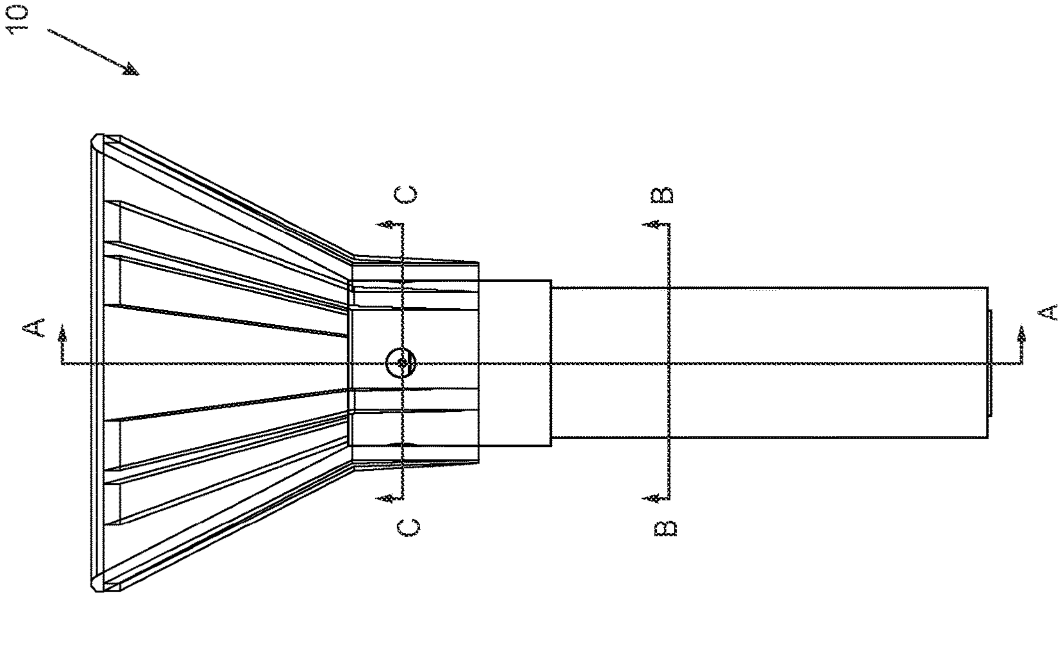

FIG. 1 illustrates a distal portion 10 of a thrombus removal system according to an embodiment of the present technology. FIG. 1A Section A-A illustrates an elevation sectional view of the distal portion. The example section A-A in FIG. 1A depicts a funnel 20 that is positioned at the distal end of the distal portion 10, the funnel adapted to engage with thrombus and/or a tissue (e.g., vessel) wall to aid in thrombus fragmentation and/or removal. The funnel can have a variety of shapes and constructions as would be understood by one of skill from the description herein. The example section A-A in FIG. 1A depicts a double walled thrombus removal device construction having an outer wall/tube 40 and an inner wall/tube 50. An aspiration lumen 55 is formed by the inner wall 50 and is centrally located. A generally annular volume forms at least one fluid lumen 45 between the outer wall 40 and the inner wall 50. The fluid lumen 45 is adapted for fluid communication with the fluid delivery mechanism. One or more apertures (e.g., nozzles, orifices, or ports) 30 are positioned in the thrombus removal system to be in fluid communication with the fluid lumen 45 and an irrigation manifold 25. In operation, the ports 30 are adapted to direct (e.g., pressurized) fluid toward thrombus that is engaged with the distal portion 10 of the thrombus removal system.

In various embodiments, the system can have an average flow velocity within the fluid lumen of up to 20 m/s to achieve consistent and successful aspiration of clots. In some embodiments, the fluid source itself can be delivered in a pulsed sequence or a preprogrammed sequence that includes some combination of pulsatile flow and constant flow to deliver fluid to the jets. In these embodiments, while the average pulsed fluid velocity may be up to 20 m/s, the peak fluid velocity in the lumen may be up to 30 m/s or more during the pulsing of the fluid source. In some embodiments, the jets or apertures are no smaller than 0.0100" or even as small as 0.008" to avoid undesirable spraying of fluid. In some embodiments, the system can have a minimum vacuum or aspiration pressure of 15 inHg, to remove target clots after they have been macerated or broken up with the jets described above.

The thrombus removal system can be sized and configured to access and remove thrombi in various locations or vessels within a patient's body. It should be understood that while the dimensions of the system may vary depending on the target location, generally similar features and components described herein may be implemented in the thrombus removal system regardless of the application. For example, a thrombus removal system configured to remove pulmonary embolism (PE) from a patient may have an outer wall/tube with a size of approximately 11-13 Fr, or preferably 12 Fr, and an inner wall/tube with a size of 7-9 Fr, or preferably 8 Fr. A deep vein thrombosis (DVT) device, on the other hand, may have an outer wall/tube with a size of approximately 9-11 Fr, or preferably 10 Fr, and an inner wall/tube with a size of 6-9 Fr, or preferably 7.5 Fr. Applications are further provided for ischemic stroke and peripheral embolism applications.

Figure 1D:
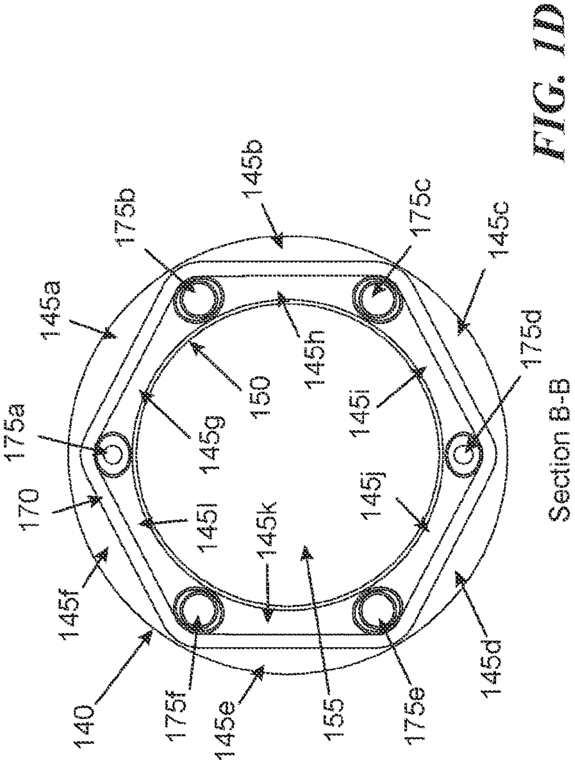
Figure 1E:
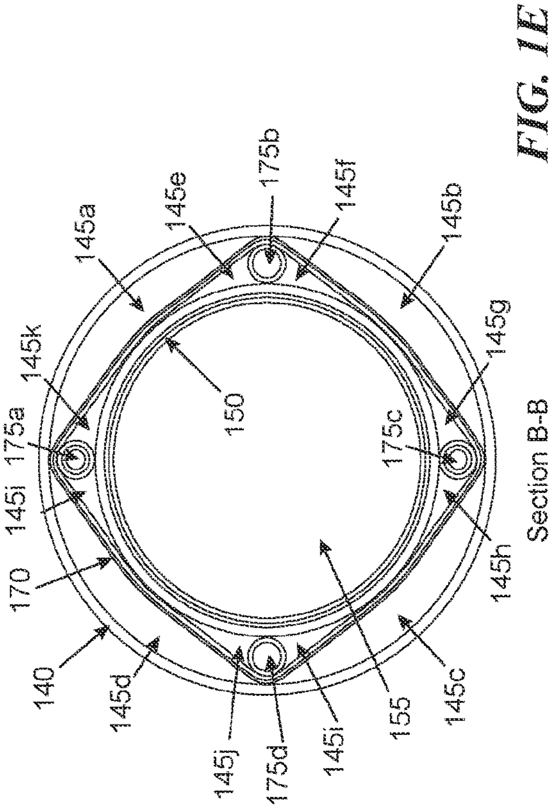
Figure 1B:
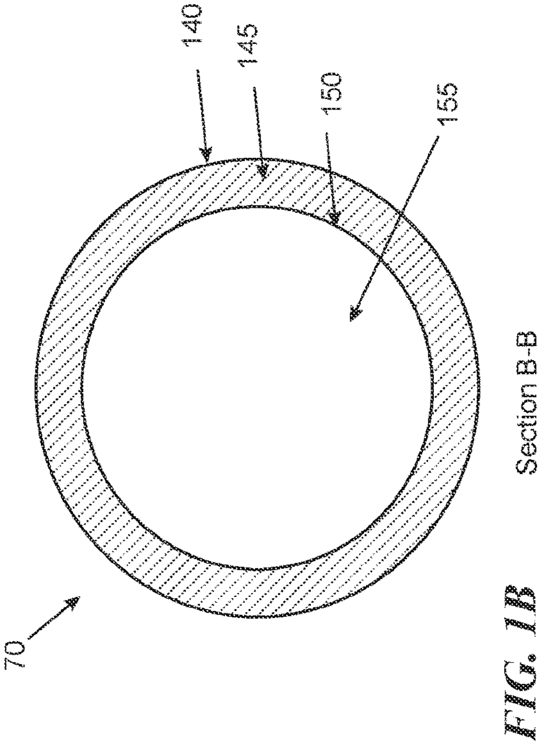
Figure 1C:
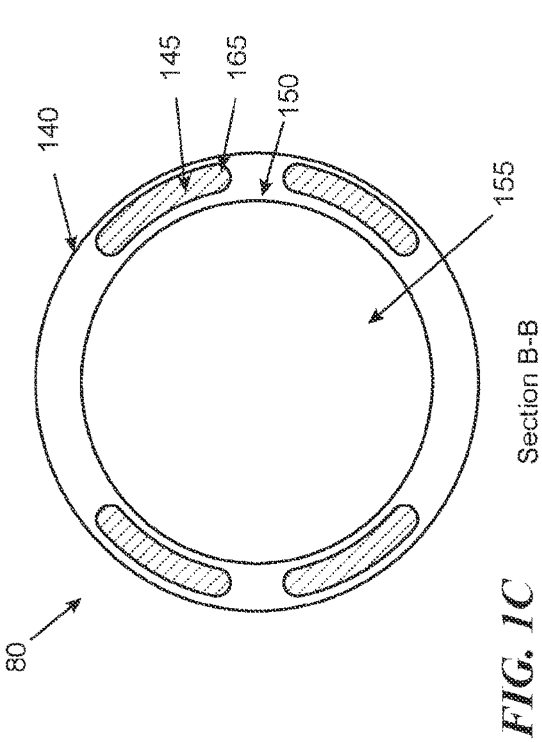

Section B-B of FIG. 1B illustrates in plan view a portion of the thrombus removal system that is proximal to the funnel and irrigation manifold. Section B-B depicts an outer wall 140, an inner wall 150, an aspiration lumen 155 and a fluid lumen 145. In some embodiments, in cross-section the aspiration lumen 155 is generally circular and the fluid lumen 145 is generally annular in shape (e.g., cross-section 70). It will be appreciated that alternative constructions and/or arrangements of the inner wall 150 and the outer wall 140 produce variations in cross-sectional shape of the aspiration and fluid lumens 155 and 145. For example, the inner wall 150 can be shaped to form an aspiration lumen 155 that, in cross-section, is generally oval, circular, rectilinear, square, pentagonal, or hexagonal. The inner and outer walls 150 and 140 can be shaped and arranged to form a fluid lumen 145 that, in cross-section, is generally crescent-shaped, diamond shaped, or irregularly shaped. For example, referring to FIG. 1C Section B-B, the region between the inner wall 150 and the outer wall 140 can include one or more wall structures 165 that form respective fluid lumens 145 (e.g., as in cross-section 80). The wall structures 165 can be formed by lamination between the outer and inner walls 140 and 150, or by a multi-lumen extrusion that forms a plurality of the wall structures.

Section B-B of FIGS. 1D-1H illustrate additional examples of a portion of the thrombus removal system that is proximal to the funnel and irrigation manifold. Similar to the embodiments described above, the portion in these examples can include an outer wall 140, an inner wall 150, and an aspiration lumen 155. Additionally, the illustrated portion of the thrombus removal system can include a middle wall 170 disposed between the outer wall 140 and the inner wall 150. The middle wall 170 enables further segmentation of the annular space between the inner wall and outer wall into a plurality of distinct fluid lumens and/or auxiliary lumens. For example, referring to FIG. 1D, the middle wall can be generally hexagon shaped, and the annular space can include a plurality of fluid lumens 145*a*-141 and a plurality of auxiliary lumens 175*a*-175*f*. As shown in FIG. 1D, the fluid lumens can be formed by some combination of the outer wall 140 and the middle wall 170, or between the middle wall 170, the inner wall 150, and two of the auxiliary lumens. For example, fluid lumen 145*a* is formed in the space between outer wall 140 and middle wall 170. However, fluid lumen 145*g* is formed in the space between middle wall 170, inner wall 150, auxiliary lumen 175*a*, and auxiliary lumen 175*b*. Generally, the fluid lumens are configured to carry a flow of fluid such as saline from a saline source of the system to one or more ports/apertures/orifices of the system. The auxiliary lumens can be configured for a number of functions. In some embodiments, the auxiliary lumens can be coupled to the fluid/saline source and to the apertures to be used as additional fluid lumens. In other embodiments, the auxiliary lumens can be configured as steering ports and can include a guide wire or steering wire within the lumen for steering of the thrombus removal system. Additionally, in other embodiments, the auxiliary lumens can be configured to carry electrical, mechanical, or fluid connections to one or more sensors. For example, the system may include one or more electrical, optical, or fluid based sensors disposed along any length of the system. The sensors can be used during therapy to provide feedback for the system (e.g., sensors can be used to detect clogs to initiate a clog removal protocol, or to determine the proper therapy mode based on sensor feedback such as jet pulse sequences, aspiration sequences, etc.). The auxiliary ports can therefore be used to connect to the sensors, e.g., by electrical connection, optical connection, mechanical/wire connection, and/or fluid connection. It is also contemplated that the fluid and auxiliary lumens can be configured to carry and deliver other fluids, such as thrombolytics or radio-opaque contrast injections to the target tissue site during treatment.

It should be understood that in some embodiments, all the fluid lumens are fluidly connected to all of the jets or apertures of the thrombus removal device. Therefore, when a flow of fluid is delivered from the fluid lumen(s) to the jets, all jets are activated with a jet of fluid at once. However, it should also be understood that in some embodiments, the fluid lumens are separate or distinct, and these distinct fluid lumens may be fluidly coupled to one or more jets but not to all jets of the device. In these embodiments, a subset of the jets can be controlled by delivering fluid only to the fluid lumens that are coupled to that subset of jets. This enables additional functionality in the device, in which specific jets can be activated in a user defined or predetermined order.

In various embodiments, the fluid pressure is generated at the pump (in the console or handle). The fluid is accelerated as it exits the ports at the distal end and is directed to the target clot. In this way a wider variety of cost-effective components can be used to form the catheter while still maintaining a highly-effective device for clot removal. Additional details are provided below.

Figure 1F:
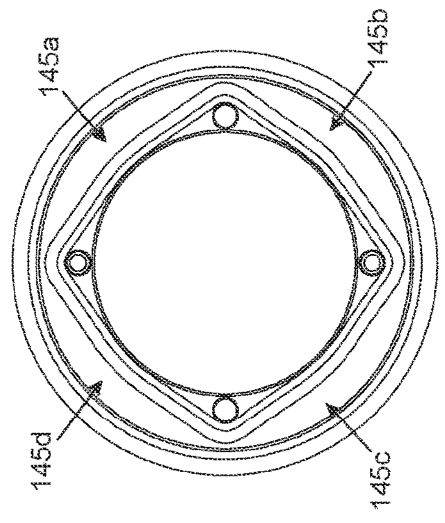

Section B-B of FIG. 1E illustrates another embodiment of the portion of the thrombus removal system that is proximal to the funnel and irrigation manifold. Similar to the embodiment of FIG. 1D, this embodiment also includes a middle wall 170. However, the middle wall in this example is generally square shaped, facilitating the formation of fluid lumens 145*a*-145*k* and auxiliary lumens 175*a*-175*d*. The example illustrated in section B-B of FIG. 1F is similar to that of the embodiment of FIG. 1E, however this embodiment includes only fluid lumens 145*a*-145*d*. The fluid lumens 145*e*-145*k* from the embodiment of FIG. 1E are not used as fluid lumens in this embodiment. They can be, for example, empty lumens, vacuum, filled with an insulative material, and/or filled with a radio-opaque material or any other material that may help visualize the thrombus removal system during therapy. The embodiment 1F includes the same four auxiliary reports as illustrated and described in the embodiment of FIG. 1E.

Figure 1G:
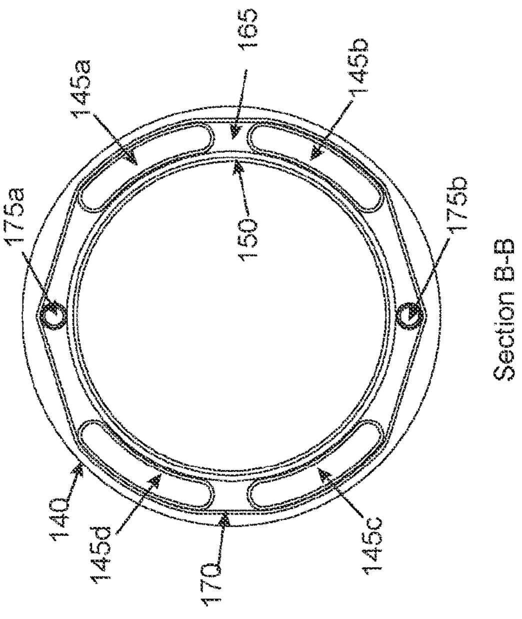

Section B-B of FIG. 1G illustrates another example of a portion of the thrombus removal system that is proximal to the funnel and irrigation manifold. Similar to the embodiments described above, the illustrated portion of the thrombus removal system can include a middle wall 170 disposed between the outer wall 140 and the inner wall 150. However, this embodiment includes four distinct fluid lumens 145*a*-145*d* formed by wall structures 165. As with the embodiment of FIG. 1C, the wall structures 165 can be formed by lamination between the outer and inner walls 140 and 150, or by a multi-lumen extrusion that forms a plurality of the wall structures. As shown, this embodiment can include a pair of auxiliary lumens 175*a* and 175*b*, which can be used, for example, for steering or for sensor connections as described above.

Figure 1H:
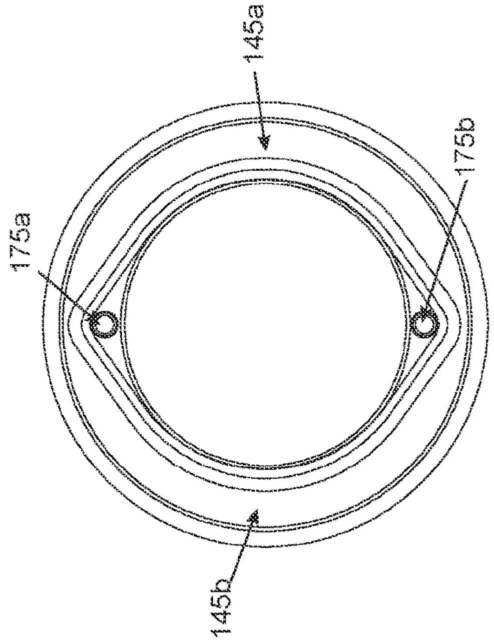
Figure 1I:
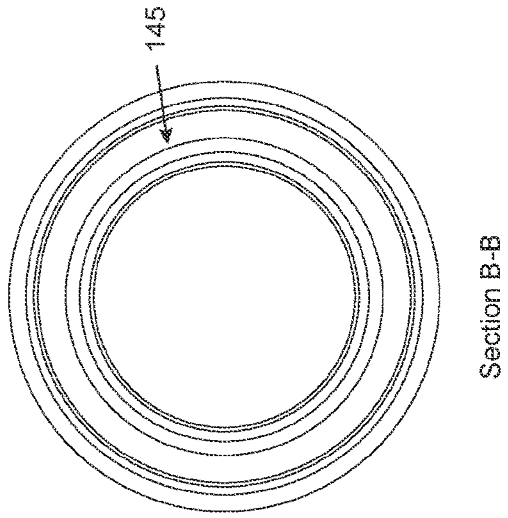

Section B-B of FIG. 1H is another similar embodiment in which the middle wall and outer wall can be used to form fluid lumens 145*a* and 145*b*. Auxiliary lumens 175*a* and 175*b* can be formed in the space between the middle wall and the inner wall. It should be understood that the middle wall can contact the outer wall to create independent fluid lumens 145*a* and 145*b*. However, in other embodiments, it should be understood that the middle wall may not contact the outer wall, which would facilitate a single annular fluid lumen, such as is shown by fluid lumen 145 in Section B-B of FIG. 1I. In another embodiment, as shown in Section B-B of FIG. 1J, the inner wall 150 and the outer wall 140 may not be concentric, which facilitates formation of an annular space and/or fluid lumen 145 that is thicker or wider on one side of the device relative to the other side. As shown in FIG. 1J, a distance between the exemplary outer wall 140 and inner wall at the top (e.g., 12 o'clock) portion of the device is larger than a distance between the outer wall and inner wall at the bottom (e.g., 6 o'clock) portion of the device.

Figure 1K:
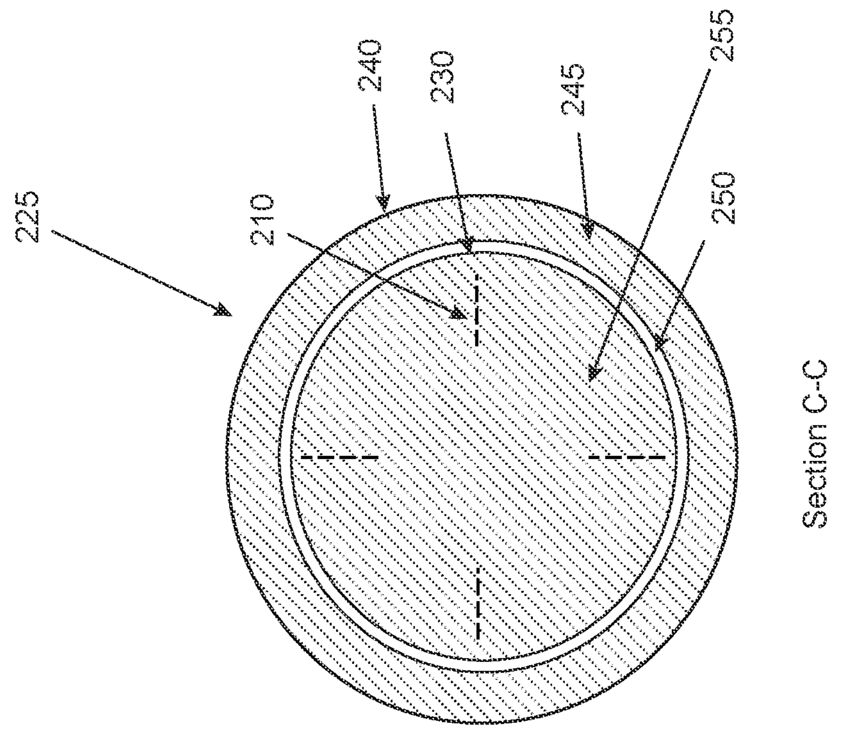
Figure 1J:
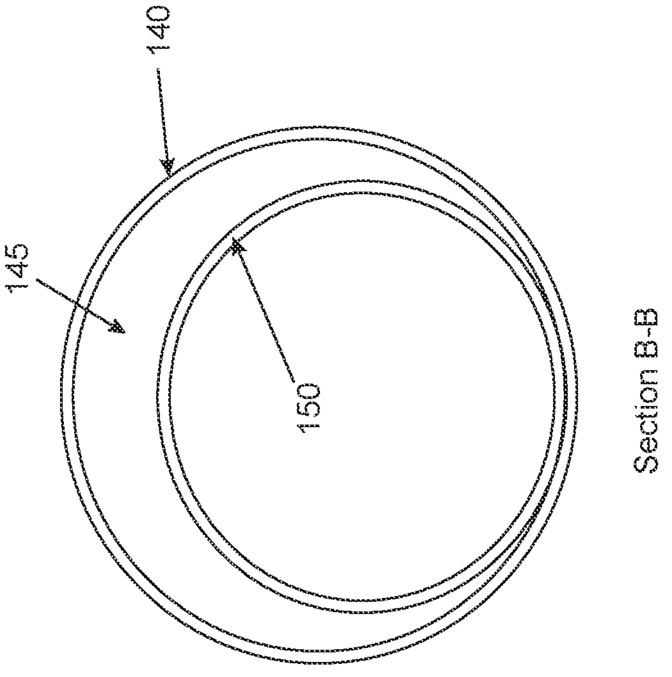

Section C-C of FIG. 1K illustrates in plan view a portion of the thrombus removal system comprising an irrigation manifold 225. Section C-C depicts an outer wall 240, an inner wall 250, a fluid lumen 245, an aspiration lumen 255, and ports 230 for directing respective fluid streams 210.

Figure 1L:
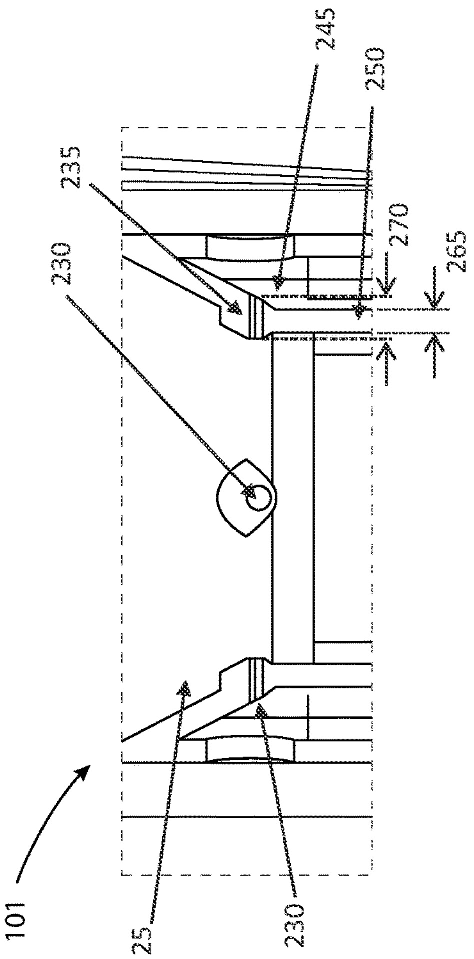
Figure 2A:
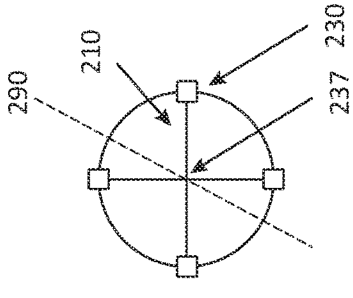
FIGS. 2A-2E illustrate plan views of various configurations of irrigation ports and fluid streams of a thrombus removal system according to embodiments of the present technology.
Figure 2B:
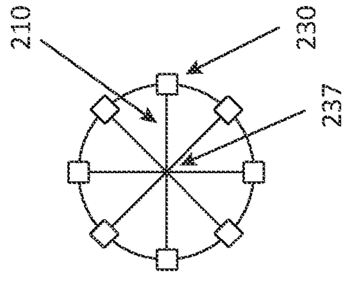
Figure 2C:
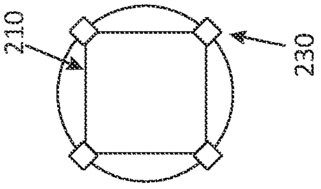
Figure 2D:
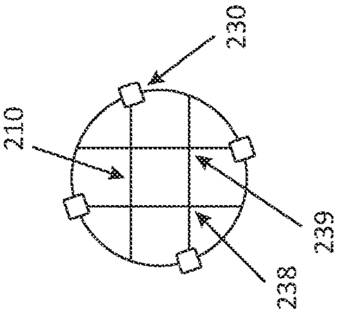
Figure 2E:
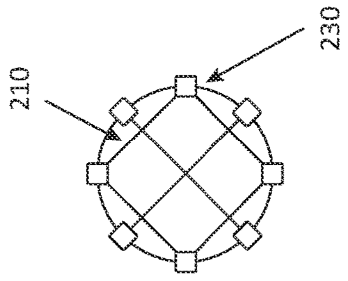
Figures 3A, 3B, 3C, 3D, 3E, 3F, 3G, 3H:
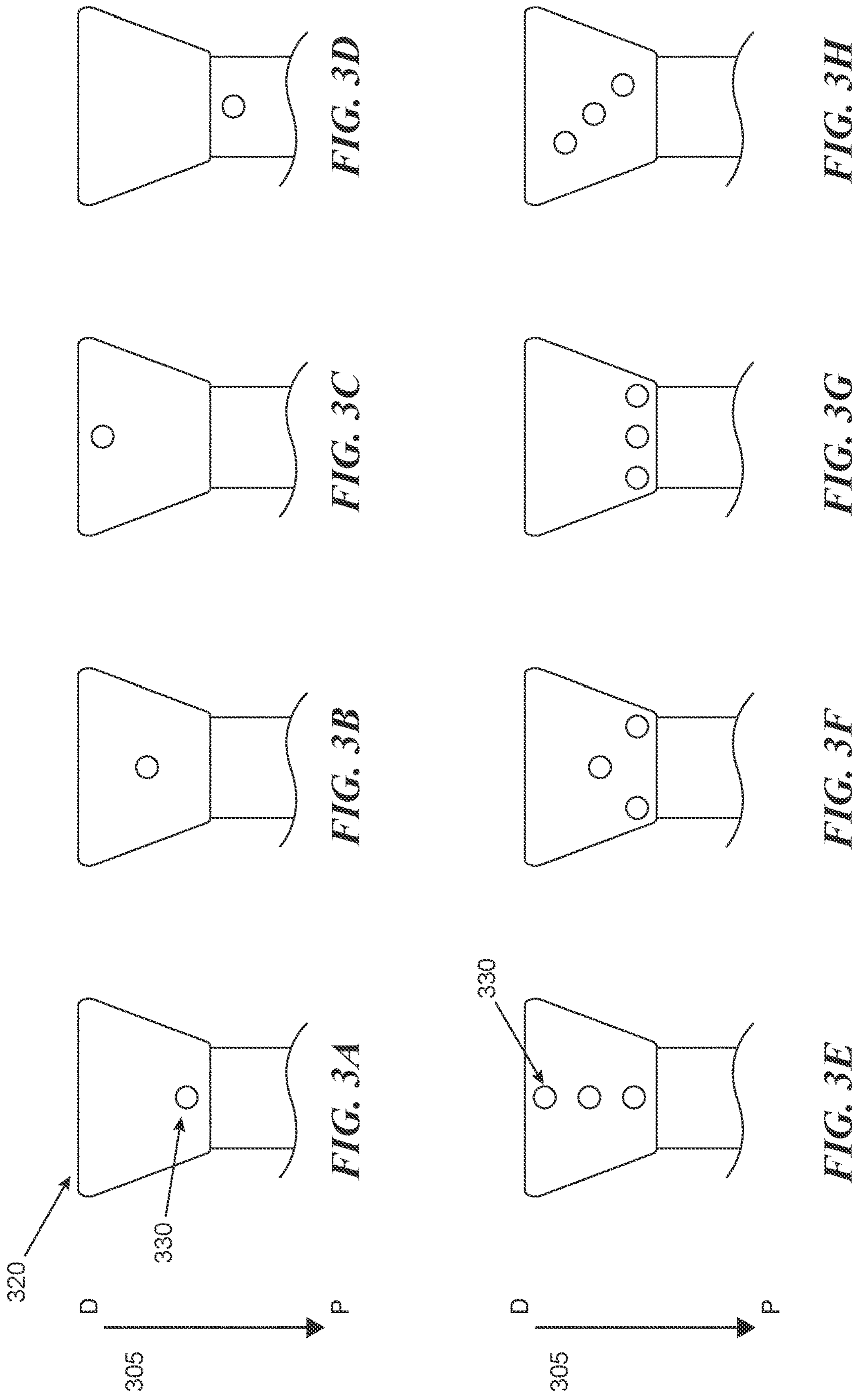
FIGS. 3A-3H illustrate an elevation view of various configurations of irrigation ports of a thrombus removal system according to embodiments of the present technology.

Detail View 101 of FIG. 1L illustrates a section view in elevation of a portion of the irrigation manifold 25 that includes a plurality of ports 230 that are formed within an inner wall 250. In some embodiments, a thickness of one or more walls of the thrombus removal system may be varied along its axial length and/or its circumference. As shown in Detail View 101, inner wall 250 has a first thickness 265 in a region 250 that is proximal to the irrigation manifold 25, and a second thickness 270 in a region 235 that includes the ports 230. In some embodiments, the second thickness 270 is greater than the first thickness 265. The first thickness 265 can correspond to a general wall thickness of the inner wall 50 and/or of the outer wall 40, which can be from about 0.10 mm to about 0.60 mm, or any value within the aforementioned range. The second thickness 270 can be from about 0.20 mm to about 0.70 mm, from about 0.70 mm to about 0.90 mm, or from about 0.90 mm to about 1.20 mm. The second thickness 270 can be any value within the aforementioned range. The dimension of the second thickness 270 can be selected to provide a fluid path through the ports 230 that produces a generally laminar flow for a fluid stream that is directed therethrough, when the fluid delivery mechanism supplies fluid via the fluid lumen 245 at a typical operating pressure. Such operating pressure can be from about 10 psi to about 60 psi, from about 60 psi to about 100 psi, or from about 100 psi to about 150 psi. The operating pressure of the fluid delivery mechanism can be any value within the aforementioned range of values. In some embodiments, the fluid delivery mechanism is operated in a high pressure mode, having a pressure from about 150 psi to about 250 psi, from about 250 psi to about 350 psi, from about 350 psi to about 425 psi, or from about 425 psi to about 500 psi. The operating pressure of the fluid delivery mechanism in the high pressure mode can be any value within the aforementioned range of values.

The manifold is configured to increase a fluid pressure and/or flow rate of the fluid. When fluid is provided by the fluid delivery mechanism to the fluid lumen(s) at a first pressure and/or a first flow rate, the manifold is configured to increase the pressure of the fluid to a second pressure and/or is configured to increase the flow rate of the fluid to a second flow rate. The second pressure and/or second fluid rate can be higher than the first pressure and/or first flow rate. As a result, the manifold can be configured to increase the relatively low operating pressures and/or flow rates generated by the fluid delivery mechanism to the relatively high pressures and/or high flow rates generated by the ports/fluid streams.

In some embodiments, a profile (cross-sectional dimension) of a port 230 varies along its length (e.g., is non-cylindrical). A variation in the cross-sectional dimension of the port may alter and/or adjust a characteristic of fluid flow along the port 230. For example, a reduction in cross-sectional dimension may accelerate a flow of fluid through the port 230 (for a given volume of fluid). In some embodiments, a port 230 may be conical along its length (e.g., tapered), such that its smallest dimension is positioned at the distal end of the port 230, where distal is with respect to a direction of fluid flow.

In some embodiments, the port 230 is formed to direct the fluid flow along a selected path. FIGS. 2A-2E illustrate various embodiments of arrangements of ports 230 for directing respective fluid streams 210. In some embodiments, such as those shown in FIGS. 2A and 2B, at least two ports 230 are arranged to produce (e.g., respective) fluid streams 210 that intersect at an intersection region 237 of the thrombus removal system. An intersection region 237 can be a region of increased fluid momentum and/or energy transfer, which multiply with respect to individual fluid streams that are not directed to combine at the intersection. The increased fluid momentum and/or energy transfer at an intersection may advantageously fragment thrombus more efficiently and/or quickly. As described above, the fluid streams can be configured to accelerate and cause cavitation and/or other effects to further add to breaking up of the target clot. In some embodiments, an intersection region can be formed from at least 2, at least 3, at least 4, at least 5, at least 6, at least 7, at least 8, at least 9, or at least 10 fluid streams 210. An intersection region can be generally near a central axis 290 of the thrombus removal system (e.g., 237), or away from the central axis (e.g., 238 and 239 in the embodiment of FIG. 2D). In some embodiments, at least two intersection regions (e.g., 238 and 239) are formed. In some embodiments, one or more ports 230 are arranged to direct a fluid stream 210 along an oblique angle with respect to the central axis of the thrombus removal system. An operating pressure of the fluid delivery mechanism may be selected to approach a minimum targeted fluid velocity for a fluid stream 210 that is delivered from a port 230. The targeted fluid velocity for a fluid stream 210 can be about 5 meters/second (m/s), about 8 m/s, about 10 m/s, about 12 m/s, or about 15 m/s. Additionally, the targeted fluid velocities in some embodiments can be in the range above 15 m/s to up to 150 m/s. At these higher velocities (e.g. above 15 m/s, or alternatively above 20 m/s), the fluid streams may be configured to generate cavitation in a target thrombus or tissue. It has been found that with fluid exiting from the ports to these flow rates a cavitation effect can be created in the focal area of the intersecting or colliding fluid streams, or additionally at a boundary of one or more of the fluid streams. While the exact specifications may change based on the catheter size, in general, at least one of the fluid streams should be accelerated to such a high velocity to create cavitation as described in detail below. The targeted fluid velocity for fluid stream 210 can be any value within the range of aforementioned values. In some embodiments, at least two ports 230 are adapted to deliver respective fluid streams at different fluid velocities (i.e. speed and direction), for a given pressure of the fluid delivery mechanism. In some embodiments, at least two ports 230 are adapted to deliver respective fluid streams at the substantially the same fluid velocities, for a given pressure of the fluid delivery mechanism. In some embodiments, one port is adapted to deliver fluid at high velocity and the respective one or more other ports is adapted to deliver fluid at relatively lower velocities. Advantageously, an increased cross-sectional area of the fluid lumen 145 reduces a required operating pressure of the fluid delivery mechanism to achieve a targeted fluid velocity of the fluid streams.

In some embodiments, the fluid streams are configured to create angular momentum that is imparted to a thrombus. In some examples, angular momentum is imparted on the thrombus by application of a) at least one fluid stream 210 that is directed at an oblique angle from a port 230, and/or b) at least two fluid streams 210 that have different fluid velocities. For example, fluid streams that cross near each other but do not necessarily intersect may create a "swirl" or rotational energy on the clot material. Advantageously, angular momentum produced in a thrombus may impart a (e.g., centrifugal) force that assists in fragmentation and removal of the thrombus. Rotating of the clot may enhance delivery of the clot material to the jets. By example, with a large, amorphous clot the soft material may be easily aspirated or broken up by the fluid streams whereas tough fibrin may be positioned away from the fluid streams. Rotating or swirling of the clot moves the material around so the harder clot material is presented to the jets. The swirling may also further break up the clot as it is banged inside the funnel.

Referring to FIGS. 3A-3H, ports 330 can be arranged along various axial positions of the thrombus removal system. The thrombus removal system can include a flow axis 305 that is aligned with a general direction (e.g., distal-to-proximal) of flow for fluid that is aspirated therein. In some embodiments, a position of a port 330 comprises a) near a base of, b) in a middle portion of, c) in a distal portion of, or d) proximal to, a funnel portion 320 of the thrombus removal system. In some embodiments, at least two ports 330 are aligned along flow axis 305. In some embodiments, at least two ports 330 are arranged at a different axial and/or angular positions along the flow axis 305. In some embodiments, at least two ports 330 are arranged (e.g., along a perimeter of the thrombus removal system) along a given axial position of the flow axis 305.

FIGS. 4A-4H depict various configurations of fluid streams 410 that are directed from respective ports 430. A fluid stream 410 can be directed along a path that is substantially orthogonal, proximal, and/or distal to the flow axis 405 (which is like to flow axis 305). In some embodiments, at least two fluid streams are directed in different directions with respect to the flow axis 405. In some embodiments, at least two fluid streams are directed in a same direction (e.g., proximally) with respect to the flow axis 405. In some embodiments, at least a first fluid stream is directed orthogonally, at least a second fluid stream is directed proximally, and at least a third fluid stream is directed distally with respect to the flow axis 405. An angle a may characterize an angle that a fluid stream 410 is directed with respect to an axis that is orthogonal to the flow axis 405 (e.g., as shown in section D-D of FIGS. 4G and 4H). An intersection region of fluid streams can be within an interior portion of the thrombus removal system, and/or exterior (e.g., distal) to the thrombus removal system. In some embodiments, a fluid stream that is directed by a port 430 in a nominal direction (e.g., distally) is deflected along an altered path (e.g., proximally) by (e.g., suction) pressure generated by the aspiration mechanism during operation.

Cavitation Generation

The exemplary system includes fluidic jets configured in a particular manner to enhance removal of clot. The exemplary fluid streams or jets have been shown in bench studies to dramatically improve removal of clot through various mechanisms of action including, but not limited to, cavitation and water cutting. In contrast to conventional fluid mechanisms for thrombectomy, in some embodiments herein, fluid streams 410 from respective ports 430 are delivered at sufficient flow rates (and patterns) to create cavitation and/or other preferential effects to improve removal of clot. In certain examples, the cavitation effect is created by large pressure drops and deceleration at the focal point and/or intersection point of at least two fluid streams. The cavitation may provide a source of turbulent kinetic energy that can be used to mechanically fractionate and/or liquefy thrombi or other target tissue structures. When the fluid velocity is sufficiently high, the material accumulates impact energy, which can cause deformation and fragmentation. This also may modify the surface properties of the clot to allow the material to be penetrated to enable cavitation within the clot. Collision or interaction of the high-speed jets creates hydrodynamic cavitation whereby a pressure drop below the vapor pressure of the liquid creates bubbles which eventually collapse with great mechanical energy in the cavitation field, causing a kind of implosion in the clot material. Further, with multiple jets directed towards a focal point or sufficiently near respective streams, the closing speed of the fluid particles is significantly higher (up to double) that of a single jet stream. This also forces fluid and/or particles out from the space between the fluid jets at high speed. The speed of the fluid jets is sufficiently high to create a pressure drop below the vapor pressure such that the fluid vaporizes. When pressure rises again the bubble collapses, which causes the cavitation. It has been found that the power of the exemplary system and cavitation effect significantly exceeds conventional fluid jet(s) and mechanical tools like rotating screws. In some examples, the collapse of the bubbles may generate heat in or around the target tissue, which may further promote breaking up of the clot. In bench studies systems in accordance with various embodiments were able to remove certain clot material that simple aspiration or water jetting were not. In other studies, the exemplary systems were able to remove clot material in a fraction of the time of conventional systems.

Figures 4A, 4B, 4C, 4D, 4E, 4F, 4G, 4H:
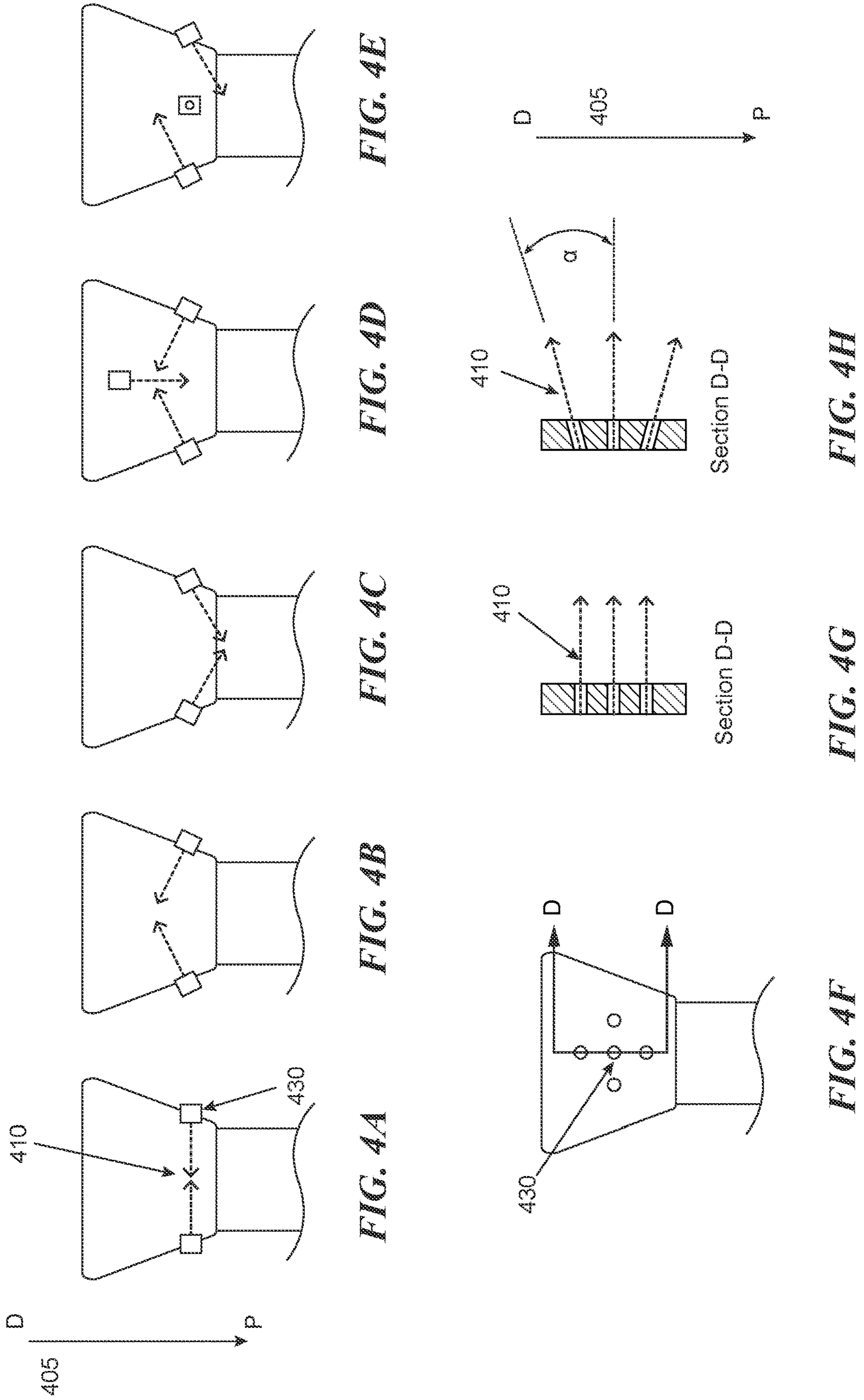
FIGS. 4A-4P illustrate an elevation view of various configurations of irrigation ports and fluid streams of a thrombus removal system according to embodiments of the present technology.
Figure 4K:
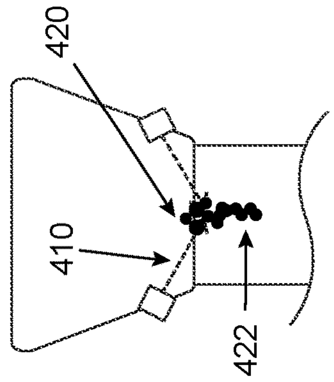
Figure 4J:
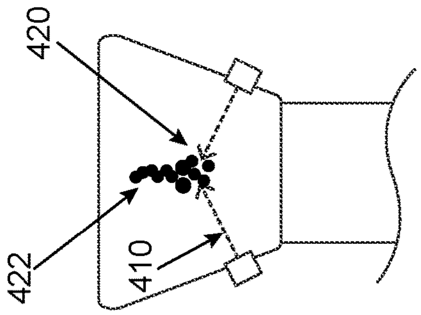
Figure 4I:
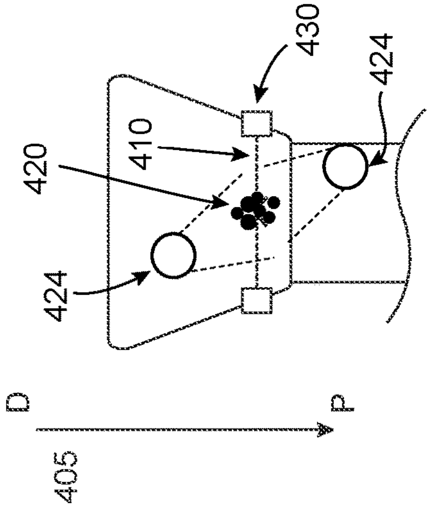

FIGS. 4I-4K illustrate examples of generation of cavitation 420 at the intersection, collision, or interaction of two or more fluid streams 410. Referring to FIG. 4I, fluid streams 410 from at least two ports 430 are directed generally parallel to another and orthogonal to flow axis 405 of the thrombus removal device. As shown in the embodiment of FIG. 4I, the cavitation 420 is generally confined to the region of interaction (e.g., the focal point) between the fluid streams 410. As illustrated, the cavitation 420 can comprise a plurality of microbubbles. When a thrombus is engaged with a funnel of the thrombus removal device, the fluid streams 410 and/or cavitation 420 can be used to break up, fractionate, liquefy, and/or dissolve the thrombus to facilitate aspiration and removal of the thrombus with the device.

In the embodiment of FIG. 4J, the fluid streams 410 from at least two ports 430 are not directed orthogonal to the flow axis 405, but instead are directed slightly distally from the ports to create cavitation 420 in an interaction region that is distal to the ports 430. In some embodiments, depending on the velocity/flow rate of the fluid streams, the resulting collision of the distally directed fluid streams can additionally create a cavitation column 422 that propagates and/or resides distally to cavitation 420 in the intersection region. When a thrombus is engaged with a funnel of the thrombus removal device in this embodiment, the fluid streams 410 and/or cavitation can be used to break up, fractionate, liquefy, and/or dissolve the thrombus to facilitate aspiration and removal of the thrombus with the device. Additionally, cavitation column 422 can provide additional kinetic energy to break up, fractionate, liquefy, and/or dissolve portions of the thrombus distal to the cavitation 420. Although the embodiment of FIG. 4J is shown as including a funnel to assist with thrombus engagement and aspiration, it should be understood that in other embodiments, the device may not include a funnel. In these embodiments, the cavitation 420 and cavitation column 422 can be used to break up, fractionate, liquefy, and/or dissolve a thrombus located distally to the device and ports 430.

In the embodiment of FIG. 4K, the fluid streams 410 from at least two ports 430 are not directed orthogonal to the flow axis 405, but instead are directed slightly proximally from the ports to create cavitation 420 in an interaction region that is proximal to the ports 430. In some embodiments, depending on the velocity/flow rate of the fluid streams, the resulting collision of the proximally directed fluid streams can additionally create a cavitation column 422 that propagates and/or resides proximally to cavitation 420 in the interaction region and in the same direction as aspiration of the thrombus removal device. When a thrombus is engaged with a funnel of the thrombus removal device in this embodiment, the fluid streams 410 and/or cavitation can be used to break up, fractionate, liquefy, and/or dissolve the thrombus to facilitate aspiration and removal of the thrombus with the device. Additionally, cavitation column 422 can provide additional kinetic energy to break up, fractionate, liquefy, and/or dissolve portions of the thrombus proximal to the cavitation 420 which may further assist in aspiration of the thrombus into the device.

Figure 4L:
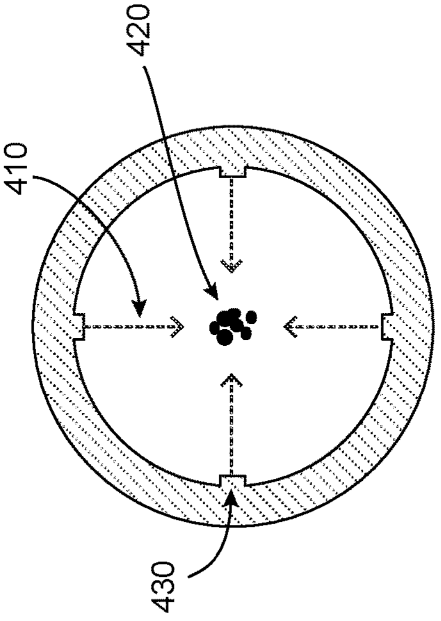

FIG. 4L illustrates a top down view of a thrombus removal device. In this embodiment, the device includes a total of four intersecting or interacting fluid streams 410. As described above, the interaction between the fluid streams and/or the flow rates of the fluid streams can create conditions sufficient to generate cavitation 420 at the interaction region of the fluid streams. While this embodiment shows four fluid streams, it should be understood that any number of fluid streams can be implemented to achieve cavitation, including two fluid streams, three fluid streams, or more than four fluid streams.

As described above, the thrombus removal device can include one or more fluid lumens (e.g., fluid lumen 45 in FIG. 1A) configured to provide fluid to one or more apertures (e.g. apertures 30 in FIG. 1A or ports 430 in FIGS. 4A-4K). According to one aspect of this disclosure, cavitation can be formed at the interaction region between at least two fluid streams when the flow rate of the fluid streams is high enough to create appropriate pressure drops and deceleration at and around the focal point and/or intersection point of the streams. In one embodiment, a flow rate of approximately 3 m/s within the fluid lumen(s) of the thrombus removal device results in a fluid stream exiting the ports with a flow rate of at least 50 m/s. In this embodiment, two or more fluid streams, each having a flow rate of at least 50 m/s, can be configured to generate cavitation at an interaction region of the fluid streams. In another embodiment, a flow rate of approximately 4 m/s within the fluid lumen(s) of the thrombus removal device results in a fluid stream exiting the ports with a flow rate of at least 70 m/s. In this embodiment, two or more fluid streams, each having a flow rate of at least 70 m/s, can be configured to generate cavitation at an interaction region of the fluid streams. In yet another embodiment, a flow rate of approximately 5 m/s within the fluid lumen(s) of the thrombus removal device results in a fluid stream exiting the ports with a flow rate of at least 90 m/s. In this embodiment, two or more fluid streams, each having a flow rate of at least 90 m/s, can be configured to generate cavitation at an interaction region of the fluid streams. Generally, the thrombus removal device of the present disclosure is configured to provide fluid in the one or more fluid lumens at a flow rate of 3-5 m/s which correlates to fluid streams exiting the jets, ports, or apertures at a flow rate of 50-90 m/s. Fluid streams at these flow rates are configured to create the appropriate pressure drops and deceleration at the focal point or interaction region of the fluid streams to generate cavitation.

In another embodiment, cavitation at the focal point or interaction region of the fluid streams can be characterized not by the flow rate of the fluid streams, but instead by the pressure drop at the intersection or passing/shearing of the fluid streams. When the pressure drop exceeds a cavitation threshold, cavitation is formed at that location. In one embodiment, this pressure drop can be at least 20 MPa. In other embodiments, the pressure drop can be any pressure drop greater than 25 MPa. Since the pressure drop is dependent on the fluid shear it is possible to create cavitation at the boundary of a single jet (e.g., halo cavitation). Therefore, in some embodiments, two fluid streams passing along some common boundary becomes a variation where the shear creating the cavitation can be created by two streams moving in opposite directions of lower velocities, as shown in FIGS. 4N and 4O and described in more detail below.

In another embodiment, the ports can be arranged in a slightly offset configuration such that crossing or intersecting fluid streams only partially collide at the interaction region. In this embodiment, at least four distinct breaking forces can be applied to the target thrombi, including 1) a "cutting" or slicing force as the individual fluid streams initially cut through the thrombus prior to meeting at a focal point or interaction region, 2) cavitation at the focal point or interaction region when the fluid streams intersect, partially intersect, collide, and/or partially collide, 3) shearing from the jet streams moving against each other on either side of the jets streams, the focal point, and/or the interaction region, and 4) swirling or halo rotational fluid motion caused by shearing and cavitation forces.

Figure 4M:
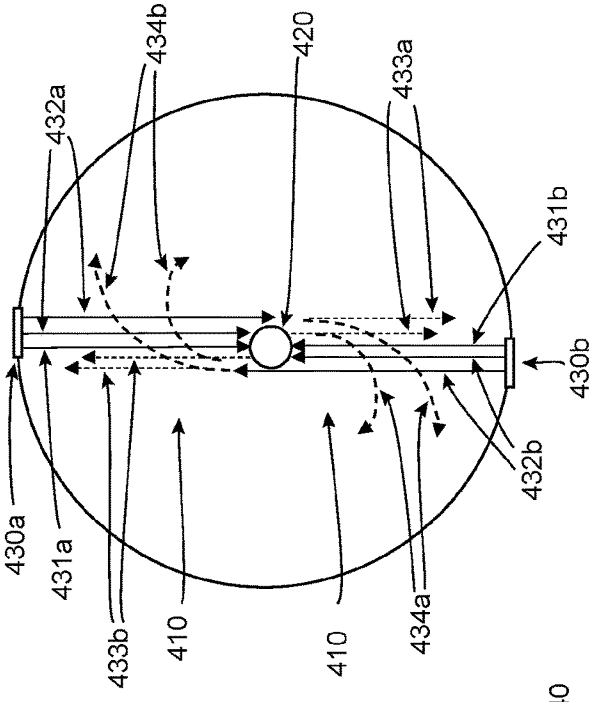
Figure 4N:
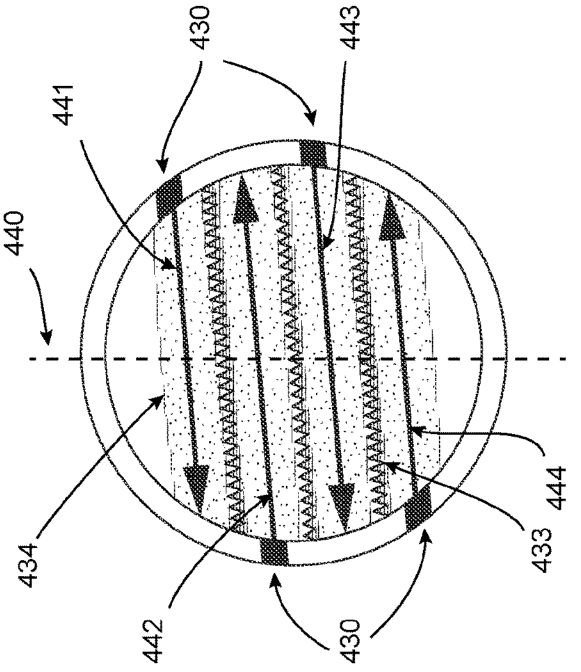
Figure 4O:
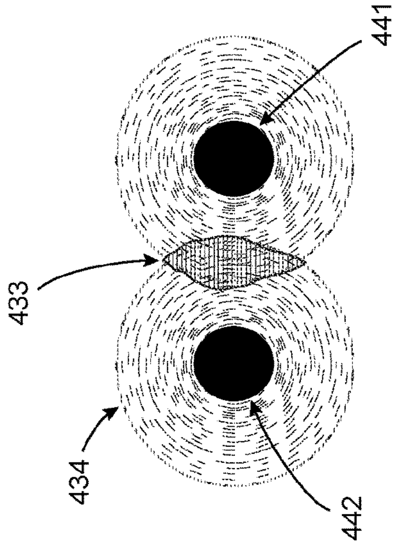

FIG. 4M shows a cross-sectional view of such a configuration, with ports 430*a* and 430*b* being disposed generally opposite each other across a shaft, funnel, or lumen of the thrombus removal device, but offset in a manner that prevents the entirety of the fluid streams from colliding with another. It should be understood that while this embodiment shows the ports generally on opposite sides of the lumen, funnel, or shaft of the device, any configuration of ports illustrated herein can be used as long as the ports are slightly offset so as to enable only partial collisions of the crossing or intersecting fluid streams.

Referring still to FIG. 4M, the at least four distinct breaking forces enabled by this configuration will now be described. During the initial activation or "turn on" of the fluid streams from ports 430*a* and 430*b*, the fluid streams will generally travel from the thrombus removal device through the thrombus towards an intersection point. As the fluid streams are moving in this direction, but before collision, the fluid streams provide a "cutting" or slicing force to the thrombus that is engaged with the device. When the fluid streams finally collide or intersect, as shown, since ports 430*a* and 430*b* are partially offset, only first portion 431*a* of the fluid stream from port 430*a* directly intersects or collides with first portion 431*b* of the fluid stream from port 431*b*. This collision or intersection of the fluid stream portions causes cavitation 420 at the intersection point when the flow rate of the fluid streams are sufficient to cause cavitation, as described above. As also shown in FIG. 4L, second portion(s) 432*a* of the fluid stream from port 430*a* does not collide or intersect with second portion(s) 432*b* of the fluid stream from port 430*b*. As such, these second portion(s) of the fluid streams continue past the intersection point and past the cavitation 420. However, the fluid streams moving past each other in opposite, opposing, or different directions causes shearing streams or shearing cavitation 433*a* and 433*b* to form within and/or around the thrombus, applying another type of breaking force on the thrombus. Additionally, the cavitation, the shearing streams, and/or the interaction between the partially offset ports further results in swirling streams or halo cavitation 434*a* and 434*b*, applying a fourth distinct breaking force to the thrombus engaged with the device.

FIGS. 4N and 4O illustrate additional views of a thrombus removal device that can include some or all of the breaking forces described above. FIG. 4N is a cross-sectional view of a thrombus removal device, and FIG. 4O is a longitudinal slice cutting across the fluid streams as represented by plane 440 in FIG. 4N. In FIG. 4N, the thrombus removal device can include a plurality of ports 430. In this embodiment, the ports are offset such that none of the fluid streams from the respective ports intersect or cross any of the other fluid streams. However, the ports are arranged in a manner that allows the fluid streams to pass closely next to adjacent fluid streams. In this example, first fluid stream 441 passes closely next to adjacent second fluid stream 442, which passes closely next to adjacent third fluid stream 443, which passes closely next to adjacent fourth fluid stream 444. The passing of close or adjacent fluid streams creates shearing streams or shearing cavitation 433 in between adjacent fluid streams, as shown. Additionally, as described above, the passing of close or adjacent fluid streams additionally creates swirling streams or halo cavitation 434. It should be understood that the steady state scenarios described herein will likely vary over time as the fluid flow resultant from the interactions impacts the velocities/directions of the fluid streams.

FIG. 4O is a view of a slice cutting across the fluid streams along plane 440 in FIG. 4N, showing fluid streams 441 and 442, shearing streams or shearing cavitation 433, and swirling streams or halo cavitation 434. It can be seen that the halo cavitation 434 that is caused by the passing streams can swirl or flow in a circular manner around the respective fluid streams, and even pass or converge into the shearing streams or shearing cavitation 433 at the center of the opposing streams. In combination, all of these breaking forces can provide additional breaking energy to act on, break up, cut up, and mechanically fractionate a thrombus engaged with the device.

Cavitation Detection

With the ability of the thrombus removal device to generate cavitation at the intersection region of two or more fluid streams, the thrombus removal device can further include cavitation detection capabilities to detect if and when cavitation is generated within or near a target thrombus. In some embodiments, the cavitation detection capabilities can detect the location and/or intensity of the cavitation. Cavitation detection further provides additional functionality in the operation of the device, providing an additional mechanism for detecting when the device is engaged with a thrombus.

In some embodiments, cavitation detection can be used to determine the interaction between the jets or fluid streams and the target thrombus. For example, when a thrombus is first engaged in a funnel of the device (e.g., with aspiration), the jets or fluid streams can be activated to provide two or more fluid streams inward towards a focal point or intersection point of the two or more fluid streams. However, during this initial activation of the jets or fluid streams, the thrombus may be positioned or located in between the two or more fluid streams, thereby preventing collision or intersection of the fluid streams. At this point in the therapy, as the fluid streams may not yet be intersecting, they first must "cut" or drive through the thrombus. Depending on the flow rate of the fluid streams as they initially "cut" through the thrombus, there may be no cavitation present.

Cavitation detection can be used to identify scenarios in which 1) a clot is engaged in the funnel, 2) aspiration is activated, 3) the jets or fluid streams are activated but cavitation is not present, and/or 4) the jets or fluid streams are activated and cavitation is present. For example, a pressure or flow measurement in the aspiration lumen while aspiration is activated can be used to determine if the clot is engaged in the funnel. Then, if cavitation is simultaneously detected, the system can indicate to the user that the clot is engaged and the jets or fluid streams are producing cavitation in the clot. If no cavitation is detected, then the system can indicate to the user that the clot is engaged and the jets or fluid streams are cutting the clot. In some embodiments, whether or not cavitation is detected can be displayed or indicated to the user. Therefore, the indication to the user on if cavitation is present or not present can provide useful information to the user regarding the state or status of the therapy (e.g., whether a thrombus is engaged, whether cutting is occurring, or whether cavitation is occurring).

As the treatment progresses, the jets or fluid streams will eventually cut through the thrombus in the funnel, causing the two or more jets to intersect at the focal point. When this event occurs, if the fluid streams have a sufficient flow rate (e.g., 20-90 m/s or more, as described above), the two or more intersecting fluid streams can be configured to generate cavitation at the focal point. It should be understood that in many situations, with the thrombus still engaged in the funnel of the thrombus removal device, this cavitation can further provide mechanical fractionation and/or liquefaction of the thrombus at the focal point. In some embodiments, the therapy includes alternating cycles of "cutting" and cavitation. As the thrombus moves around in the funnel and is broken up into smaller pieces or sections and aspirated into the thrombus removal device, there will be instances in which the fluid streams are intersecting, and therefore creating cavitation, and there will be instances in which the fluid streams are not intersecting (e.g., perhaps due to the thrombus preventing intersection) and rely instead on the "cutting" nature of the jets to break up the clot.

In some embodiments, the ability to detect cavitation can be used to direct the jet and/or aspiration control schemes of the thrombus removal device. For example, it may be beneficial to alternate between "cutting" and "cavitation" modes of the thrombus removal device. In one example, the jets are activated to "cut" through an engaged thrombus until cavitation is detected. Once cavitation is detected, the jets can remain active for a preset period of time. Next, the jets can be temporarily pulsed or turned off, with aspiration remaining on, to allow the thrombus to shift or move deeper into the funnel. Then the jets can be activated again, restarting a cycle of a "cutting" mode followed by a "cavitation" mode. In some embodiments, it may be desirable to avoid cavitation and instead rely only on the cutting mechanism of action. In this instance, cavitation detection can be used to alert or indicate to a user that cavitation has formed. In some embodiments, the device can automatically pause or pulse the jets when cavitation is detected, to allow the clot to fill the funnel and restart the cutting process with the jets.

Referring back to FIG. 4I, in some embodiments the thrombus removal device can include a cavitation detection sensor 424. The cavitation detection sensor can comprise, for example, an ultrasound transducer element or a hydrophone. The sensor may detect cavitation by monitoring for cavitation directly and/or indirectly. In the case of indirect monitoring, the sensor monitors characteristics of the fluid stream and identifies the desired cavitation based on known correlations. The correlations may vary based on the size and shape of the catheter end (or funnel), orientation of the jets and focal point, etc. In the embodiment of FIG. 4I, the device is shown with a cavitation detection sensor 424 in the funnel and a second cavitation detection sensor 424 in the shaft/aspiration lumen of the device. While only the embodiment of FIG. 4I is illustrated to include a cavitation sensor (s), it should be understood that any embodiment or jet configuration described herein can further include one or more cavitation sensors. Generally these cavitation detection sensors can be directed or pointed towards the intersection point of the two or more fluid streams. It should be understood that in other embodiments, these devices can include one, or more than two cavitation detection sensors. The sensors may be located only in the funnel, only in the shaft/aspiration lumen, or a combination of both as shown. Generally, the cavitation detection sensors can be positioned anywhere within or on the device that provides an acoustic path between the sensor and the target cavitation region. Although only the embodiment of FIG. 4I shows a device with a cavitation detection sensor, it should be understood that any thrombus removal device described herein can include such functionality, including the embodiments of FIGS. 4J and 4K. Since those embodiments include distally and proximally directed fluid streams, respectively, thereby enabling formation of a cavitation column, it should be understood that in those embodiments, the cavitation detection sensors can be configured to sense and/or detect both the cavitation 420 and the cavitation column 422.

Other types of sensors are proposed, including a microphone configured to detect cavitation, or a laser configured to detect temperature changes at the intersection point when cavitation occurs.

In addition to cavitation detection with a sensor disposed on or in the device, in other embodiments the thrombus removal device can be used in conjunction with a separate cavitation detection device, such as a real-time imaging device. For example, cavitation can be identified as a hyper-echoic region in real-time B-mode ultrasound imaging. Therefore, in one embodiment, an ultrasound imaging device can be directed towards the target thrombi and be used to identify when cavitation occurs in real-time, providing real-team feedback to a physician or surgeon during a thrombus removal procedure. The ultrasound imaging device can comprise, for example, an external ultrasound imaging probe (e.g., placed in contact with the skin of the patient). Alternatively, the ultrasound imaging device can comprise an internal or catheter-based ultrasound imaging probe configured to be advanced along with or within the thrombus removal device to the target thrombus location.

Figure 4P:
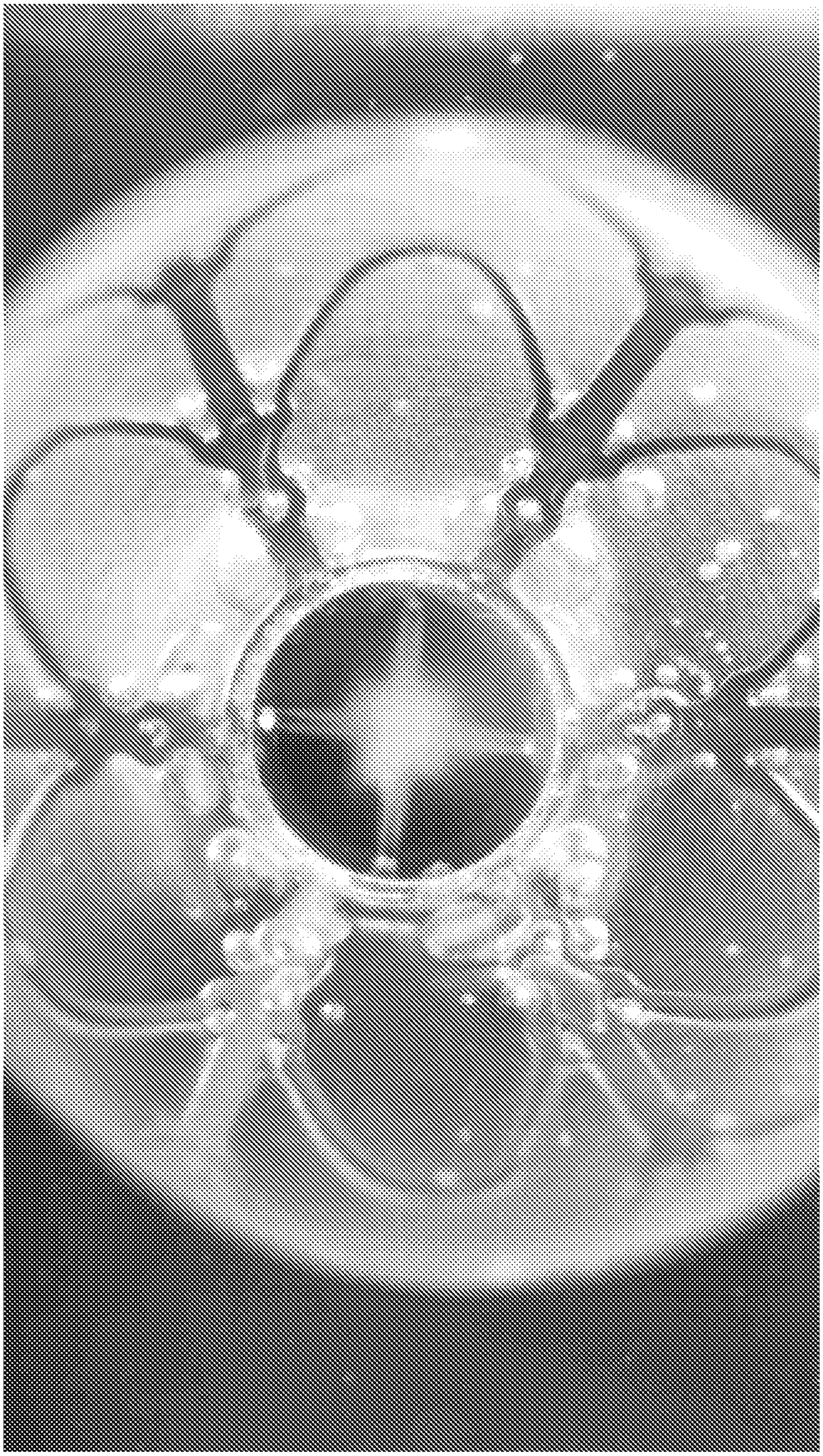
Figure 5A:
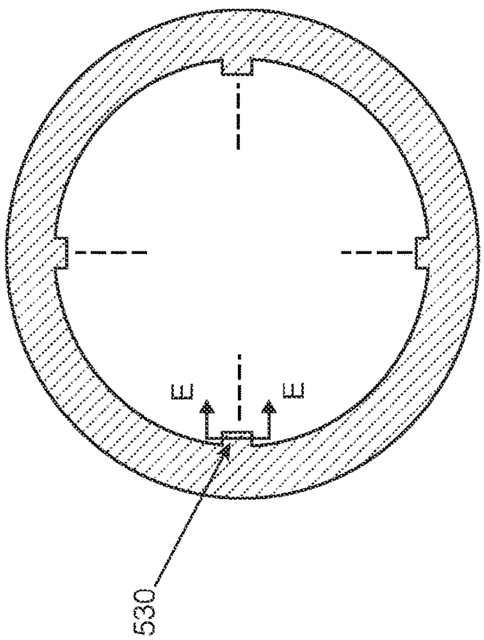
FIGS. 5A-5G illustrate various configurations of irrigation ports of a thrombus removal system according to embodiments of the present technology.
Figure 5B:
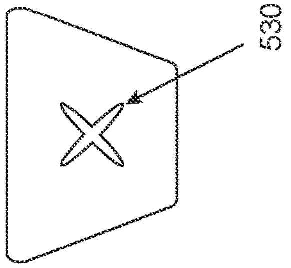
Figure 5C:
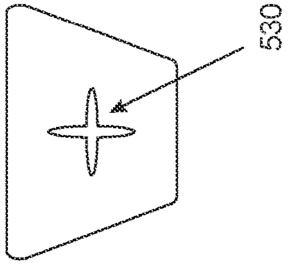
Figure 5D:
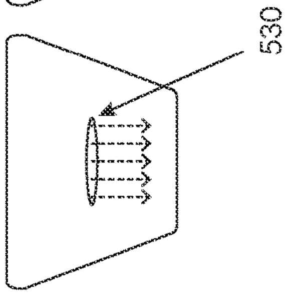
Figure 5E:
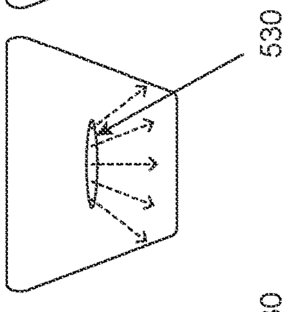
Figure 5F:
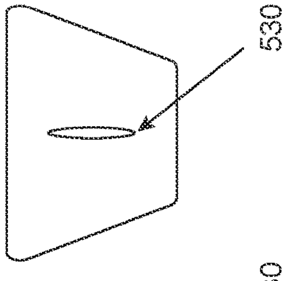
Figure 5G:
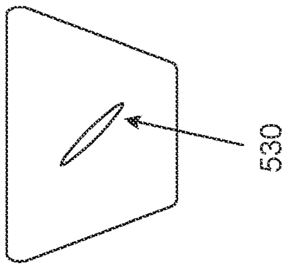

FIG. 4P is a photograph of a benchtop experiment showing the formation of cavitation at an interaction region of four interacting or intersecting jets or fluid streams. In this experiment, the fluid source (e.g., a water pump) was pulsed to have an operating pressure ranging from peak 200 psi to 750 psi. The fluid source was then able to produce a flow rate in the fluid lumen of the device having an average velocity ranging between 2 m/s and 10 m/s. That flow rate in the fluid lumen resulted in an average velocity out of the jet apertures ranging between 50 m/s and 200 m/s. With the same setup, the fluid source was operated at a pulsed pressure to produce an average velocity out of the jet apertures below 10 m/s and no cavitation was observed.

FIGS. 5A-5G illustrate a variety of exit aperture geometries with which ports 530 can be configured in accordance with embodiments of the present technology. Aperture geometries can comprise an oval, circular, cross ("x" shape), "t" shape, rectangle, or square shape. A fluid stream that is delivered from the port 530 can comprise substantially laminar flow (e.g., at the aperture), or a turbulent flow (e.g., that fans outward). The size of the ports 530 can be adjusted to achieve the appropriate exit velocity and acceleration of the fluid streams. In some embodiments, these port sizes can be optimized to achieve a flow rate of 50-90 m/s so as to create cavitation at the intersection point of the two or more fluid streams. Generally, smaller ports create a higher velocity fluid stream, at the expense of transmitting less kinetic energy due to lower volume of fluid exiting the ports.

Figure 6A:
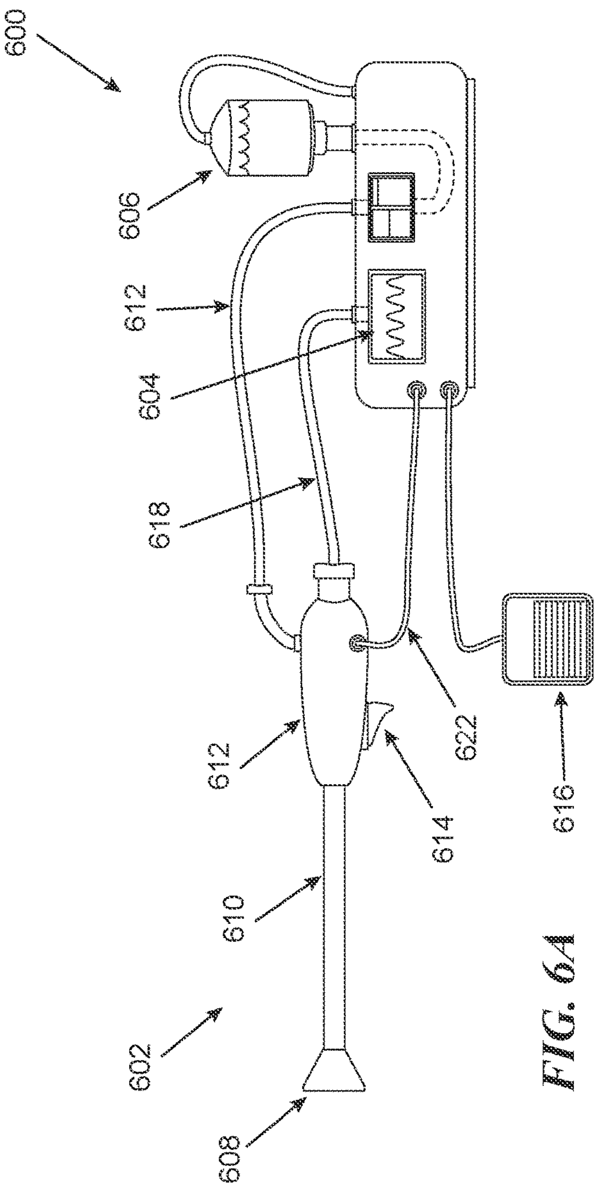
FIGS. 6A-6C illustrate various embodiments of a thrombus removal system including a saline source, an aspiration system, and one or more controls for controlling irrigation and/or aspiration of the system.
Figure 6B:
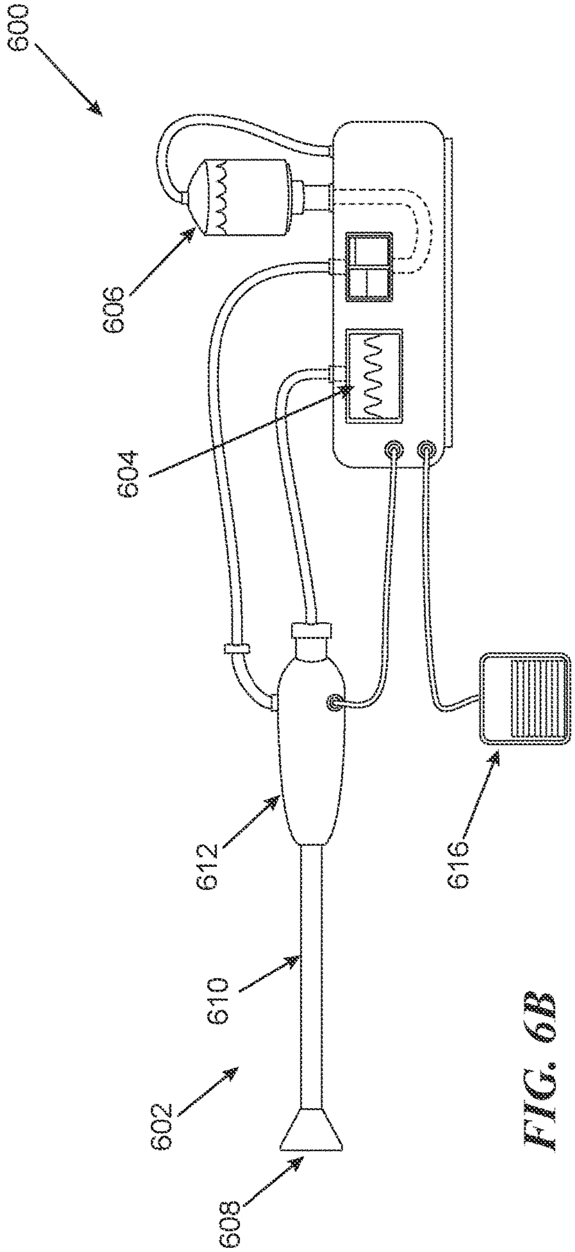
Figure 6C:
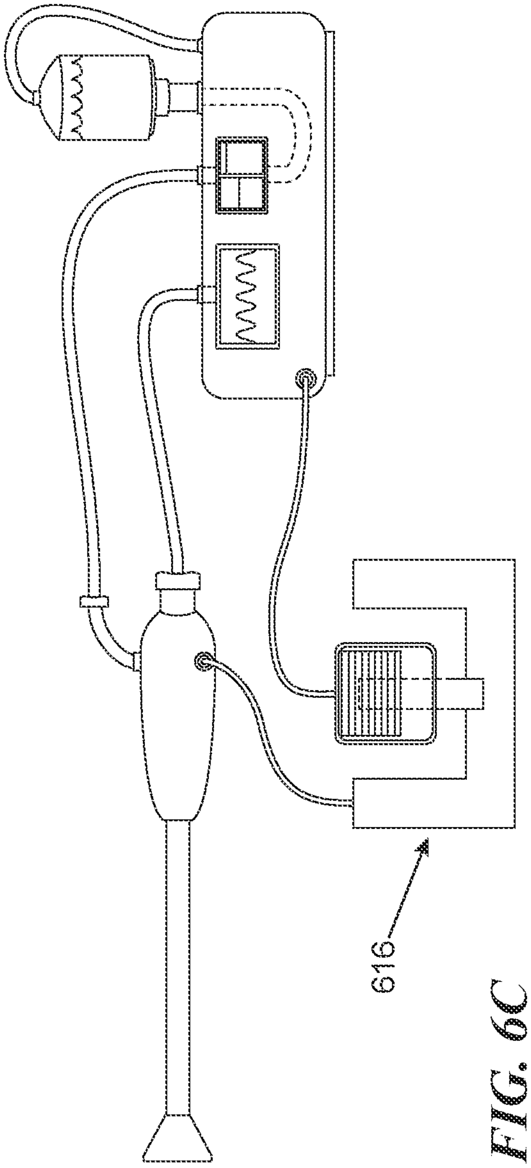

FIGS. 6A-6C illustrate various configurations of a thrombus removal system 600, including a thrombus removal device, 602, a vacuum source and cannister 604, and a fluid source 606. In some embodiments, the vacuum source and cannister and the fluid source are housed in a console unit that is detachably connected to the thrombus removal device. A fluid pump can be housed in the console, or alternatively, in the handle of the device. The console can include one or more CPUs, electronic controllers, or microcontrollers configured to control all functions of the system. The thrombus removal device 602 can include a funnel 608, a flexible shaft 610, a handle 612, and one or more controls 614 and 616. For example, in the embodiment shown in FIG. 6A, the device can include a finger switch or trigger 614 and a foot pedal or switch 616. These can be used to control aspiration and irrigation, respectively. Alternatively, as shown in the embodiment of FIG. 6B, the device can include only a foot switch 614, which can be used to control both functions, or in FIG. 6C, the device can include only an overpedal 616, also used to control both functions. It is also contemplated that an embodiment could include only a finger switch to control both aspiration and irrigation functions. As shown in FIG. 6A, the vacuum source can be coupled to the aspiration lumen of the device with a vacuum line 618. Any clots or other debris removed from a patient during therapy can be stored in the vacuum cannister 604. Similarly, the fluid source (e.g., a saline bag) can be coupled to the fluid lumens of the device with a fluid line 620.

Still referring to FIG. 6A, electronics line 622 can couple any electronics/sensors, etc. from the device to the console/controllers of the system. The system console including the CPUs/electronic controllers can be configured to monitor fluid and pressure levels and adjust them automatically or in real-time as needed. In some embodiments, the CPUs/electronic controllers are configured to control the vacuum and irrigation as well as electromechanically stop and start both systems in response to sensor data, such as pressure data, flow data, etc.

As is described above, aspiration occurs down the central lumen of the device and is provided by a vacuum pump in the console. The vacuum pump can include a container that collects any thrombus or debris removed from the patient.

Clog Detection and Clog Removal

In some situations, the device may become clogged with a thrombus or with other debris during therapy. Many clog detection and clog removal schemes can be implemented in the thrombus removal system. Generally, clogs in the system or device can be detected with any number of sensors disposed in or around the device. For example, pressure sensors can be disposed on or in the funnel, on or in the fluid lumens, or on or in the aspiration lumen of the device or system at any number of locations. The sensor data can then be used to monitor the operation of the device. For example, pressure sensors in the aspiration lumen can provide an indication if the device is clogged with a clot or other debris. The system can monitor the pressure in the aspiration lumen, and significant changes in pressure from the normal operating pressure can indicate a problem with the device or the therapy. For example, a pressure sensor reading that drastically drops from the normal operating pressure range could indicate that a clot or other debris is clogging the device or system proximal to the pressure sensor. Similarly, a pressure sensor reading that drastically increases from the normal operating pressure range could indicate that a clot or other debris is clogging the device or system distal to the pressure sensor.

Pressure sensors disposed along a length of the device can therefore be used in this manner to determine if the device is clogged and even identify where along the length of the device the clog is located based on which pressure sensors have higher than normal pressure readings and which pressure sensors have lower than normal pressure readings. Similarly, flow meters or sensors can be used to monitor the flow of fluid in the fluid lumens and/or the flow of debris, blood, and clots in the aspiration lumen. These flow sensor readings can be used to determine if the aspiration lumen or a flow lumen (and potentially a jet or aperture) is clogged or blocked.

In one embodiment, the system can be configured to produce vacuum suction with a large volume piston pump that can be selectively controlled. This enables automatically stopping vacuum when pressure and/or other sensors in the thrombus removal device detect a sharp change in vacuum pressure as a result of a clog. Once detected, the system can be configured to automatically halt irrigation jetting and the vacuum piston resulting vacuum in instant removal of vacuum pressure to reduce blood loss and prevent over irrigating the patient.

In another embodiment, when the system detects a clogged device, the system can be configured to automatically holt irrigation and aspiration, then run a declogging routine that rapidly cycles vacuum pressure to induce a "fluid hammer" effect to remove the clot or clog.

Figure 7A:
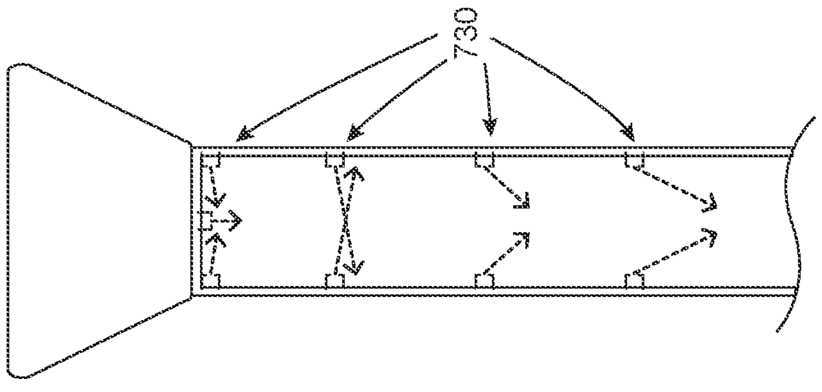
FIGS. 7A-7D illustrate various configurations of clog detection and/or clog removal features of a thrombus removal system.

Additional embodiments are provided for removing clogs or clots from the device. Referring to FIG. 7A, the thrombus removal device can include a plurality of jets 730 disposed along a length of the device, including along the shaft of the device. In some embodiments, the jets can be pointed in different angles to assist in moving the clot or debris proximally along the device. For example, the jets can be aimed generally proximally along the shaft of the device to push or force clots in that direction.

Figure 7B:
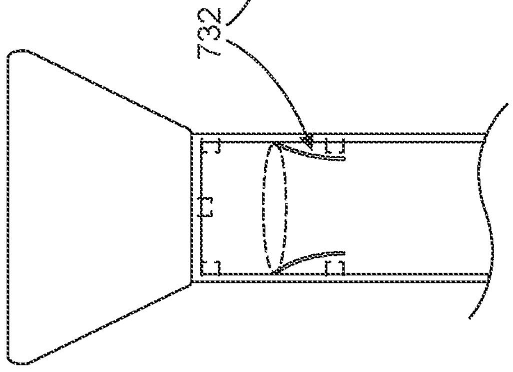
Figure 7C:
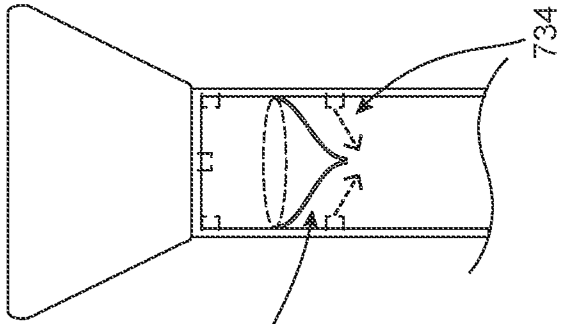

In another embodiment, referring to FIGS. 7B-7C, the thrombus removal device can include a valve 732 disposed on or within the aspiration lumen. The valve can comprise a flapper valve, a shunt valve, a duckbill valve, or the like. FIG. 7B shows the valve in the open position, and FIG. 7C shows the valve in the closed position. During normal operation of the system, the valve can remain in the open position to allow clots and other debris to be removed from the patient. In the event that a clog is detected by the system, the valve can be closed, as shown in FIG. 7C, to seal the aspiration lumen of the device. With the valve closed, irrigation jets 734 that are positioned proximal to the valve within the aspiration lumen can be activated to generate pressure behind (e.g., distal to) the clot, thereby forcing the clot out of the device and into the vacuum cannister.

Figure 7D:
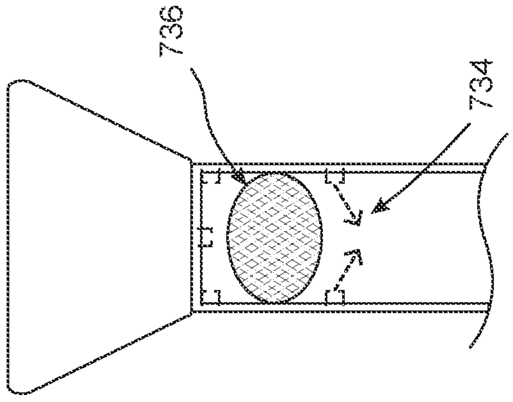

Similarly, referring to FIG. 7D, another embodiment of the device includes a distal balloon 736 that can be inflated when a clot is detected to seal the inner lumen of the device. The system can then be configured to irrigate the clogged sealed lumen with jets 734, generating pressure behind the clot as described above.

In some embodiments, a conventional vacuum pump via peristaltic or diagram pump is used, and another method of preventing blood loss by reducing vacuum pressure can be to purge or shunt the vacuum chamber when a clot or clog is removed.

Jet Control Schemes

Figure 8C:
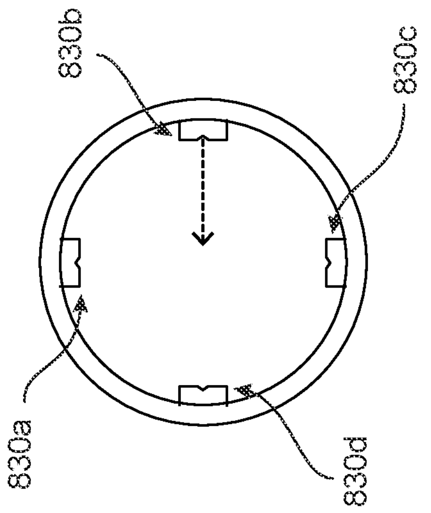
FIGS. 8A-8C illustrate one embodiment of controlling various irrigation ports of a thrombus removal system.
Figure 8B:
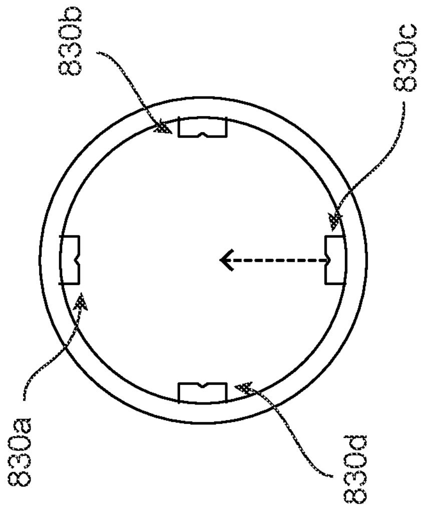
Figure 8A:
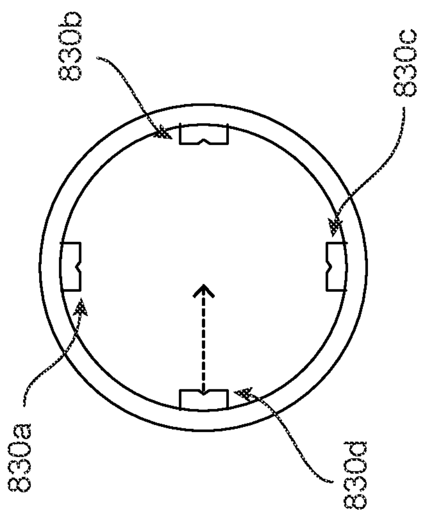

As described above, in some embodiments, fluid lumens can be distinct and separate, thereby enabling individual jets to be controlled to deliver a stream of fluid while other jets are inactive or not delivering fluid. The system can be configured to respond to pressure sensing and volume of fluid infused and removed. These control schemes can vary the amount of irrigation and aspiration as well as sequence or pulse the individual lumens to provide different cutting or declogging results. This facilitates many novel jet control schemes to be used by the thrombus removal device to assist in breaking up/macerating clots and/or removing those clots from the patient. For example, referring to FIGS. 8A-8C, a cross section of the thrombus removal device is shown with one example of a jet control scheme. In this embodiment, jets 830*a*-830*d* can each be fluidly coupled to a fluid source with an independent or distinct fluid lumen. Thus, in FIG. 8A, only jet 830*d* can be activated, allowing a stream or jet of fluid to be delivered by jet 830*d* into the aspiration lumen of the device. Similarly, in FIG. 8B, only jet 830*c* is activated, and in FIG. 8C, only jet 830*b* is activated.

It should be understood then that any number of jet control schemes can be incorporated into the treatment by the thrombus removal device when the jets are fed by independent fluid lumens. For example, referring to FIG. 8A, in one embodiment, the device could rapidly cycle sequentially from delivering jets of fluid from each of the jets (e.g., first from jet 830*a* for a preset time, then jet 830*b*, then jet 830*c*, then jet 830*d*, and so forth). Similarly, pairs or groupings of jets can be activated while other jets are inactive. For example, the jet sequence could cycle between activating only opposing pairs of jets 830*a* and 830*c* and then activating only opposing pairs of jets 830*b* and 830*d*.

While the embodiments above describe activating one or more jets in radial patterns around a circumference of the device, it should be understood that jet control schemes can also be used longitudinally along the device. For example, recall that the embodiment of FIG. 7A included a plurality of jets disposed along a length of the device. In one embodiment, a jet control scheme can be implemented in the system to rapidly cycle between jets in a distal to proximal direction (e.g., first activating the distal most set of jets, then the next most distal, and so forth until the proximal most jets are activated). It is contemplated that a control scheme in this fashion could move or urge along difficult, large, or stubborn clots to remove them from the device.

Aspiration of the system can also be pulsed or timed with the irrigation bursts to maximize effectiveness and to reduce blood loss. For example, in some embodiments, the aspiration is pulsed to coincide with jet irrigation. In other embodiments, the aspiration is pulsed or activated in between bursts of jets.

Figure 9B:
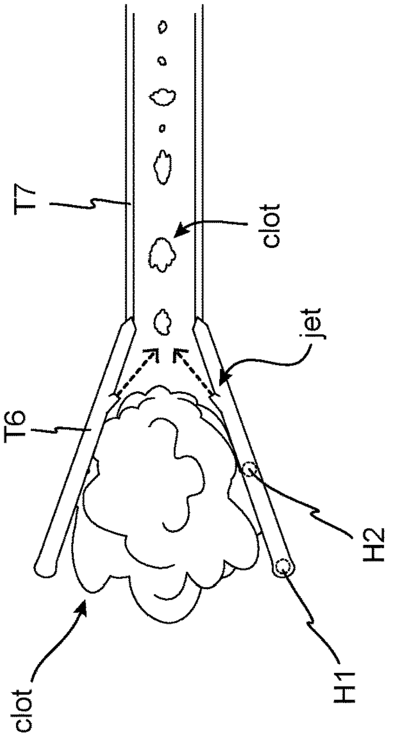
FIG. 9B is one embodiment of a thrombus removal system including one or more sensors configured to detect a clot.
Figure 9A:
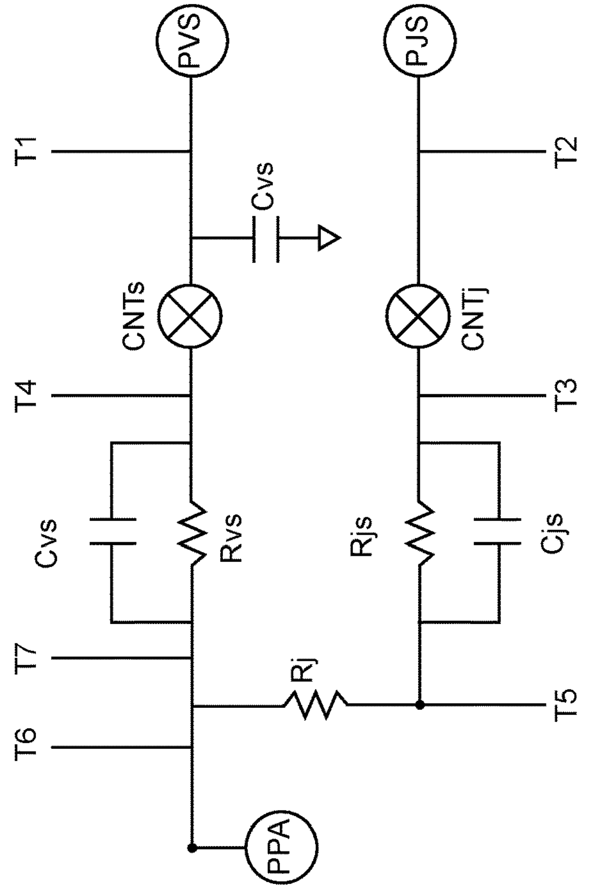
FIG. 9A is a system schematic diagram of a thrombus removal system.

FIGS. 9A-9B are schematic diagrams of the thrombus removal system and the thrombus removal device, respectively. Referring to FIG. 9A, the system can include pulmonary artery pressure (Ppa), pressure vacuum source (Pvs), pressure jet source (Pjs), fluid resistance of vacuum system (Rvs) and fluid capacitance (Cvs) of the aspiration/vacuum portion of the device, fluid resistance (Rjs) and capacitance (Cjs) of the jet portion of the device, and multiple test points T1-T7 for testing pressure or flow of the system. Any number or type of pressure and/or flow sensors can be implemented in the system. Additionally, other types of sensors can be used. For example, electrodes or impedance sensors can be used to measure an impedance at the distal end of the system (e.g., to characterize changes in electrical impedance associated with clots vs. blood). In other embodiments, temperature sensors (e.g., one or more thermistors) may be used to sense a temperature of the device or target tissue. In additional embodiments, the vacuum source or jet source can be configured as sensors, such as using back emf or a fluid column sensor connected to the aspiration lumen or jet lumen.

The pressure vacuum source (Pvs) can be a vacuum source (a trap in which a low pressure gas is maintained above the aspirant) or a positive displacement source, both of which induce a negative pressure distal to the CNTs (when present as it may not be required with a positive displacement pump). Engagement, such as with a clot, can be characterized by either the difference between an expected flow or rate in change of flow and a measured flow where that difference is of great enough magnitude.

Referring to FIG. 9B, CNTs represents the junction or connection between the pressure vacuum source and the thrombus removal device, and CNTj represents the junction or connection between the pressure jet source and the thrombus removal device. A valve in CNTs and CNTj can isolate the capacitance of the vacuum/jet source from the rest of the system such that the amount of blood drawn into the system when the vacuum system is stopped or shut down is minimized. Referring to FIG. 9A, testing points T1 and T2 can represent pressure or flow sensor locations configured to provide pressure/flow readings at a location between the pressure vacuum source and the device, and between the pressure jet source and the device, respectively. Testing points T4 and T3, similarly, can represent pressure or flow sensor locations configured to provide pressure/flow readings at a location near the junction or connection between the device and the pressure vacuum source and pressure jet source, respectively. Additionally, testing points T5, T6, and T7 can represent pressure or flow sensor locations configured to provide pressure/flow readings at a location near a distal end of the device. For example, testing point T5 can provide flow/pressure readings at or near where the jet fluid exits the jet ports or nozzles at the distal end of the device. Similarly, testing points T6 and T7 can provide pressure/flow readings of the aspiration system at or near the distal end of the device, such as within the funnel (T6 in FIG. 9B) or within the thrombus removal device just proximal to the funnel (T7 in FIG. 9B). The locations of the test points within the system schematic illustrate potential test/sensor locations for pressure sensors, flow sensors, or other sensors that could be used in real time to control operation of the device, detect system operating parameters, detect clogs, etc.

Referring to FIG. 9B, an embodiment of the thrombus removal device is shown which includes test points T6 and T7 for sensing flow and/or pressure in the funnel and the aspiration lumen of the device, and also haptic sensors H1 and/or H2 for detecting contact with a clot or other debris in the patient. In some embodiments, the haptic sensors can comprise pressure sensors (positive or negative), optical sensors, electrical impedance sensors (dc, single frequency, or spectral) or other sensors useful for the operation of the system.

Procedure and System Controls

Figures 10, 11:
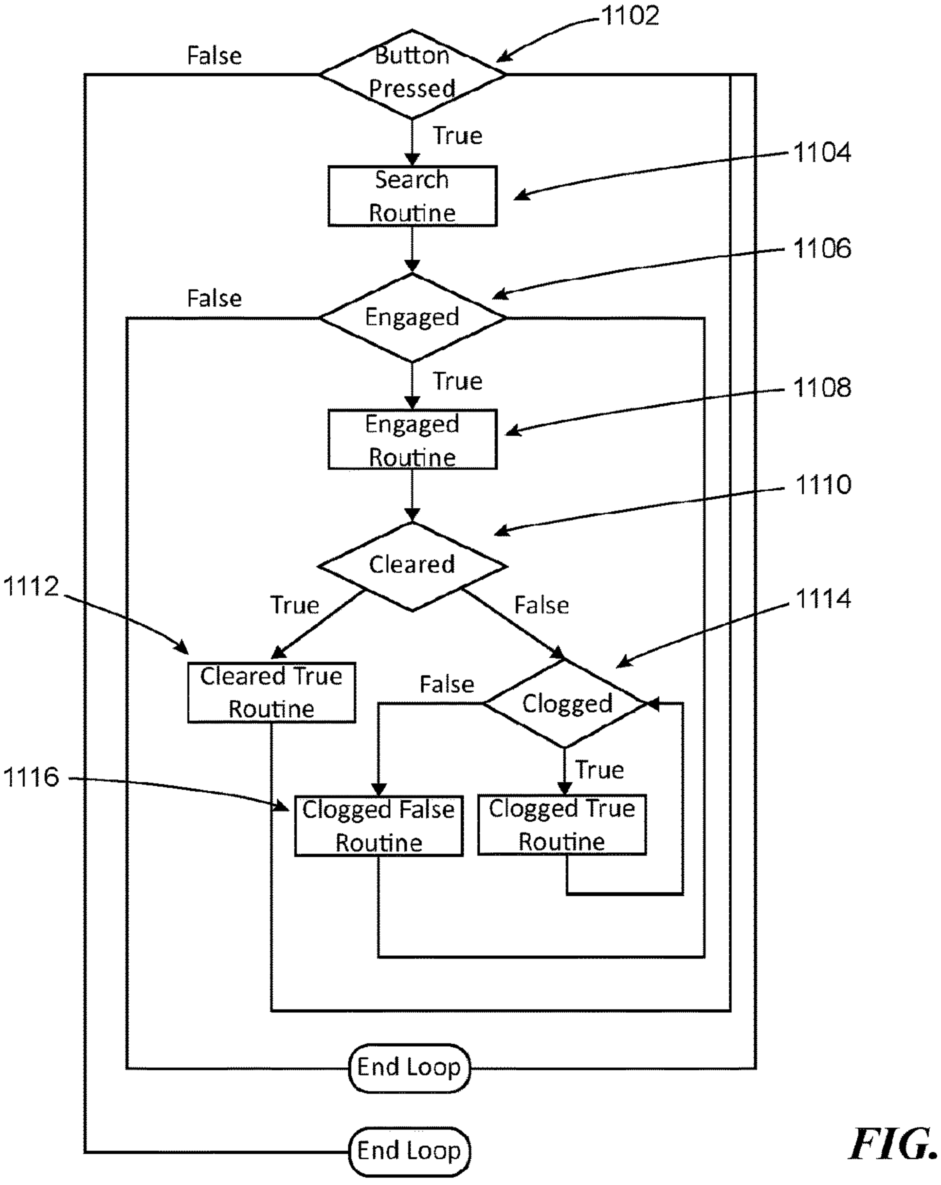
FIG. 10 is a table showing various system states of a thrombus removal system.
FIG. 11 is a procedure flow chart of various system states of a thrombus removal system.

FIGS. 10-12 illustrate procedural flow and system control schematics for a thrombus removal system according to various embodiments, including clot detection, clot engagement, and clot removal.

FIG. 10 is a table that generally describes the various states of a thrombus removal system including the associated sensor reading(s) found in each state. Generally, the thrombus removal system can include a searching for clot/no clot engaged state, an engaging clot state, a clot engaged state, a clogged jet lumen state, a clogged aspiration lumen state, and a clot initially engaged/leak state. As described above, sensors can be disposed throughout the system, including at or near a distal end of the device (e.g., at or within the funnel and/or within the aspiration lumen), at or near a proximal end of the device, and/or at or within the pressure and/or jet/fluid source outside of the device. The readings of these groupings of sensors can generally be used to determine which state the thrombus removal system is in, and can be further used to inform and control the device into subsequent states throughout the therapy. Referring to the table in FIG. 10, when the sensors are in a nominal or (+) state it reflects a signal indicative of engagement with a clot, and when the sensors are in a non-nominal or (−) state it reflects a signal indicative that the device is not in engagement with a clot. In some embodiments, the nominal state can correspond to a sensed parameter within a given range (e.g., a specific pressure or flow rate range) and the non-nominal state can correspond to a sensed parameter (e.g., pressure or flow rate) beyond a threshold pressure. In one embodiment, a nominal range for pressure can be between approximately +4 to −25 inHg.

For example, referring to the table of FIG. 10, when the thrombus removal system is in a searching for clot/no clot engaged state, all of the sensors including the distal sensors, the proximal sensors, and the source sensors can be in a non-nominal state. However, when the system is engaging a clot, both the source sensors and the distal sensor(s) can be in a nominal state, with the proximal sensor(s) remaining in a non-nominal state. When the thrombus removal system is in a clot engaged state, all of the sensors will be in a nominal state, as shown in FIG. 10.

The sensors can also inform errors in the system, including clogged lumens (aspiration or jet lumens) as well as leaks in the system. For example, still referring to FIG. 10, source and proximal sensors in a nominal state and distal sensors in a non-nominal state can indicate that one or more of the jet lumens is clogged. Similarly, source sensors in a nominal state and proximal/distal sensors in a non-nominal state can indicate a clogged aspiration lumen or lumens. Finally, proximal and distal sensors in a nominal state and the source sensor(s) in a non-nominal state can indicate a leak in the system, or that a clot has initially been engaged. Further details on the sensors, their measurements, and how the system determines the system state based on measurements will be discussed below.

FIG. 11 is a flowchart that describes the various system states that a thrombus removal system may cycle through during a thrombus removal procedure. Referring to step 1102 of the flowchart, the thrombus removal system or device can be inserted into a patient's vasculature and a distal end of the device can be advanced and delivered to the target tissue site that includes one or more thrombi. At this point, the user of the device can actuate, press, or initiate a clot searching routine in the thrombus removal system at step 1104 (e.g., such as by pressing a button on a handle or on a generator of the system). In some embodiments, the system can initiate the clot searching routine automatically.

When the thrombus removal system is actively in the clot searching routine of step 1104, the system is monitoring various sensors (such as flow or pressure sensors) to determine if/when the thrombus removal system has engaged with a thrombus or thrombi at the target tissue location. While in this clot searching state, the system can operate the aspiration source to pull vacuum and assist in capturing clots in the funnel of the device. In some embodiments, the aspiration can run at a normal level (e.g., the same level of aspiration that runs when a clot is being removed) and in other embodiments the aspiration can run at a lower level or some minimal level. In this state, the jets can be completely off or can also run at a lower or minimal level to assist with clot capture. As described above, the system can include any number of pressure and/or flow sensors located at several locations on or within the system. The system can also use the jet ports/jet lumens as sensors, which can inform the system about the particular state and guide the therapy process.

Figure 12A:
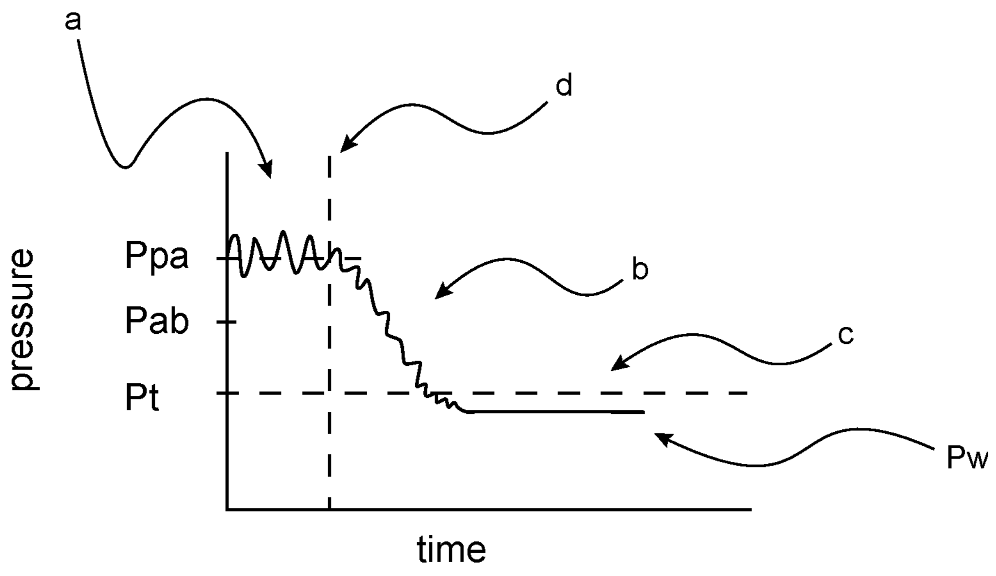
FIGS. 12A-12B illustrate pressure waveform graphs during a clot engagement state.

FIG. 12A illustrates a pressure waveform Pw of distal sensors of a thrombus removal system, such as distal sensors located on or within a funnel or distal lumen of the device, or alternatively, using the jet ports or lumens as distal pressure sensors (under negative pressure relative to local pressure at the jet aperture/no aspiration). This allows for the measurement with lower flows than required for the aspiration lumen. Referring to the diagram of FIG. 12A, Ppa is the pressure of the pulmonary artery, Pab is the pressure at ambient or atmospheric, and Pt is a predefined pressure threshold. Various regions of the pressure wave Pw are shown, including: a, which indicates that the device is not engaged with a clot and is measuring heart induced pulmonary artery fluctuations, b, which indicates that the sensed pressure is dropping as a function of engagement with a clot, c, which indicates that pressure is below the predefined threshold Pt where fluctuations are masked, and d, which indicates either the time at which the pressure source is activated and/or the time at which the device begins to interface with a clot.

Many features of the pressure wave Pw in FIG. 12A can be used or identified to indicate that the device has engaged with a clot. Typically the Ppa is measured prior to engagement with a clot, to provide a baseline for pressures at the target tissue location. In one embodiment, when the pressure wave Pw drops below the predefined pressure threshold Pt, it can indicate to the system that a clot has been engaged. This can result in the system state moving to the engaged state 1108 in FIG. 11. Additionally, the system state can move to clot engaged if pressure fluctuations disappear or fall below a threshold value as in some percentage of region a of the pressure waveform. In another embodiment, if the rate of change in region b of the pressure waveform is greater than a threshold level, the system state can move to engaged. The rate of change in region b can provide information on the quality of engagement such as; fewer or more ports engaged at the level of the ports, essentially if all ports are engaged by clot the |DP/dt| as the capacitance of the system will be smaller. Any combination of the above conditions can result in the system identifying or determining that a clot is engaged in the funnel at the distal end of the device.

Figure 12B:
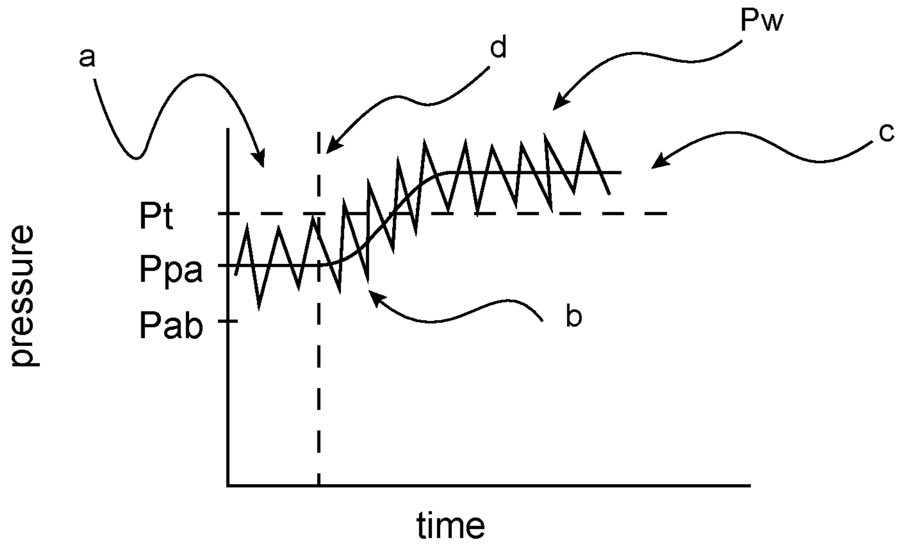

FIG. 12B illustrates a pressure waveform Pw of distal sensors of a thrombus removal system, such as distal sensors located on or within a funnel or distal lumen of the device, or alternatively, using the jet ports or lumens as distal pressure sensors (under low positive pressure/aspiration on). Once again, the diagram includes various regions of the pressure wave Pw, including: a, which indicates that the device is not engaged with a clot and is measuring heart induced pulmonary artery fluctuations, b, which indicates that the sensed pressure is rising as a function of engagement with a clot, c, which indicates that pressure is above the predefined threshold Pt where fluctuations are masked, and d, which indicates either the time at which the pressure source is activated and/or the time at which the device begins to interface with a clot. In FIG. 12B, engagement is determined when the pressure of the pressure waveform Pw increases above the aspiration pressure as the clot presses against the distal pressure sensors (e.g., jet ports or purpose-built ports or sensors not used for jetting).

In addition to the pressure changes measured by the sensors and described above in FIGS. 12A-12B, engagement of a clot can be identified when the pressure change is mediated by one or any combination of the following scenarios:

1) a flow induced in the aspiration line either towards or away from the pressure vacuum source (Pvs). As described above, the Pvs may be configured as pressure source such as a vacuum trap or as a positive displacement pump or a combination thereof.
2) a flow induced in one or more of the jet lines, either towards or away from the pressure jet source (Pjs). The Pjs may be a configured as pressure source such as a volume of fluid maintained under pressure or periodically pressurized or as a positive displacement pump or a combination thereof.
3) a change in electrical impedance measured by distal electrodes or impedance sensors.
4) a change in any combination of the above.

The flows described above in 1) and 2) may be induced by a number of conditions, including a relatively constant delta P across the line or a pulsating pressure across the line. In some embodiments, the pulsations are configured to minimize the total volume of fluid displaced into or out of the system. For example, a small volume of fluid (e.g., 1-10 mL) can be drawn in and out of the aspiration line with the pulsations. In this example, the dQ/dt is larger for the inflow than the outflow to enhance fluid drag to coax the clot into the funnel. An engagement is indicated by an abrupt increase in pressure and/or flow. In another example, a smaller volume of fluid (e.g., 0.1-1 mL) can be drawn into the jet line or port. In this example, an engagement is indicated by a decrease in the pressure and/or in flow. In yet another embodiment, engagement of a clot can be determined by discharging a volume of fluid at a constant flow rate through the jet while the aspiration is drawing fluid into the system and noting a pressure increase on the pressure line, wherein the engagement is indicated by an increase in the pressure and/or flow.

When engagement with a clot is sensed, as described above, the system can move to the engaged routine/clot removal state as shown in FIG. 11. First, to confirm engagement, the system can turn off jet flow (if active) and decrease the aspiration pressure to less than Pa_on (e.g., 10 in Hg absolute) and test the rate of |dPa/dt|. If this tested rate is |dPa/dt|>/=Pa_on/1 sec the system can begin aspiration and jetting to remove the clot. However, if that condition is not met, the testing can continue. If repeating the testing does not result in confirmed engagement, then the system can be removed.

During the clot removal/engaged state, the system can continue to sense maintained engagement with a clot, as indicated by maintenance of Pa<Pa_on. With maintained clot engagement, the jets of the thrombus removal system can be activated to provide an average fluid velocity Vjet of greater than 10 m/s (and optionally greater than 20 m/s or greater than 40 m/s). The jet flow from the jets can be any combination of pulsatile with a non-zero minimum, pulsatile with a zero minimum, constant, or negative minimum.

The Pa can continue to be monitored during clot removal. If Pa>Pa_on, system changes can include either turning off the jets and returning to clot engagement functions (as described above), or alternatively, incrementally decreasing jet average velocity Vjet. If the Vjet<Vjet minimum, the system can return to clot engagement. If during continued monitoring Pa<Pa_on, then the clot removal process can continue.

In some embodiments the system can monitor Qasp (flow in the aspiration line) and Qjet (flow in the jet line) and or calculate Q's from system resistances and capacitances. In this embodiment, if Qjet>/=Qasp the system can return to engagement or else can continue with clot removal.

After the engaged routine has progressed, referring to FIG. 11, at step 1110 the system can move to determine if the clot has been cleared. If the system determines that the clot has been cleared at step 1112, then the process flow chart can revert to the pre-search routine state in which the system is neither actively looking for a clot or actively attempting to engage/remove a clot. In general, however, the cleared state or occlusion testing procedure includes assessing or monitoring blood flow past the distal end of the thrombus removal system to assess improvement in blood flow (as a result of clot removal). In addition to using flow or pressure sensors to identify an increase in flow, other techniques can be used by the system. For example, in some embodiments, flow monitoring can be accomplished using thermal dilution and or time of flight. For example, a volume of cold fluid (e.g., colder than body temperature) can be delivered into the target tissue location and the temperature can be monitored at another sensor location. For example, the cold fluid can be delivered at testing location T7 (FIG. 9B) and temperature can also be measured at testing location T6. Alternatively, a heated fluid can be delivered at T7 and temperature can be monitored at T6. In another embodiment, a contrast agent can be injected by the system into the target location through the jetting system or through purpose build lumens, and the contrast agent can be visualized to determine whether or not the clot was removed.

If, however, the system determines that the device is either clogged or the clot has not been cleared, at step 1114 the system can engage in a clogged or clearing routine to attempt to de-clog the device or remove the clot. The clearing/clogging protocols have been previously described in this disclosure, but in general the system can use any number of procedures including continuing to run aspiration/jets, reversing the pressure of the aspiration and/or jets, running aspiration without jets or jets without aspiration, or any other number of clearing or clogging routines. If the system determines that the clot has been cleared at step 1116, then the process flow chart can revert to the pre-search routine state in which the system is neither actively looking for a clot or actively attempting to engage/remove a clot.

Figure 13:
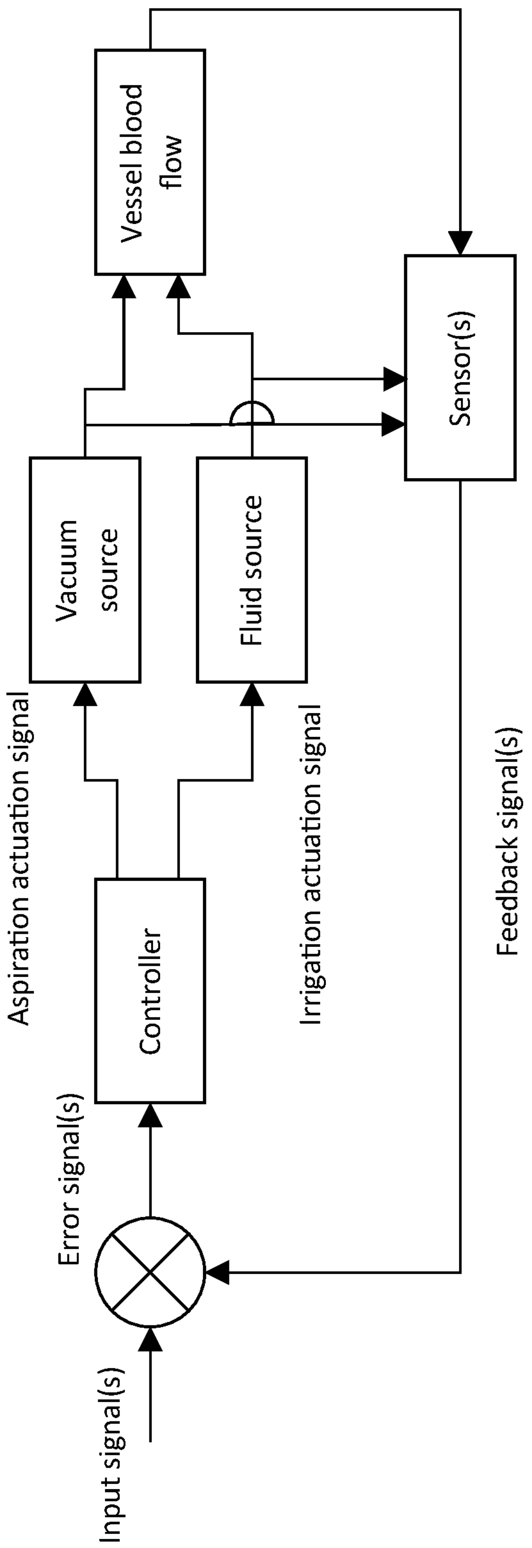
FIG. 13 is a simplified system schematic of a thrombus removal system.

FIG. 13 is a simplified system schematic that describes the system elements of a thrombus removal system that are required to implement the procedures and methods described above. In general, the system can include an electronic controller configured to control operation of both a vacuum/aspiration source and a fluid (jet) source of the system. Sensors can be located throughout the system, including within the vacuum/fluid source and within the device (both proximal and distal). As described above, the sensors can include pressure, flow, impedance, etc. sensors. Sensor measurements can be input back into the controller along with error signals to control operation of the device. Vessel blood flow can also be monitored to assist in determining when a clot has been cleared or engaged.

In contrast to the embodiments described above which use pressure sensing or pressure waveforms to assist in control schemes of the device, in other embodiments the device can control system states based on flow measurements within the system, such as aspiration flow rates or irrigation flow rates. Additionally, any of the control schemes described herein can be combined with another. For example the pressure control schemes can be combined with the flow control schemes. As described in FIGS. 9A-9B and above, multiple test points T1-T7 can be provided in the system for testing flow within the system. Any number or type of flow sensors can be implemented in the system at the testing points, or at other points in the system, particularly in the funnel and in the aspiration lumen(s) of the device.

Figure 14:
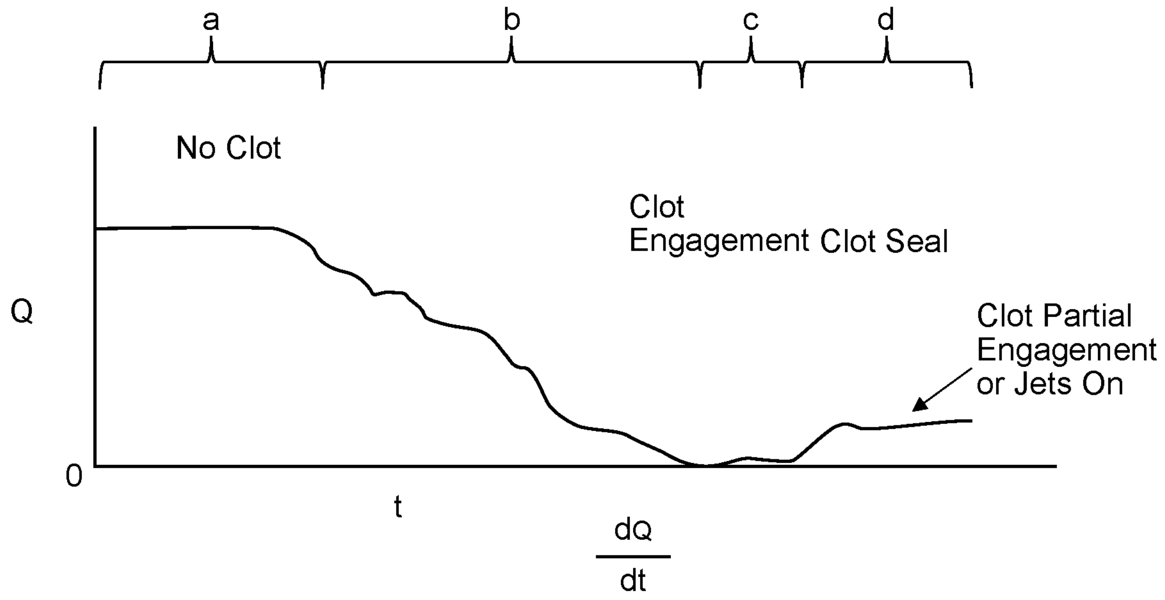
FIG. 14 is one embodiment of a flow waveform of a thrombus removal system.

FIG. 14 illustrates an aspiration flow (Q) waveform that can be sensed by one or more flow sensors located within the system, such as at test points T1-T7, but specifically sensors associated with aspiration flow (e.g., test points T1, T4, T6, and T7). The waveform of FIG. 14 shows the flow of aspiration over time as the system hunts or looks for a new clot, engages the clot, and begins treatment/removal of the clot. Many features of the flow wave Q in FIG. 14 can be used or identified to indicate that the device has engaged with a clot and provide insight into the clot behavior within the device including within the funnel. Any determinations that the system makes as a result of the measured flow wave Q can be indicated to the user. For example, the system can indicate to the user (e.g., with a display, an indicator, or an audio signal) that the system is partially engaged, fully engaged, or not engaged with a clot. Typically the Q is measured prior to engagement with a clot, when aspiration is activated either at a clot engagement level or at some aspiration flow level lower than a clot engagement level (e.g., a clot seeking level), to provide a baseline for flow at the target tissue location. It should be noted that as shown in the embodiment of FIG. 14, aspiration is activated but the water jets have not yet been activated. In other embodiments, however, the water jets may be activated during any of the phases of the curve illustrated in FIG. 14. The flow Q while the system is looking for a clot is shown in region a of the waveform in FIG. 14.

In FIG. 14, when the flow wave Q begins to drop, as shown in region b, the measured flow can indicate to the system that a clot has been engaged. In some embodiments, the slope dQ/dt of the flow waveform can be used by the system to determine if there is clot engagement. In some embodiments, the rate or slope of the flow waveform can be indicative of the "quality" of engagement with a clot. For example, the greater the rate of decline, the larger the resistance (decrease in flow path around the clot) induced by the interface between clot and funnel. Actual rates will be dependent on system parameters such as component volumes, and dimensions, source flow rates, component capacitances, and or pressures. Eventually, the flow wave Q will go to approximately zero (or some non-zero minimum), as shown in region c of FIG. 14, indicating that the clot is fully engaged within or seated within the funnel of the device. This can result in the system state moving to the engaged state 1108 in FIG. 11. Additionally, the system state can move to clot engaged if pressure fluctuations disappear or fall below a threshold value as in some percentage of the flow waveform. For example, section d of the wave in FIG. 14 is slightly above zero, but is below a threshold that indicates to the system that the clot is engaged or partially engaged. This above zero flow can also be a result of turning on the jets, or can also be caused by the clot moving around not being fully engaged within the funnel of the device.

The rate of change in region b can provide information on the quality of engagement. Any combination of the above conditions can result in the system identifying or determining that a clot is engaged in the funnel at the distal end of the device.

Figure 15:
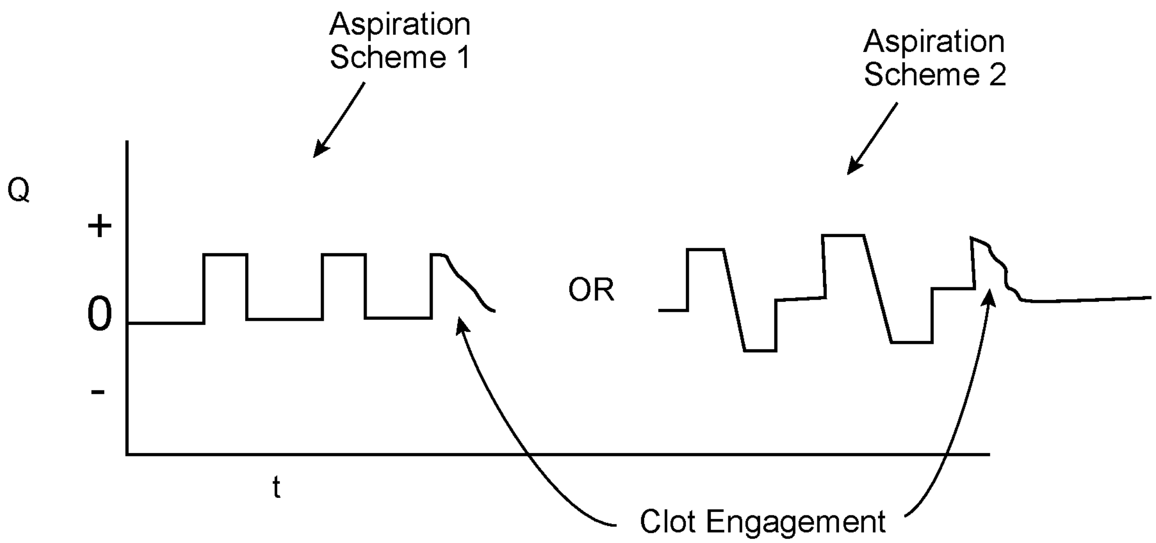
FIG. 15 illustrates an aspiration scheme of a thrombus removal system.

Now referring to FIG. 15, in some embodiments the aspiration can be pulsed while looking for a clot (or prior to clot engagement) to reduce the amount of blood drawn into the system. An aspiration waveform at the aspiration source can also be monitored and used to determine when the system has engaged with a clot. FIG. 15 illustrates two aspiration pulsing schemes that can be used with the thrombus removal system. Positive flow (+) in this diagram indicates positive flow in the direction of the aspiration source. In Aspiration Scheme 1, shown on the left of FIG. 15, the aspiration can be pulsed or cycled between 0 flow Q and positive flow Q, resulting in the illustrated square wave as shown. In this example, the square wave begins to deteriorate or slope towards zero in the third pulse, indicating to the system that a clot has been engaged. Therefore, in this embodiment, pulsing the aspiration and monitoring the resulting aspiration flow waveform can allow the system to determine when a clot is engaged by the thrombus removal device. In Aspiration Scheme 2, shown on the right side of FIG. 15, the aspiration is still pulsed, but instead of pulsing between 0 flow and positive flow as in Aspiration Scheme 1, instead in Aspiration Scheme 2 the pulsing sequence transitions from positive flow to 0 flow to negative flow and back to 0 flow, as shown. In this embodiment, a clot can be detected as engaged in the same manner as described above in Aspiration Scheme 1. The function of the negative flow waveform is to push fluid back out of the device. When the device is hunting or searching for a clot, this negative pulsing waveform can result in less or limited blood being aspirated into the system and removed from the patient. The illustrated waveforms are on example, however it should be understood that other waveforms can be used such as triangular waveforms, sinusoidal waveforms, or "purpose built" waveforms.

Figure 16B:
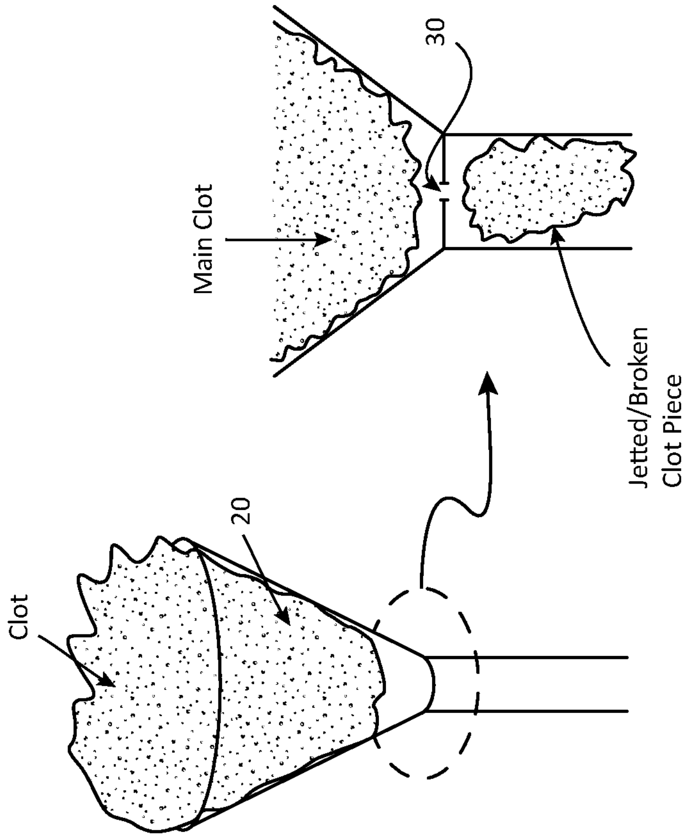
FIGS. 16A-16D illustrate one embodiment of a thrombus removal system.

The injection of fluid into the system from the jets when a clot is engaged in the funnel of the thrombus removal device creates additional challenges for maintaining clot engagement in the funnel. For example, if a clot is fully engaged in the funnel and an injection of fluid or water is added to the system with jets 30 (in FIG. 16B), the clot can be permanently or temporarily dislodged from the funnel if the aspiration system is incapable of maintaining the negative pressure across the clot or if the momentum of the jet fluid impacting the clot is great enough to overcome the pressure gradient retaining the clot. FIG. 16B shows that when the jets 30 are activated with a main clot in the funnel, a small piece of the main clot can be broken, macerated, or severed from the main clot and aspirated into the aspiration lumen of the device. FIG. 16C shows a partially engaged clot.

Figure 16A:
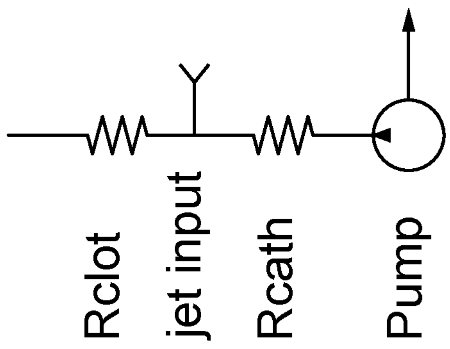
Figure 16C:
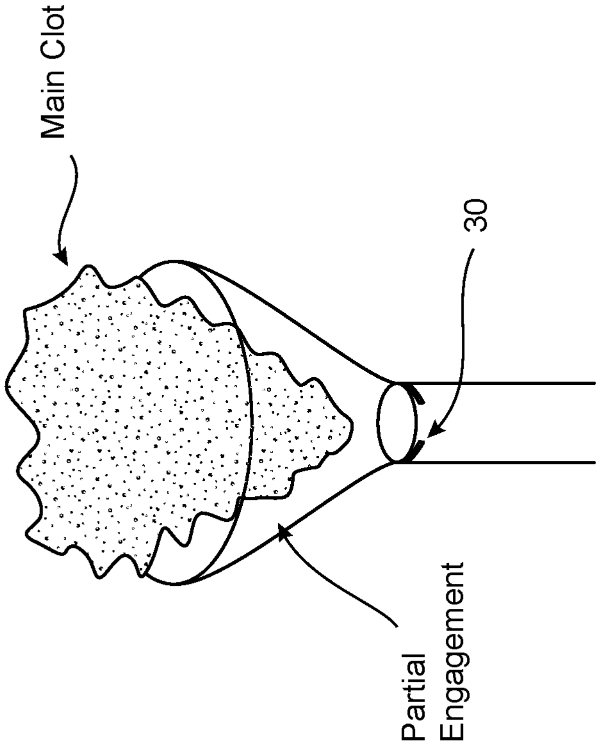

Referring still to FIGS. 16A-16C, the device when engaged with a clot can be schematically illustrated as having a resistance $R_{clot}$ in the funnel distal to the jets and a resistance $R_{cath}$ in the catheter proximal to the jets. The resistance $R_{clot}$ varies as a function of engagement, so this resistance is higher when the clot is fully engaged and lower when the clot is partially or not engaged with the funnel. This resistance, and therefore clot engagement, can be detected by the system using the aspiration/flow controls described above.

Figure 16D:
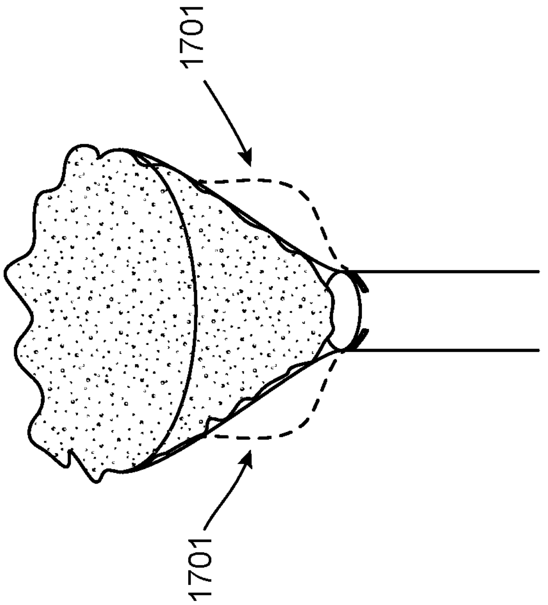

In some embodiments, referring to FIG. 16D, one or more compliant sections or easily deformed sections 1701 can be added to the funnel or to the catheter at or near where the jets inject fluid into the device. These compliant section(s) 1701 can be of a more compliant material than the surrounding portions of the device including the funnel. The compliant section(s) 1701 can be specifically designed and configured to expand when the bolus of fluid is injected by the jets into a fully contained or engaged clot. The compliant sections allow the jets to be turned on with fully engaged clots without dislodging the clot from the funnel thereby minimizing the chance that the clot becomes partially of full disengaged.

Control schemes for injecting fluid into the clots with the device are also provided that advantageously assist with clot engagement. Referring to FIG. 17, an irrigation/jet pump cycle can include a plurality of different pumping sequences. For example, a given pump cycle Pc or irrigation cycle may include a pump cycle a, pump cycle b, and pump cycle c, with Pc=a+b+c. When the irrigation is turned on, pump cycle b can be implemented in which water or fluid is injected from the jets towards an engaged clot at a velocity of greater than 10 m/s and up to 40-75 m/s or higher. This initial bolus of fluid from the jets at a high velocity (e.g., 10 m/s to 40 m/s) is intended to penetrate and break off a small portions of the main clot such that they can more easily be aspirated into the device with the aspiration system. Still referring to FIG. 17, once the small portion of clot has been broken off from the main clot with the initial bolus of fluid, pump cycle c can be implemented wherein the jets inject fluid at a lower flow rate than in pump cycle b to assist with aspiration/transportation of the broken-off portions of clot into the aspiration system. In one embodiment, the flow rate of irrigation from the jets in pump cycle c can be less than 10 m/s. The duration of the various pump cycles can be fine tuned and adjusted based on the specific treatment, including the clot size, clot type, clot hardness, etc. In some embodiments, it may be desirable to irrigate at the higher flow rate of pump cycle b for a longer period of time to break off large or stubborn/hard clots. However, this results in adding more volume of fluid into the system, so the system must include sufficient compliance built-in to avoid dislodging the clots from the funnel. In other embodiments, pump cycle b is only run for a short period of time to break off a portion of clot, and then the system can cycle to pump cycle c to assist in aspirating the pieces or portions of clot.

In some embodiments, referring to FIG. 18, a valve can be added to the aspiration system to allow for large capacitances at the vacuum/aspiration source and full pressuring at the application of aspiration in the funnel. FIG. 18 schematically illustrates this configuration, in which the valve is added near the aspiration source.

Additional funnel designs are also provided. In one embodiment, referring to FIGS. 19A-19B, the funnel 20 can include expandable struts 2001 that surround compliant funnel section 85 configured to provide additional compliance into the funnel. The compliant funnel section can be similar in function to 1701 described in FIG. 16D, which can prevent clot disengagement when a bolus of fluid from the jets is added into the funnel. FIG. 19B is a top down view of the funnel 20 with the struts. In some embodiments, the struts and/or funnel can include strain sensors configured to sense engagement with a clot. Alternatively, the strain sensors can determine when a clot is partially engaged or is becoming dislodged from the funnel, such as by detecting when the clot moves from a fully engaged situation to a partially engaged situation. Additionally, the strain gauges can be configured to sense deformations within the funnel or the struts indicative of clot interface resistance changes.

Figure 20A:
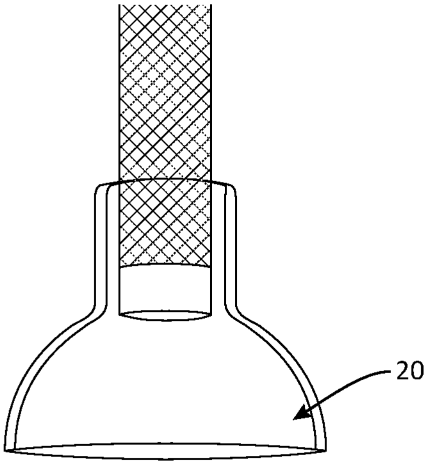
FIGS. 20A-20B illustrate a thrombus removal system with a hemispherical funnel.
Figure 20B:
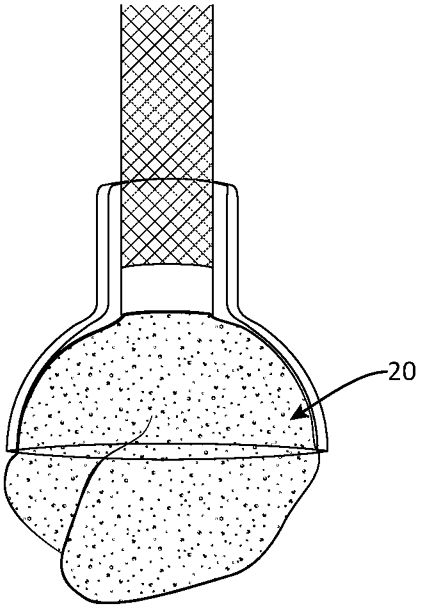

In FIGS. 20A-20B, an alternative funnel design is provided. In contrast to the conically shaped funnels described above, the funnel of FIGS. 20A-20B provides a hemispherical shape. In some examples, this configuration is configured to enhance clot engagement during jet/aspiration and/or minimize collapse of the distal engagement or capture portion that can be encountered in conically shaped funnels.

Assessing the Effectiveness/Completion of Treatment

Systems and methods are provided herein for assessing the effectiveness and/or completion progress of thrombectomy treatment. In some embodiments, the methods can be implemented entirely in software that resides on the thrombectomy device itself or is in communication with the device. In other embodiments, the methods can be implemented in combination with hardware disposed on or in the device that provides additional information to the system/device on treatment progress.

Figure 21:
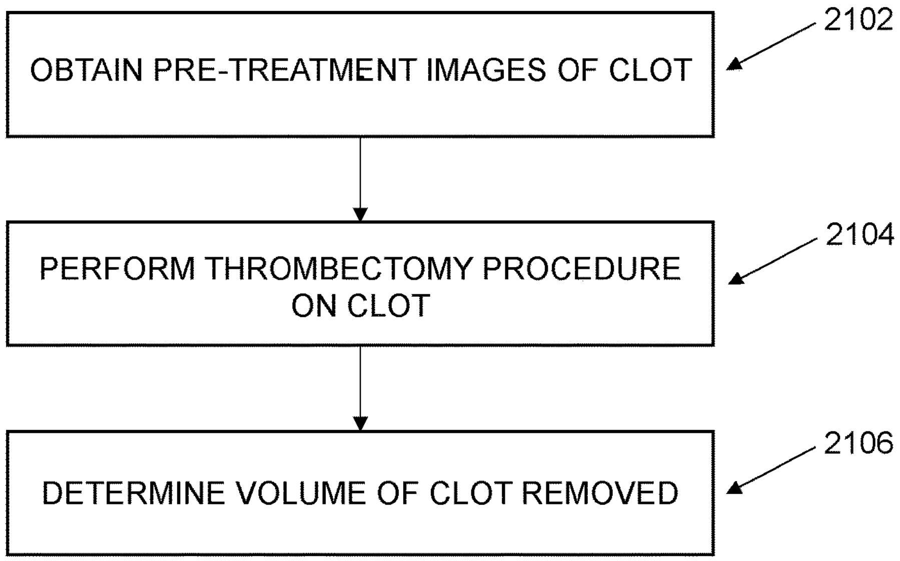
FIG. 21 is a flowchart describing a method of assessing a volume of clot removed during treatment.

In one embodiment, a method of assessing the effectiveness or monitoring the progress of treatment can include assessing or determining the volume of clot removal based on pre-treatment imaging (e.g., CT). Referring to the flowchart of FIG. 21, the method can include, at step 2102, obtaining pre-treatment images of the clot to be removed or treated. In some embodiments, this can include obtaining $CT^{images}$, ultrasound images, MRI images, or any other high resolution or high quality images of the target clot.

At step 2104, the method can then include performing a thrombectomy procedure on a targeted clot or clots using any of the devices and methods described herein.

Next, at step 2106, the method can include determining or calculating the volume of clot removed from the patient during the thrombectomy procedure. In some embodiments, this determination is done entirely in software, such as with algorithms that compare pre-treatment imaging to post-treatment imaging, determine the volume of pre-treatment clot to post-treatment clot, and identify the volume or percentage of clot removed.

In other embodiments, the determination can be based on sensor feedback from the thrombectomy device. For example, flow and/or pressure sensors outside the thrombectomy device or alternatively inside the aspiration lumen of the device can be used to measure or estimate the amount of clot removed in real-time. Alternatively, contrast agent can be delivered into the target region during treatment, such as with the jets or alternatively with a separate contrast agent lumen to allow for real-time imaging of the clot removal. In some embodiments, the contrast agent can be delivered from or near the funnel of the device. In some embodiments, additives can be added to the contrast agent which can adhere to the clot(s) and show when the clots are removed under real-time imaging. This can then enable software or image processing solutions to estimate or determine the amount of clot removed during therapy.

In some embodiments, completion of the treatment can be determined or assessed based on a scoring system that is a composite of performance parameters (e.g., volume removed per step 2106 above) and/or physiological parameters (Sp02 increase/decrease, HR, respiratory rate, etc. recovering to normal ranges).

Figure 22:
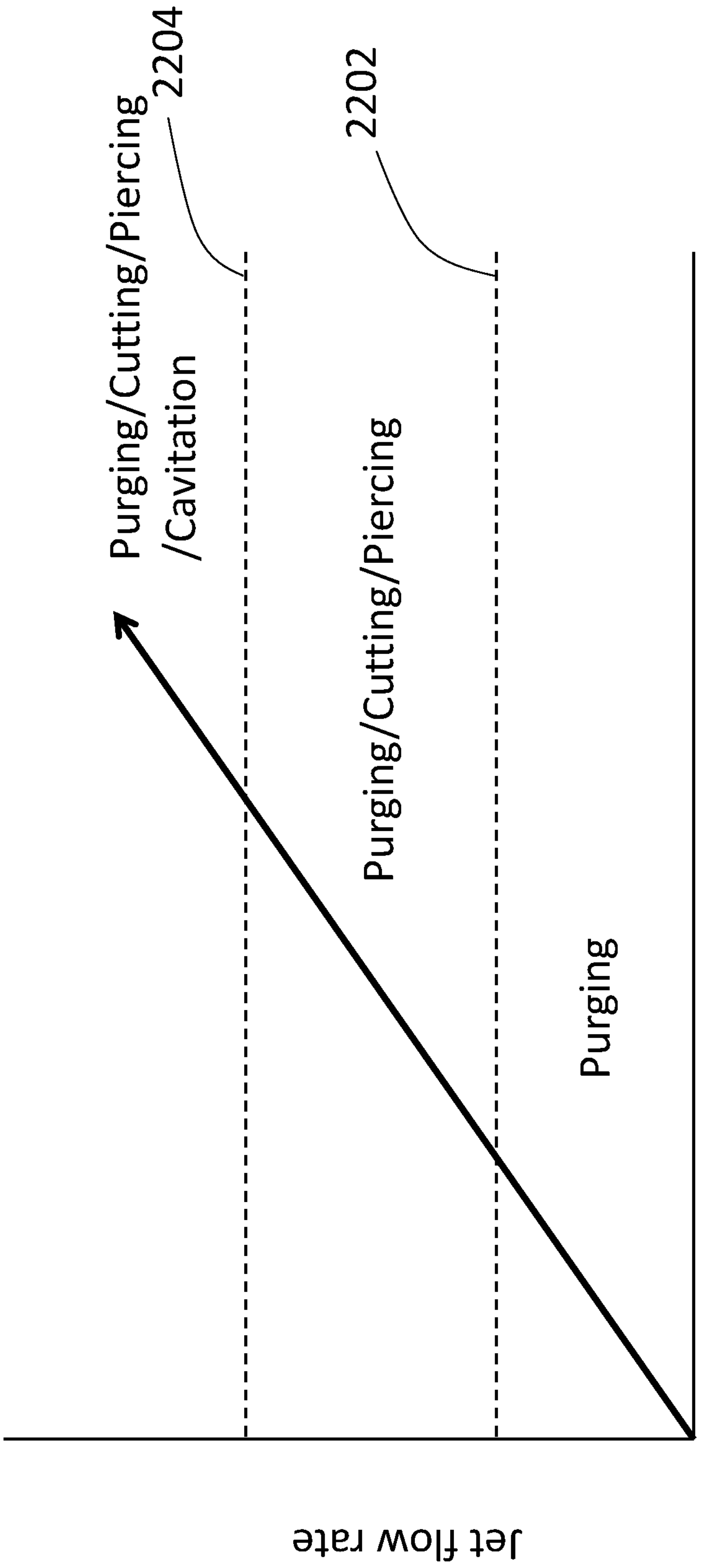
FIG. 22 is a flowchart describing various mechanisms of action of the fluid streams disclosed herein.

Referring to FIG. 22, a chart is provided that illustrates the relationship between the exit velocity or flow rate (avg.) of the jet(s) and the mechanism of action with one or more thrombi engaged with the thrombus removal device (i.e., engaged in the funnel or with the aspiration lumen). Generally, at lower jet flow rates (e.g., below 10 m/s depending on different parameters like the formulation of the clot and the jet configuration), the jets serve to assist with purging of the thrombus or thrombi into the aspiration lumen (especially when the funnel is occluded or partially occluded by the clot). This purging can include the function of pushing the thrombus into and or through the aspiration lumen and also providing fluid into the funnel and into the aspiration lumen to assist with clot removal. The purging may also assist with breaking up soft, loose material on the surface of the clot but it will not be able to break through harder material. However, once the jet flow rate begins to exceed a cutting threshold 2202, in addition to purging, the jets begin to cut the thrombus or thrombi surface to break the thrombus into small fragments which can then be more easily aspirated into the aspiration lumen of the thrombus removal device. It has also been found that at sufficiently high velocity the jet(s) will pierce the clot surface and penetrate through to the inner part of the clot. In some embodiments, the threshold comprises a jet flow rate that ranges from 10-12 m/s. In other embodiments, an ideal cutting or piercing flow rate of the jets range from 10-15 m/s, or alternatively, from 12-15 m/s. When the jet flow rate begins to exceed a cavitation threshold 2204, in addition to purging and cutting, the jets, either individually or due to the interaction with one or more other jets, can be configured to produce cavitation within the clot or within the funnel of the device, as described above. As described herein, in some embodiments, cavitation is formed with jet flow rates over 15 m/s, over 20 m/2, from 15-90 m/s, from 20-90 m/s, or from 50-90 m/s. Flow rates higher than 90 m/s can also be used to generate cavitation.

While the embodiments herein have been described as being intended to remove thrombi from a patient's vasculature, other applications of this technology are provided. For example, the devices described herein can be used for breaking up and removing hardened stool from the digestive tract of a patient, such as from the intestines or colon of a patient. In one embodiment, the device can be inserted into a colon or intestine of the patient (such as through the anus) and advanced to the site of hardened stool. Next, the aspiration system can be activated to engage the hardened stool with an engagement member (e.g., funnel) of the device. Finally, the jets or irrigation can be activated to break off pieces of the hardened stool and aspirate them into the system. Any of the techniques described above with respect to controlling the system or removing clots can be applied to the removal of hardened stool.

As one of skill in the art will appreciate from the disclosure herein, various components of the thrombus removal systems described above can be omitted without deviating from the scope of the present technology. As discussed previously, for example, the present technology can be used and/or modified to remove other types of emboli that may occlude a blood vessel, such as fat, tissue, or a foreign substance. Further, although some embodiments herein are described in the context of thrombus removal from a pulmonary artery, the disclosed technology may be applied to removal of thrombi and/or emboli from other portions of the vasculature (e.g., in neurovascular, coronary, or peripheral applications). Likewise, additional components not explicitly described above may be added to the thrombus removal systems without deviating from the scope of the present technology. Accordingly, the systems described herein are not limited to those configurations expressly identified, but rather encompasses variations and alterations of the described systems.

Conclusion

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A thrombus removal device, comprising:

an elongate shaft comprising a distal end;

an aspiration lumen within the elongate shaft;

a vacuum source in communication with the aspiration lumen configured to generate suction within the aspiration lumen to engage a target thrombus with the distal end;

at least one fluid lumen in the elongate shaft; and two or more apertures disposed within the distal end, the two or more apertures in fluid communication with the at least one fluid lumen and configured to generate and direct two or more fluid streams that intersect at an intersection point within the aspiration lumen, the two or more fluid streams having a flow rate and proximity sufficient to induce cavitation at the intersection point that is configured to mechanically morcellate the target thrombus engaged with the distal end.

2. The thrombus removal device of claim 1, wherein the two or more fluid streams each have a flow rate ranging between 50 m/s and 90 m/s.

3. The thrombus removal device of claim 1, wherein the two or more fluid streams each have a flow rate of at least 50 m/s.

4. The thrombus removal device of claim 1, wherein fluid flowing within the at least one fluid lumen at a lumen flow rate of 3 m/s results in the two or more fluid streams having a flow rate of at least 50 m/s.

5. The thrombus removal device of claim 1, wherein fluid flowing within the at least one fluid lumen at a lumen flow rate of 4 m/s results in the two or more fluid streams having a flow rate of at least 70 m/s.

6. The thrombus removal device of claim 1, wherein fluid flowing within the at least one fluid lumen at a lumen flow rate of 5 m/s results in the two or more fluid streams having a flow rate of at least 90 m/s.

7. The thrombus removal device of claim 1, wherein the intersection point comprises a focal point of the two or more fluid streams.

8. The thrombus removal device of claim 1, wherein the two or more fluid streams are generally orthogonal to a longitudinal axis of the elongate shaft.

9. The thrombus removal device of claim 1, further comprising a cavitation detection sensor disposed on or within the thrombus removal device.

10. The thrombus removal device of claim 9, wherein the cavitation detection sensor is disposed on or within a funnel at the working end of the thrombus removal device.

11. The thrombus removal device of claim 9, wherein the cavitation detection sensor is disposed on or within an aspiration lumen at the distal end of the thrombus removal device.

12. The thrombus removal device of claim 9, wherein the cavitation detection sensor comprises an ultrasound transducer element.

13. The thrombus removal device of claim 9, wherein the cavitation detection sensor comprises a laser.

14. The thrombus removal device of claim 1, further comprising a real-time imaging device configured to image the cavitation in real-time.

15. A method for removing a thrombus from a blood vessel of a patient, the method comprising:

introducing a distal portion of an elongate catheter to a thrombus location in a blood vessel;

drawing at least a section of the thrombus into the distal portion; and after drawing the thrombus into the distal portion, generating two or more fluid streams towards an intersection point within the distal portion, the fluid streams having a flow rate of at least 50 m/s that interact at the intersection point to create cavitation within the thrombus.

16. A method for removing a thrombus from a blood vessel of a patient, the method comprising:

introducing a distal portion of an elongate catheter to a thrombus location in a blood vessel;

drawing at least a section of the thrombus into the distal portion; and after drawing the thrombus into the distal portion, generating two or more fluid streams that intersect within the distal portion at an intersection point, wherein the two or more fluid streams are configured to apply at least four distinct breaking forces to the thrombus including:

1) a slicing force as the two or more fluid streams initially cut through the thrombus prior to meeting at the intersection point;

2) a cavitation force at the intersection point when the two or more fluid streams interact to generate cavitation;

3) a shearing force caused by the two or more fluid streams moving against each other to generate shearing cavitation; and 4) a rotational fluid motion force caused by the shearing force and the cavitation force.

17. The method of claim 16, wherein the drawing is by suction applied via an aspiration lumen of the elongate catheter.

18. The method of claim 16, wherein generating the two or more fluid streams further comprises directing the two or more fluid streams proximally relative to fluid stream apertures of the elongate catheter.

19. The method of claim 16, wherein generating the two or more fluid streams further comprises directing the two or more fluid streams distally relative to fluid stream apertures of the elongate catheter.

20. The method of claim 16, wherein generating the two or more fluid streams further comprises directing the two or more fluid streams generally orthogonal to a longitudinal axis of the elongate catheter.

21. A thrombus removal device, comprising:

an elongate shaft comprising a working end;

at least one fluid lumen in the elongate shaft;

two or more apertures disposed at or near the working end, the two or more apertures in fluid communication with the at least one fluid lumen and configured to generate two or more fluid streams that interact within or near the working end at an interaction region, the two or more fluid streams having a flow rate and proximity sufficient to induce cavitation at the interaction region that is configured to mechanically morcellate a target thrombus; and a cavitation detection sensor comprising an ultrasound transducer element disposed on or within the thrombus removal device.

22. A thrombus removal device, comprising:

an elongate shaft comprising a working end;

at least one fluid lumen in the elongate shaft;

two or more apertures disposed at or near the working end, the two or more apertures in fluid communication with the at least one fluid lumen and configured to generate two or more fluid streams that interact within or near the working end at an interaction region, the two or more fluid streams having a flow rate and proximity sufficient to induce cavitation at the interaction region that is configured to mechanically morcellate a target thrombus; and a cavitation detection sensor comprising a laser disposed on or within the thrombus removal device.

* * * * *